US012653403B2

(12) United States Patent
Li et al.

(10) Patent No.: US 12,653,403 B2
(45) Date of Patent: Jun. 16, 2026

(54) FIBER-OPTICAL SENSOR ARRAY FOR SENSING AND IMAGING

(71) Applicant: DEEPSIGHT TECHNOLOGY, INC., Santa Clara, CA (US)

(72) Inventors: Fu Li, St. Louis, MO (US); Mucong Li, St. Louis, MO (US); Yihang Li, St. Louis, MO (US); Linhua Xu, University City, MO (US); Lan Yang, Clayton, MO (US); Guangming Zhao, Beijing (CN); Jiangang Zhu, St. Louis, MO (US); Mike Hazarian, San Jose, CA (US); Haochen Kang, Sunnyvale, CA (US)

(73) Assignee: DEEPSIGHT TECHNOLOGY, INC., Santa Clara, CA (US)

( * ) Notice: Subject to any disclaimer, the term of this patent is extended or adjusted under 35 U.S.C. 154(b) by 0 days.

(21) Appl. No.: 18/609,378

(22) Filed: Mar. 19, 2024

(65) Prior Publication Data

US 2024/0423481 A1     Dec. 26, 2024

Related U.S. Application Data

(60) Provisional application No. 63/545,327, filed on Oct. 23, 2023, provisional application No. 63/522,994, (Continued)

(51) Int. Cl.
*A61B 5/00* (2006.01)
*G01H 9/00* (2006.01)
(Continued)

(52) U.S. Cl.
CPC .......... *A61B 5/0095* (2013.01); *A61B 5/0097* (2013.01); *G01S 7/52079* (2013.01);
(Continued)

(58) Field of Classification Search
CPC .. A61B 5/0097; G01H 9/004; G01S 15/8965; G01S 15/8968
See application file for complete search history.

(56) References Cited

U.S. PATENT DOCUMENTS 5,961,463 A     10/1999   Rhyne et al.
8,560,048 B2   10/2013   Rourke et al.
(Continued)

FOREIGN PATENT DOCUMENTS

CN     102119323 A     7/2011
CN     107621274 A     1/2018
(Continued)

OTHER PUBLICATIONS

Baker et al., "Intraoperative Needle Tip Tracking with an Integrated Fibre-Optic Ultrasound Sensor," Sensors 22 (9035):1-28 (2022).
(Continued)

*Primary Examiner* — Amelie R Davis
(74) *Attorney, Agent, or Firm* — MEDLER FERRO WOODHOUSE & MILLS PLLC

(57) ABSTRACT

Mixed sensor array devices are provided herein. Mixed sensor arrays as described herein include acoustic energy generating elements and optical fiber based acoustic sensors. Optical fiber based sensors may optical structures responsive to physical parameters including acoustic signals, pressure, and temperature, and are configured to detect and receive acoustic signals and other physical parameters and provide associated optical signals to a system for processing and interpretation to implement tracking, location, imaging, and other sensing capabilities. Optical fiber based sensors provided herein may be disposed at ends of or along the length of optic fibers. Optical fiber based sensors may be included within various devices, including, for example, medical devices.

24 Claims, 54 Drawing Sheets

Related U.S. Application Data filed on Jun. 23, 2023, provisional application No. 63/522,793, filed on Jun. 23, 2023, provisional application No. 63/510,079, filed on Jun. 23, 2023, provisional application No. 63/592,482, filed on Oct. 23, 2023.

(51) Int. Cl.
  *G01S 7/52* (2006.01)
  *G01S 15/89* (2006.01)

(52) U.S. Cl.
  CPC .......... *G01H 9/004* (2013.01); *G01S 15/8965* (2013.01); *G01S 15/8968* (2013.01)

(56) References Cited

U.S. PATENT DOCUMENTS

| | | | |
|---|---|---|---|
| 10,595,816 B2 | 3/2020 | Tahmasebi Maraghoosh et al. | |
| 11,647,957 B2 | 5/2023 | Desjardins et al. | |
| 2001/0042410 A1 | 11/2001 | Ogawa | |
| 2004/0067000 A1* | 4/2004 | Bates ..................... | G01H 9/004 |
| | | | 385/37 |
| 2005/0169590 A1* | 8/2005 | Alkeskjold ........ | G02B 6/02385 |
| | | | 385/123 |
| 2008/0128506 A1 | 6/2008 | Tsikos et al. | |
| 2012/0059259 A1 | 3/2012 | Emery et al. | |
| 2015/0133787 A1 | 5/2015 | Wegner | |
| 2016/0038119 A1 | 2/2016 | Desjardins | |
| 2016/0045184 A1 | 2/2016 | Courtney et al. | |
| 2016/0245687 A1 | 8/2016 | Digonnet et al. | |
| 2017/0172539 A1 | 6/2017 | Vignon et al. | |
| 2017/0307741 A1 | 10/2017 | Ralston et al. | |
| 2017/0370704 A1* | 12/2017 | Froggatt ................. | G01L 1/242 |
| 2020/0077974 A1* | 3/2020 | Avanaki ................. | A61B 8/085 |
| 2020/0319019 A1 | 10/2020 | Westerveld et al. | |
| 2021/0325237 A1* | 10/2021 | Rozental .............. | A61B 5/0095 |
| 2022/0350022 A1 | 11/2022 | Zhao et al. | |
| 2022/0365036 A1 | 11/2022 | Yang et al. | |
| 2023/0097639 A1 | 3/2023 | Zhu et al. | |
| 2023/0148869 A1 | 5/2023 | Zhao et al. | |

FOREIGN PATENT DOCUMENTS

| | | | |
|---|---|---|---|
| CN | 110859601 A | 3/2020 | |
| CN | 112212964 A | 1/2021 | |
| CN | 115969409 A | 4/2023 | |
| JP | 2003169801 A | 6/2003 | |
| JP | 2021517243 A | 7/2021 | |
| JP | 2023504589 A | 2/2023 | |
| WO | 2010005574 A2 | 1/2010 | |
| WO | 2020/208524 A1 | 10/2020 | |
| WO | 2021055823 A2 | 3/2021 | |
| WO | 2023064492 A1 | 4/2023 | |

OTHER PUBLICATIONS

BD Cue™ Needle Tracking System with BD Prevue™ II Vascular Access System, YouTube, retrieved from internet Feb. 29, 2024 from, <<https://www.youtube.com/watch?v=YqCXAH3gzkg>>.

International Search Report, International Application No. PCT/US2022/077762, Mailing Date: Jan. 17, 2023.

Kåsine et al., "Needle tip tracking for ultrasound-guided peripheral nerve block procedures—An observer blinded, randomised, controlled, crossover study on a phantom model," Acta anaesthesiologica Scandinavica 63(8):1055-1062 (2019).

Mari et al., "Needle-tip localization using an optical fibre hydrophone," Proceedings of SPIE—The International Society for Optical Engineering 8938:1-8 (2014).

Onvision® Needle Tip Tracking Demonstration Video, YouTube, retrieved from internet on Feb. 29, 2024, <<https://www.youtube.com/watch?v=2lxvrwsG39c&t=8s>>.

Xia et al., "Coded excitation ultrasonic needle tracking: An in vivo study," Medical Physics 43(7):4065-4073 (2016).

Dong et al., "Optical Detection of Ultrasound in Photoacoustic Imaging," IEEE Transactions on Biomedical Engineering 64(1):4-15 (2017).

Hou et al., "Simultaneous Measurement of Pressure and Temperature in Seawater with PDMS Sealed Microfiber Mach-Zehnder Interferometer," Journal of Lightwave Technology 38(22):6412-6421 (2020).

Thathachary et al., "Polymer Waveguides for Improved Sensitivity in Fiber Fabry-Perot Ultrasound Detectors," IEEE Sensors Journal 21(1):43-50 (2021).

Ma et al., "A Fabry-Perot Fiber-Optic Array for Photoacoustic Imaging," IEEE Transactions on Instrumentation and Measurement 71:2-9 (2022).

Sorazu et al., "Ultrasonic wavefront integration using optical fibre sensors," Proceedings of SPIE 5050:23-33 (2003).

* cited by examiner

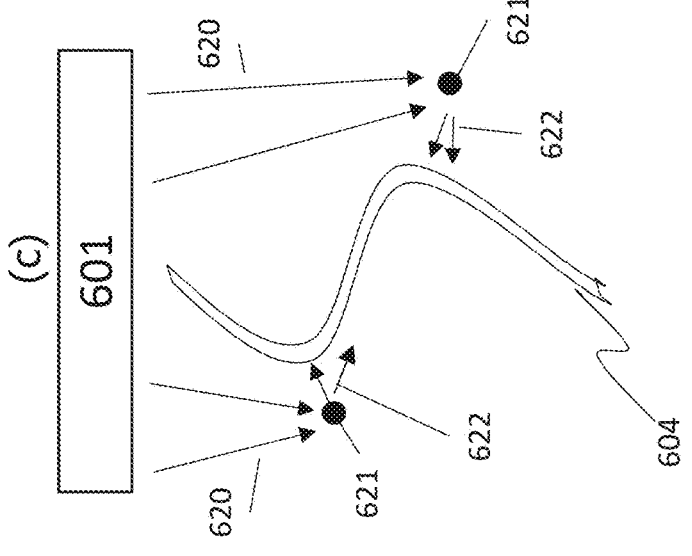
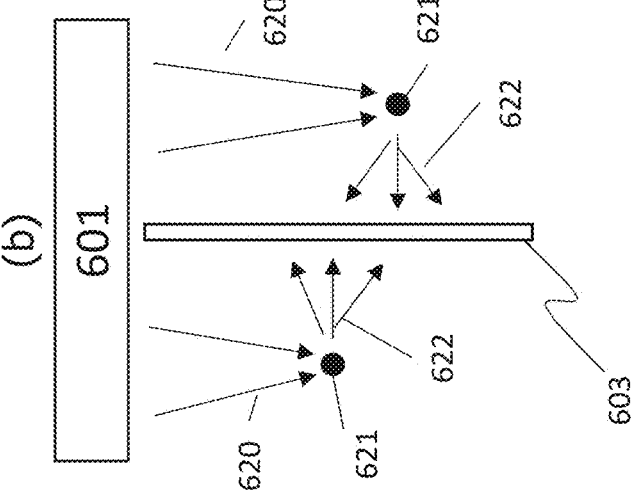
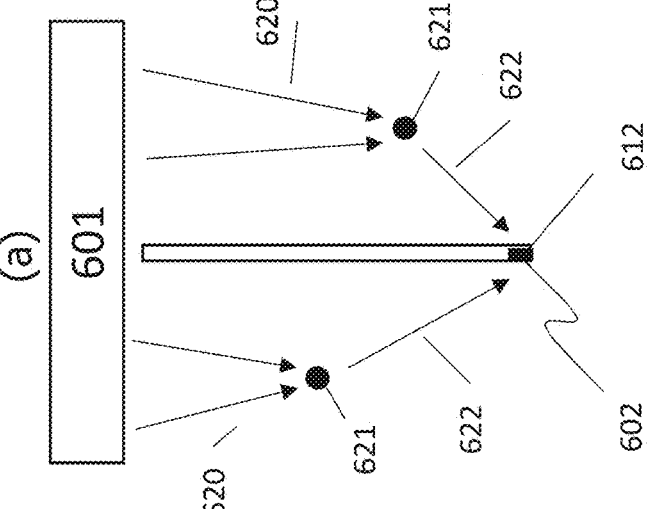
FIG. 6DD

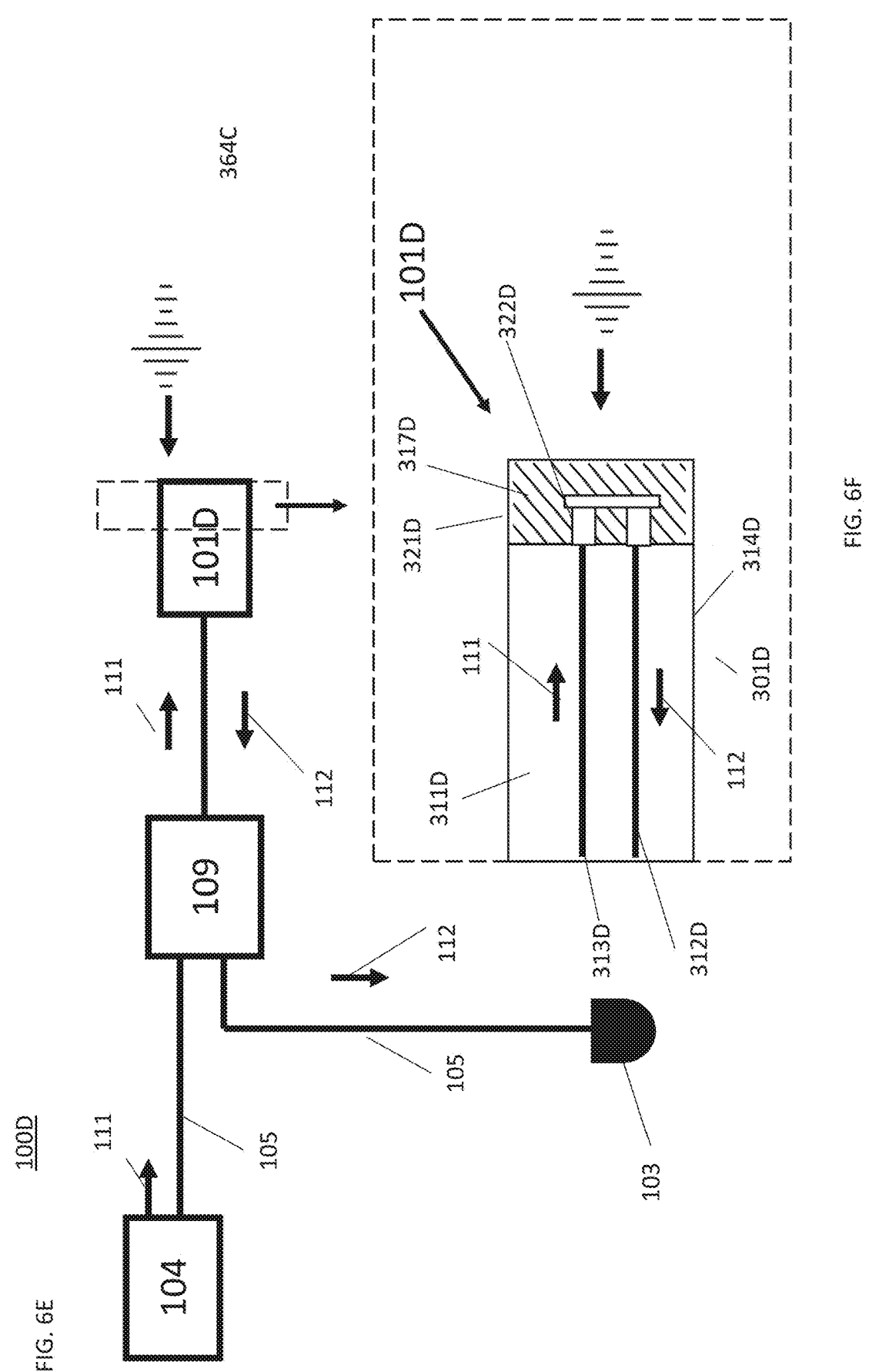

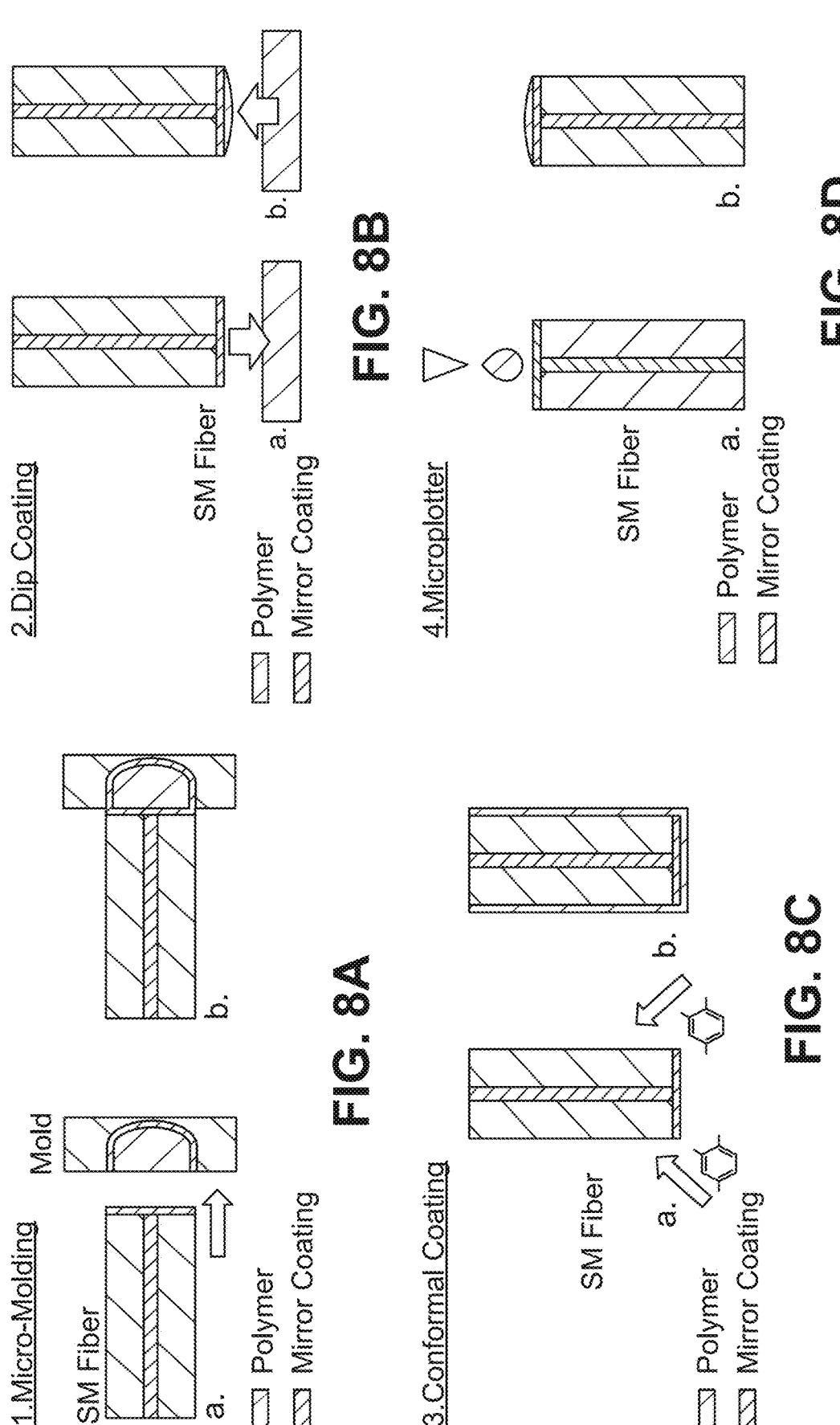

2000

Probe Transmits Acoustic Pulses 2010

Fiber Sensor Receives Ultrasound Pulses 2020

Determine Location of Fiber Sensor Based on Ultrasound Signals 2030

Generate Ultrasound Image 2040

Modify Ultrasound Image Based on Ultrasound Pulses Sensed by Fiber Sensor 2050

Overlay Location of Fiber Sensor on Ultrasound Image 2060

1901

1903

1902

1904

1905

2511
2512
2513
2514
2573
2520
2507
2506

2501
2502
2573
2500
2510
2507
2506

FIBER-OPTICAL SENSOR ARRAY FOR SENSING AND IMAGING

RELATED APPLICATIONS

This application claims priority to U.S. Provisional Application No. 63/510,079, titled FIBER-OPTICAL SENSOR SYSTEM FOR ULTRASOUND SENSING AND IMAGING and filed on Jun. 23, 2023, U.S. Provisional Application No. 63/522,793, titled OPTICAL FIBER WITH AN ACOUSTICALLY SENSITIVE FIBER BRAGG GRATING AND ULTRASOUND SENSOR INCLUDING THE SAME, and filed Jun. 23, 2023, U.S. Provisional Application No. 63/522,994, titled "TRANSPONDER TRACKING AND ULTRASOUND IMAGE ENHANCEMENT," filed Jun. 23, 2023, U.S. Provisional Patent Application No. 63/545,327 titled MINIATURE MIXED ARRAY IMAGING PROBE, filed on Oct. 23, 2023, filed on Oct. 23, 2023, each of which is incorporated herein by reference. This application is further related to U.S. patent application Ser. No. 18/382,984 titled TRANSPONDER TRACKING AND ULTRASOUND IMAGE ENHANCEMENT and having been filed on Oct. 23, 2023, which is incorporated by reference herein.

TECHNICAL FIELD

This invention relates generally to the field of ultrasound sensing, imaging and optical sensing.

BACKGROUND

Acoustic imaging is used in various industries including medical imaging. Acoustic imaging technologies may be used to visualize and provide internal imaging of a patient's body. Furthermore, acoustic imaging technology may be used to visualize and track objects (e.g., needles, catheters, guidewires, endoscopes and the like), used in medical applications such as diagnostic or therapeutic clinical procedures including, but not limited to biopsy, fluid aspiration, delivery of therapeutics such as drugs, nerve blocks/anesthesia or biologics, catheterization, needle guidance, needle placement, deep vein cannulation, injection, placement of IV, PIC lines, device implantation, minimally invasive surgical procedures etc. Using acoustic imaging for medical applications offers several advantages. For instance, acoustic imaging such as ultrasound imaging is a non-invasive form of imaging. Additionally, ultrasound imaging uses ultrasound signals which are known to have remarkable penetration depth.

In non-medical applications, ultrasound is used in industrial applications for defect detection, non-destructive testing, structural testing, and microparticle particle sorting among other applications, geological applications including mining and drilling operations and underwater marine applications.

Some existing imaging technology use Acoustic Energy Generating (AEG) materials for transducers to visualize and track medical objects and to generate imagery during a diagnostic or therapeutic medical procedure. Commonly used AEG materials include piezoelectric materials such as lead-zirconate-titanate (PZT), ceramic, piezoelectric single crystal (e.g., PIN-PT, PIN-PMN-PT), and polyvinylidene fluoride (PVDF) among many other materials known to those of skill in the art. AEG transducers have limitations. The echogenicity of the object to be tracked and/or anatomy being visualized can affect the image quality of the object being tracked and the tissue being imaged. In certain medical procedures a small form factor is needed, and small AEG transducers generally have low to minimal signal output. Therefore, it may be challenging to use AEG transducers for medical applications requiring a small form factor because of the size limitations (e.g., physical size).

Accordingly, there is a need for new and improved compact technology with high sensitivity to visualize and track objects, provide anatomical imaging, and provide measurements of other physical parameters, particularly in medical applications.

SUMMARY

Systems, devices, and methods for ultrasound sensing, imaging and multi-dimensional sensing of physical parameters are presented herein. In particular, systems, devices, and methods described herein may include fiber microsensor devices and systems and methods of use.

In some aspects, the techniques described herein relate to an apparatus including: a housing; a substrate mounted within the housing; a plurality of sensor fibers secured to the substrate, each sensor fiber including: an optical waveguide; an optical sensor structure configured for: detecting an acoustic signal, and providing an optical signal corresponding to the acoustic signal to the optical waveguide, and a plurality of acoustic energy generating transducers configured to generate acoustic energy.

In some aspects, the techniques described herein relate to a system for generating ultrasound images, including: a light source configured to generate an initial optical signal; a first optical waveguide configured to direct the initial optical signal from the light source to a fiber optic acoustic sensor array configured to detect acoustic signals; a light receiving device configured to receive a returned optical signal from the fiber optic acoustic sensor array and to generate optical signal data based on the returned optical signal; a second optical waveguide configured to direct the returned optical signal to the light receiving device; an acoustic control unit configured to provide acoustic control data to and receive acoustic signal data from an array of acoustic energy generating transducers; and a processing system configured to receive the optical signal data and the acoustic signal data and to generate a data output.

In some aspects, the techniques described herein relate to an apparatus including: a housing; a substrate mounted within the housing; a plurality of sensor fibers secured to the substrate, each sensor fiber including: an optical waveguide; an optical sensor structure configured for: detecting a physical parameter, and providing an optical signal corresponding to the physical parameter to the optical waveguide, and a plurality of acoustic energy generating transducers configured to generate acoustic energy.

In some aspects, the devices described herein relate to an apparatus including: a sensor fiber including: an optical waveguide including a core and a cladding structure; an optical sensor structure coupled to a first end of the optical waveguide including at least one of an optical resonator, an optical interferometer, a facet end microstructure, and a polarization sensitive structure, the optical sensor structure being configured for: detecting an acoustic signal, and providing an optical signal corresponding to the acoustic signal to the optical waveguide, multi-dimensional sensing of physical parameters, and providing an optical signal corresponding to the sensed physical parameter.

BRIEF DESCRIPTION OF THE DRAWINGS

The accompanying figures, which are incorporated herein, form part of the specification and illustrate embodiments of systems, methods, and devices for ultrasound sensing and imaging. Together with the description, the figures further explain the principles of and enable a person skilled in the relevant art(s) to make and use the methods, systems, and devices described herein. The drawings are provided to illustrate various features of the embodiments described herein and are not necessarily drawn to scale. In the drawings, like reference numbers indicate identical or functionally similar elements.

FIGS. 6A-6DD illustrate examples of an optical sensor system and fiber optical sensor consistent with embodiments hereof.

FIGS. 6E and 6F illustrate examples of an optical sensor system and fiber optical sensor consistent with embodiments hereof.

FIG. 8A-FIG. 8D provide examples of manufacturing techniques that may be used to manufacture an optical resonator structure at an end of an optical waveguide.

FIG. 33C illustrates a probe head module as viewed in an axial dimension according to embodiments herein.

FIG. 35C illustrates the probe head module as viewed in an axial dimension according to embodiments herein.

DETAILED DESCRIPTION

Figure 1:
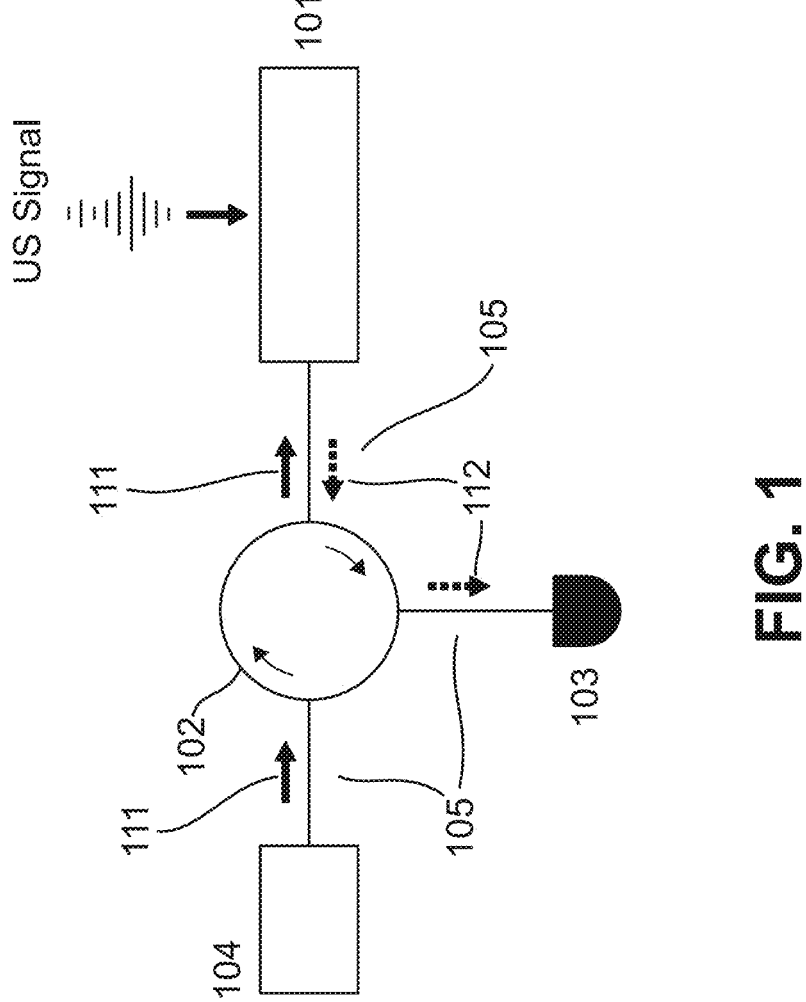
FIG. 1 illustrates an optical sensor system for use with a fiber optical sensor consistent with embodiments hereof.

Non-limiting examples of various aspects and variations of the invention are described herein and illustrated in the accompanying drawings. The following detailed description is merely illustrative in nature and is not intended to limit the invention or the application and uses of the invention. Although the description of the invention is in the context of fiber optical micro-sensor systems, methods, and devices for ultrasound imaging and sensing, the disclosure should not be considered so limiting. For example, although methods may be discussed herein with respect to various medical procedures, embodiments hereof may be suitable for other medical procedures as well as other procedures or methods in other industries that may benefit from the sensing and imaging technologies described herein. Further, various systems and devices that incorporate fiber micro-sensors are described. It is understood that fiber micro-sensors, as described herein, may be integrated into and/or used with a variety of systems and devices not described herein. Modifications may be made to the embodiments described herein without departing from the spirit and scope of the present invention. Therefore, the following detailed description is not meant to be limiting. Furthermore, there is no intention to be bound by any expressed or implied theory presented in the preceding technical field, background, summary, or the following detailed description.

Various structures are described herein according to their geometric properties. As discussed herein, all structures so described may vary from the described shape according to the tolerances of known manufacturing techniques. Unless otherwise specified, features described with the term "substantially" are understood to be within 5% of exactness. For example, features described as "substantially parallel" may deviate from true parallel by 5%.

Systems, devices, and methods for measurement of physical parameters through the use of optical fiber sensor structures are described herein. Broadly speaking, optical fiber sensor structures described herein may experience physical changes in response to external stimuli. Such external stimuli may include, for example, temperature and pressure changes, incident acoustic signals, and others. Such physical changes, which may include structural changes, changes to material properties or characteristics, and others described herein, may result in measurable changes to characteristic properties. For example, optical signals incident on and reflected by optical fiber sensor structures as described herein may be influenced by such physical changes. Accordingly, a returned optical signal may have characteristics that are indicative of the physical changes to the optical fiber sensor structures, and thus indicative of the environmental conditions or external stimuli that produced such physical changes. In an example, changing the temperature of an optical fiber sensor structure as described herein may result in measurable differences in a returned optical signal, thus permitting the optical fiber sensor structure to be used for temperature measurement purposes. In another example, incident acoustic signals (e.g., pressure changes) on an optical fiber sensor structure as described herein may result in measurable differences in a returned optical signal, thus permitting the optical fiber sensor structure to be used for measuring acoustic response (e.g., for ultrasound imaging, tracking, location, etc.) These and other examples are described in greater detail below. Such examples, whereby a given optical sensor structure may be employed or used for measuring multiple different physical parameters or external stimuli (e.g., temperature and pressure) may be referred to as multi-dimensional sensing.

Such systems, devices, and methods may be configured for ultrasound sensing and imaging by the use of fiber micro-sensor or fiber sensor devices are disclosed. In particular, the technology described herein may track, visualize, and monitor (e.g., sense) objects during medical procedures as well as generate ultrasound images. The fiber micro-sensor devices described herein incorporate optical devices disposed at the end of optical fibers or designated locations along its length and configured for the detection of acoustic signals, including ultrasound signals. Sensor fibers, as described herein, include an optical waveguide (such as an optical fiber) with a fiber micro-sensor device coupled at an end thereof. As used herein the term optical waveguide may refer to optical fibers, optical fiber cores, photonic integrated waveguides, planar waveguides, etc., based on material systems like fused glass, polymer, semiconductor/dielectric wafer, nanoimprinted/3D printed polymer on different substrates or any other optical signal channel.

The technology described herein is compact in size and has high sensitivity, thereby making it viable for various industrial applications and therapeutic and diagnostic medical applications. In non-medical applications, ultrasound is used in industrial applications for defect detection, non-destructive testing, structural testing and microparticle particle sorting among other applications, geological applications including mining and drilling operations and underwater marine applications. Such applications are consistent with embodiments described herein. Therapeutic and diagnostic medical applications include ultrasound imaging as well as sensing (tracking, visualizing, guiding and monitoring) of objects (e.g., needle, catheter, guidewire, trocar, introducer, stylet etc.) during guided needle access, biopsy, aspiration, delivery of drugs, biologics, anesthesia or other therapeutics, catheterization, minimally invasive procedures, ablation, cauterization, placement or moving of objects, tissue, cutting and/or sectioning, and other medical procedures. Procedures and applications in the following disciplines are examples of the wide usage and need for accurate guidance and imaging during diagnostic and therapeutic procedures: anesthesia, cardiology, critical care, dermatology, emergency medicine, endocrinology, gastroenterology, gynecology and obstetrics, hepatology, infectious diseases, interventional radiology, musculoskeletal medicine, nephrology, neurology, oncology, orthopedics, pain management, pediatrics, plastic and reconstructive surgery, urology and vascular access Object visualization, tracking, guidance and location determination in medical applications may be important aspects for performing medical procedures in a safe and reliable manner. Objects for tracking, visualization, and location determination may include any type of medical device that travels or is located within the body of a subject. For instance, medical practitioners visualize and track a needle tip while conducting a biopsy to ensure safety. In such instances, accurate needle tip visualization or tracking may help to prevent or reduce unintentional vascular, neural, tissue or visceral injury. Similarly, it may be helpful to visualize, track, or locate needles, endoscopes, cannulas, laparoscopic tools or other medical device tools when performing medical procedures such as, but not limited to, aspiration of fluid; injections of joints, tendons, and nerves with drugs or biologics; biopsy of fluids or soft tissue masses; aspiration and lavage of calcifications; removal of tissue, organs or foreign bodies, placement of a stent, filter, valve, permanent, temporary or biodegradable implant, shunt or drain, injections for anesthesia, inserting vascular access devices used for infusion therapies, ablation procedures, performing the Seldinger technique or catheterization to gain access to blood vessels and/or other organs in a safe manner. Visualization and tracking may be advantageous in both laparoscopic procedures, minimally invasive procedures and open surgical procedures, especially when it is difficult to visualize the area due to limited access, intervening tissue or organs blood or other fluid.

Some existing technologies use ultrasound imaging for guidance during medical procedures, to visualize anatomical structures of interest as well as to visualize, locate, and track inserted medical devices, especially the distal and/or working portion of the device. However, there are several drawbacks associated with conventional ultrasound imaging technology for medical applications. Traditional technology uses imaging probes that emit ultrasound waves. Because of the smooth surface of needles and other inserted medical devices, the incident ultrasound waves reflected from the surface may be steered away from the receiving direction. This may make the reflected waves too weak to be detected easily, making it difficult to determine the location of the device during the procedure. In some technologies, the medical device may have a roughened surface, such a dimpled, etched or coated surface to increase visibility in ultrasound by increasing the echogenicity of the medical device. However, even with such efforts, limitations remain. Ultrasound-guided tools may also be constrained by their dependence on specific incident angles, which limit their ability to provide accurate visualization, particularly for deeply placed devices. Due to this constraint, ultrasound-guided tools may be relegated to superficial locations which limits their utility, adoption, and cost-effectiveness as a deployable solution.

There are at least two key acoustic performance limitations in the current state-of-art AEG transducers (such as, but not limited to, piezoelectric materials such as lead-zirconate-titanate (PZT), ceramic, piezoelectric single crystal (e.g., PIN-PT, PIN-PMN-PT), polymer thick film (PTF), polyvinylidene fluoride (PVDF), capacitive micromachined ultrasonic transducers (CMUT), piezoelectric micromachined ultrasound transducers (PMUT), among other materials known to those of skill in the art.) compared to the proposed optical sensing technique. First, achieving very high sensitivities requires transducers fabricated from specific AEG materials or specific acoustic designs, but such transducers may provide only a relatively narrow bandwidth in acoustic response. Secondly, the acoustic response of AEG transducers may be restricted due to electrical impedance mismatches when the electrical element sizes become small with respect to their resonant frequency. As a result, for applications requiring a small form factor (e.g., intravascular or intracardiac ultrasound, endoscopic, needle tracking, lung biopsy, sensing, and monitoring, etc.), the signal-to-noise ratio (SNR) and bandwidth of a small AEG transducer is reduced and in certain applications may also present a highly directional response. Additionally, some AEG transducers and systems may be affected by electromagnetic interference, such as that caused by ablation tools, cauterization tools, or any other procedure or technique that applies electrical energy to tissue. Furthermore, use of an electro-mechanical transducer at the distal end will include an electrically conductive line and associated components requiring additional design and safety requirements and challenges.

In contrast, fiber optical sensors consistent with the present disclosure are able to provide ultrasound receivers with high sensitivity, broad bandwidth, and a wide acceptance angle and do not require the electrical components needed for electro-mechanical transducers. With these characteristics, fiber optical sensors will be able to sense harmonic or scattered signals that existing technologies cannot sense.

The fiber optical sensor of the present invention may also be used for multi-dimensional sensing of various physical parameters (e.g., environmental conditions, external stimuli, etc.) The use of optical sensors as multi-dimensional sensors for sensing physical parameters alleviates many difficulties associated with combining multiple sensors and their various components and connections. To accomplish multi-dimensional sensing, measurement signals are generated from optical sensor responses, where each of these measurement signals may be indicative of a respective physical signal, physical parameter, external stimulus, environmental condition, etc. For example, a signal processor may generate a temperature measurement signal based at least in part on the resonant frequency shift of an optical sensor structure that is caused by a temperature change (e.g., mode shift) and an acoustic measurement signal based at least in part on oscillation of optical power that is caused by incident acoustic signals. Multi-dimensional sensing may also be achieved by using multiple sensors, each responding differently to different sensing targets. Variations of generating measurement signals from optical sensor responses, may include decoupling individual physical signals and/or collectively analyzing the multiple sensor responses to determine individual physical signals.

Further, fiber optical sensors consistent with the present disclosure may be compact, low cost, and may contribute to a scalable sensor system. Embodiments hereof include fiber optical sensors configured to detect acoustic signals and other physical parameters. Such fiber optical sensors may be disposed at the end of an optical fiber, adjacent an end of an optical fiber or at a diagnostic or therapeutic relevant location on the medical device to create a sensor fiber. Fiber optical sensors include resonant structures, including, but not limited to Fabry-Perot (FP) resonators, optical cavity resonators, whispering-gallery-mode resonators, and photonic crystal resonators; optical interferometers, including but not limited to MZI, phase-shift coherent interferometers, self-mixing interferometers; acoustically responsive fiber end facets; and acoustic induced birefringent polarization sensors.

Acoustically responsive fiber end facets may comprise a substrate suitable for adding various microstructures to enhance the response of the fiber sensor to acoustic signals. Such microstructures may be acoustically responsive structures such as metasurfaces including patterns of small elements (e.g., having a size less than approximately one wavelength of the optical signal) arranged to change the wavefront shape of the acoustic signals and maximize the detection of acoustic signals, acoustically responsive low-dimensional materials with special optomechanical features that are more prone to deformation, and plasmonic structures patterned to amplify light-matter interactions. In embodiments, the microstructures discussed herein may also be used to detect additional physical parameters beyond acoustic signals, as described herein. In addition to operating as an optical sensor, the fiber end facet structures may also be added to the other fiber optical sensors described herein to further enhance acoustic response. For example, a meta-surface may include patterns of small elements arranged so as to change the wavefront shape of the acoustic signals and maximize the collection of acoustic signals collected by the other types of fiber optical sensors discussed herein to improve the sensitivity of the fiber optical sensors. Adding low-dimensional materials to a fiber end facet may also improve sensitivity because such materials are more prone to deformation induced by acoustic waves, which may translate into larger changes in the optical signal. By writing plasmonic patterns onto a fiber end facet, it is possible to enhance the optical response to acoustic waves. This enhancement may be achieved through leveraging the hot-spots and resonances generated by these plasmonic patterns to amplify light-matter interactions. As used herein, "low-dimensional" or "2 dimensional" features may refer to features having a thickness of less than 1 micron.

The aforementioned optical structures are configured to respond to acoustic (such as ultrasound) signals as well as other physical parameters. Thus, these optical structures may include acoustically responsive materials and/or acoustically responsive structures. Acoustically responsive, as used herein, refers to structures or materials that are configured to respond to incident acoustic signals (e.g., ultrasound acoustic signals) in a manner that adjusts the optical properties of the materials or structures. Reponses to acoustic signals in such resonant, interferometer or acoustically responsive fiber end facet structures may be due to the photo-elastic effect and/or physical deformation of the structures. When subject to acoustic signals, the resonant, interferometer or acoustically responsive fiber end facet structures are subject to mechanical stress and/or strain from the alternating pressures of the acoustic signal sound waves. This mechanical stress and/or strain may change the optical properties of the optical sensor structures due to the photo-elastic effect and may also cause changes or deformations in the physical structure of resonator. With polarization-based sensors, the polarization of optical signals changes when the medium through which the light is passing is subjected to acoustic signals. When coupled to a light source (e.g., a laser light source, a broadband light source (e.g., a lamp or LED) or other suitable light source) via an optical waveguide (e.g., an optical fiber), the effect of acoustic signals on the optical sensor structures may be measured due to changes in the light returned by the optical sensor structures via the optical waveguide.

Similar techniques may be used with respect to other physical parameters. For example, the optical properties of the optical sensor structures may vary according to temperature and/or pressure, thus resulting in signals that may be measured due to changes in the light returned by the optical sensor structures. As discussed herein, for example, a resonant frequency of an optical sensor structure may vary according to the temperature of the structure. In some embodiments, thermal tuning may be used to reduce or eliminate temperature variations so as to provide a more accurate measurement of other stimuli (e.g., acoustic signals). In further embodiments, however, the variations of temperature may be measured according to the resonant frequency shift.

A given optical sensor structure may have different sensitivities to different physical parameters. For example, an optical sensor structure may have a first sensitivity to acoustic signals (pressure) and a first sensitivity to temperature changes. It may be difficult to use such a sensor to measure either the acoustic signal or the temperature without either knowledge or control of the element that is not being measured. If the pressure response signal is dependent on temperature, it may be difficult to measure the pressure response signal without either controlling or knowing the temperature. When the pressure response signal changes, it may be difficult to understand whether the change was due to a temperature change, a pressure change, or both. Accordingly, some embodiments discussed herein include such techniques to enable control or knowledge of the physical parameter that is not being measured.

In other techniques, multi-dimensional measurement may be enabled through the use of multiple optical sensor structures having different sensitivities. In an example, a first optical sensor structure has a first sensitivity to acoustic signals (pressure) and a first sensitivity to temperature changes. A second optical sensor structure has a second sensitivity to acoustic signals and a second sensitivity to temperature changes. If the first and second sensitivity to temperature changes are different, then differences in response signals between the first optical sensor structure and the second optical sensor structure when subject to the same external stimuli can be understood to be attributable to temperature. Thus, when a response signal changes, the portion of the change that is attributable to temperature and the portion attributable to pressure may be identified. Similar principles apply wherein the first and second sensitivity to acoustic signals (pressure) is different or wherein the sensitivities to both temperature and acoustic signals are different. In further embodiments, third, fourth, fifth, and/or more optical sensor structures may be included that also have a difference in sensitivity to at least one of temperature and acoustic signals.

Accordingly, embodiments herein include optical sensor arrays that include a plurality of fiber optical sensors, wherein at least one optical sensor within the array has a difference in sensitivity in either temperature response sensitivity, pressure response sensitivity, or both.

Within this disclosure, optical signals and light may be referred to as responding to acoustic signals or other physical parameters. It is understood that such responses are due to the interaction between the acoustic signals or physical parameters and the medium through which the light passes. Thus, as discussed herein, a material or structure that is referred to as acoustically responsive may respond to acoustic signals typical of an ultrasound environment in manner that can be measured, by techniques discussed herein, by optical signals consistent with embodiments hereof. In further embodiments, materials or structures may be selected for their responsive to other physical parameters, such as temperature and/or pressure.

The fiber optical sensors discussed herein can be sensitive to a variety of physical stimuli or physical parameters. An optical sensor intended to measure acoustic signals may also be sensitive to other physical parameters such as temperature change. An optical sensor may be designed to maximize sensitivity to an intended stimuli or signal, such as acoustic signals. Such a sensor remains sensitive to other stimuli which may cause errors or inaccuracies in measurement of the intended/primary physical stimuli. By introducing an additional sensor with different sensitivities, one may better discriminate/identify which physical stimuli is causing the signal shift.

Furthermore, in many applications, it is desirable to detect multiple kinds of physical stimuli or parameters. For example, in the field of medical technology, it may be advantageous to have medical devices with sensors that can sense multiple different physical parameters (e.g., simultaneously in real-time or near real-time). For example, ablation catheters for cardiovascular procedures may include temperature sensors to measure the temperature of the treated tissues and force sensors to measure the force applied to the arterial wall during heart ablation. In some solutions, multiple kinds of sensors may be incorporated together in a single device to monitor multiple different kinds of parameters, in addition to, or instead of, imaging. However, the inclusion of more sensors may result in a device that may be more challenging to fit into a desired form factor. Additionally or alternatively, the inclusion of more sensors may pose more difficulties in accommodating additional components (e.g., mechanical and/or electrical) and connections to enable proper functioning of all of the different sensors.

The use of optical sensors as multi-dimensional sensors for sensing physical parameters alleviates many difficulties associated with combining multiple sensors and their various components and connections. To accomplish multi-dimensional sensing, measurement signals are generated from optical sensor responses, where each of these measurement signals may be indicative of a respective physical signal. For example, a signal processor may generate a temperature measurement signal based at least in part on the resonant frequency shift (e.g., mode shift) and an acoustic measurement signal based at least in part on oscillation of optical power. Multi-dimensional sensing can also be achieved by using multiple sensors, each responding differently to different sensing targets. Variations of generating measurement signals from optical sensor responses, may include decoupling individual physical signals and/or collectively analyzing the multiple sensor responses to determine individual physical signals.

Embodiments hereof include systems configured for use with fiber optical sensors. For example, systems consistent with the present disclosure may include light sources (e.g., laser light sources, a broadband light source (e.g., a lamp or LED) or other suitable light source), light reception devices (e.g., photodetectors, etc.), optical devices (splitters, couplers, combiners, circulators, polarization sensitive couplers, polarization analyzers, polarization controllers, frequency shifters, etc.), control devices, computer processing units, and other devices to facilitate the functionality of the fiber optical sensors. Further, such systems consistent with the present disclosure may include acoustic devices, such as transducers, probes, and hardware/software for their control. Systems consistent with the present disclosure may further include medical systems and devices, including all devices, systems, hardware, and software necessary to carry out any medical procedures that the fiber optical sensors are used to facilitate. It is understood that the fiber optical sensor structures described herein may be used for the measurement of both acoustic signals and other physical parameters, as described above, even if it is not explicitly stated for each individual embodiment. Further, it is understood that, in fiber optical sensor arrays discussed herein, optical sensor structures of differing sensitivities may be employed to enhance multidimensional sensing.

FIG. 1 illustrates an optical sensor system for use with a fiber optical sensor. As used herein, the term "fiber optical sensor" and the term "fiber based optical sensor" refer to optical sensors adapted and/or configured to detect acoustic signals, as described in further detail below. The optical sensor system 100A includes a light source 104, such as a laser, a light reception device 103, such as a photodetector, one or more optical waveguides 105, an optical circulator 102, and a fiber optical sensor 101. In operation, the light source 104 supplies the initial optical signal 111 to the fiber optical sensor 101 via the optical waveguides 105 and through the optical circulator 102. While an optical circulator 102 is discussed, optical components such as optical couplers may be used instead. The supplied initial optical signal 111 is returned by the fiber optical sensor 101 back along the optical waveguide 105. The returned optical signal 112 travels via the optical waveguides 105 through the optical circulator 102 and is received at the light reception device 103. As discussed above, acoustic signals incident on the fiber optical sensor 101 as well as other physical parameters may alter the optical characteristics (which may include the physical structure as well as the optical material properties) of the fiber optical sensor 101. Such optical characteristic alterations may be measured according to changes in the returned optical signal 112, as discussed in greater detail below.

Figure 2:
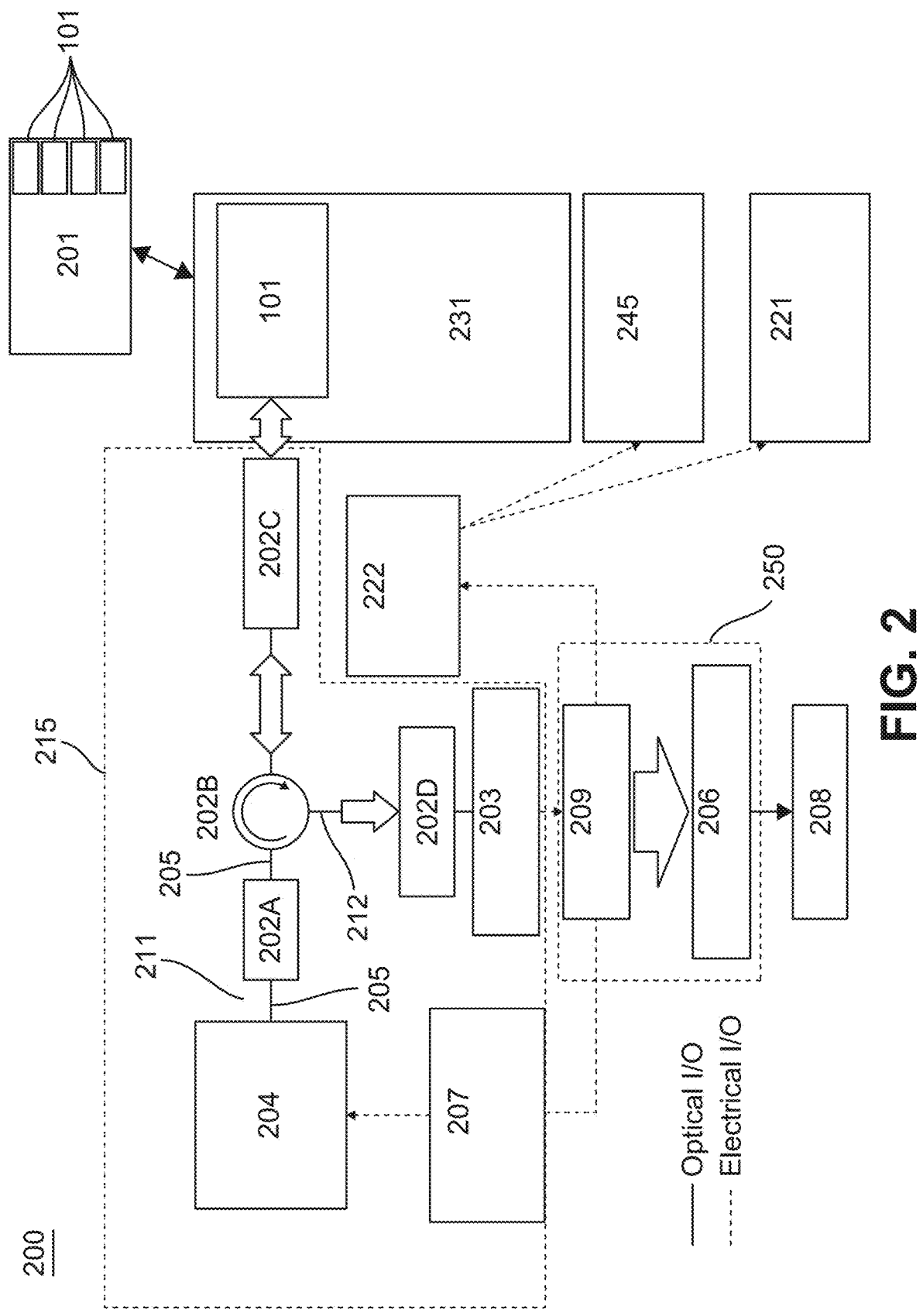
FIG. 2 illustrates an optical sensor system for use with a fiber optical sensor consistent with embodiments hereof.

FIG. 2 illustrates an optical acoustic sensor system for use with a fiber optical sensor. The optical acoustic sensor system 200 includes components, devices, hardware, and software to facilitate the use of a fiber optical sensor 101 or fiber optical sensor array 201 (comprising a plurality of fiber optical sensors 101, as pictured in FIG. 2). Further references to FIG. 2 may refer specifically to the use of a single fiber optical sensor 101; however, it will be understood that, in additional embodiments, a fiber optical sensor array 201 may be incorporated into the optical acoustic sensor system 200 in combination with any of the features discussed below and that any functionality attributed to a fiber optical sensor 101 may further be carried out by the fiber optical sensor array 201. In embodiments, the fiber optical sensor array 201 may include fiber optical sensors 101 having different sensitivities to one or more physical parameters, as discussed above. In embodiments, for example as shown in FIG. 2, the optical acoustic sensor system 200 may include hardware and componentry to facilitate the use of an ultrasound transducer and/or ultrasound probe. The ultrasound transducer may be used for generating and receiving acoustic signals or simply generating acoustic signals. The optical acoustic sensor system 200 may include a processing system 250, an optical sub-system 215, and an output device 208.

The processing system 250 may include a processing unit 209 and an image reconstruction or data unit 206. Processing unit 209 may include at least one computer processor, at least one non-transitory computer readable storage medium, and appropriate software instructions. The processing unit 209 is configured to provide control signals to and receive information signals from the light source control unit 207, the light receiving device 203, and the acoustic control unit 222. The processing unit 209 may communicate (via control signals and information signals) with the light source control unit 207, thereby providing control of optical signals provided to the fiber optical sensor 101. The processing unit 209 may communicate (via control signals and information signals) with the acoustic control unit 222, thereby providing control and reception of acoustic signals via an acoustic probe 245. The processing unit 209 is further configured to communicate with the light receiving device 203 to receive information signals associated with optical signals received by the light receiving device 203. Thus, processing unit 209 operates to provide the necessary control signals and receive the acquired information signals in the optical acoustic sensor system 200.

The processing unit 209 is further in communication with the image reconstruction or data unit 206, which operates to generate images based on the data and/or information acquired by the processing unit 209. The image reconstruction or data unit 206 may generate images based on data related to a medium, such as a human body, captured by the fiber optical sensor 101 and the acoustic probe 245. The medical device distal end 231 may include one or more of a needle, a catheter, a guidewire, a delivery device, a stylet, trocar, introducer, and/or any other device or apparatus configured for use within the body of a patient. The image reconstruction or data unit 206 may be integrated within a system containing the processing unit 209 and/or may be a separate system including at least one computer processor, at least one non-transitory computer readable storage medium, and appropriate software instructions. The processing system 250 may provide control signals to an output device 208 to provide a data output. The output device 208 may include, for example, a display or a device including a display.

In some embodiments, the processing unit 209 may alternatively or further include additional systems when one or more of the optical sensors is used for multi-dimensional sensing to detect multiple physical signals, such as temperature and pressure (e.g., to detect multiple different physical signals substantially simultaneously in real-time or near real-time). The measurement signals indicative of physical signals (e.g., temperature information and pressure information) may be determined and then transmitted, for example, to the display or another output device 208 for real-time monitoring or other data related to the measurement region. As used herein, "real-time" and "near real-time" may refer to uses where such data or information is provided continuously as it is measured, potentially with processing or other delays.

In some embodiments, the output device 208 may further include additional systems, such as a medical procedure system that is configured to use the data that is output. For example, output device 208 may include an endoscopy system, a laparoscopic system, a robotic surgical system, neurosurgical system and additionally may include an inter-operative ultrasound imaging system. The output data may include information about a location of the medical device distal end or working portion 231, physical parameters sensed, and images acquired of the medium in the area of where the medical device distal end 231 is used/deployed such as the patient anatomy, tissues, other medical tools/devices etc.

The optical sub-system 215 includes a light source control unit 207, a light source 204, optical devices 202A, 202B, 202C, and 202D, and light receiving device 203. The light source control unit is configured to interface with and control the light source 204 to control the production of an initial optical signal 211. The light source may generate a continuous wave (CW) or pulsed light emission (stimulated emission, spontaneous emission, and/or the like.) The initial optical signal 211 may include coherent light, e.g., laser light, provided in one or more modes and at one or more frequencies. The initial optical signal 211 may be of a single frequency/wavelength, a selection of frequencies/wavelengths, and/or a broadband light source. Thus, light source 204 may include a laser array configured to produce laser light in one or more modes and at one or more frequencies. Additionally, the polarization of the supplied light may be controlled to optimize the detected signal levels according to application requirement. The polarization state of light can be controlled to be linear polarized at certain angles or to be circularly polarized. Linearly polarized light will respond optimally to a certain input ultrasound direction, and circularly polarized light will respond to ultrasound from all directions. The polarization of light can be defined from the laser source output, and the output polarization state can be controlled by an in-line fiber polarizer, a paddle fiber polarization controller, an in-line fiber polarization controller, or other types of polarization controller. The optical devices 202A, 202B, and 202C may be configured to manipulate or influence the initial optical signal 211 received at the fiber optical sensor 101. The initial optical signal 211 may be provided at a plurality of wavelengths or across a spectrum of wavelengths. The optical device 202A may include, for example, a wavelength division multiplexing (WDM) device configured to multiplex multiple frequencies of initial optical signal 211 provided by the light source 204 for simultaneous transmission over the optical waveguides 205 that direct the initial optical signal 211 to the fiber end optical sensor 101. The optical device 202B may be a circulator with first, second and third ports, where the first port is in optical communication with the light source through a wavelength division multiplexing device (WDM) 202A. While an optical circulator 202B is discussed, optical components such as optical couplers may be used instead. The initial optical signal 211 may pass through a second optical device 202B, which may be an optical circulator, for example, and which is configured to direct the initial optical signal 211 to the optical device 202C. The optical device 202C may include a WDM device configured to de-multiplex the initial optical signal 211 provided to the fiber optical sensor 101, which may be part of an array 201 such that each of multiple fiber optical sensors 101 receives and subsequently outputs light of a different wavelength. Optical device 202C is in optical communication with the second port of the second optical device 202B for dividing the initial optical signal into optical signals each having one of the wavelengths associated therewith and combining the returned optical signals from the fiber optical sensor 101 which is then directed though a third port and optical device 202D which may include a WDM device, to the light receiving device 203.

The initial optical signal 211 is received by the fiber optical sensor 101 (or optical sensors 101 of the fiber optical sensor array 201 some embodiments) and returned through one or more optical waveguides 205 to the optical device 202C, which may be further configured to multiplex the returned optical signal 212 (if required) for transmission to the light receiving device 203. The returned optical signal 212 may be directed by the optical device 202C through the optical device 202B and towards the optical device 202D, which may be a WDM device configured to de-multiplex the returned optical signal 212 for reception by the light receiving device 203.

Optical device 202D may be in optical communication with the third port of the optical device 202B for receiving the returned optical signal and dividing it into individual wavelength components. The light receiving device 203, which may be a photodetector array, for example, may be in optical communication with optical device 202D for receiving the individual wavelength components of the returned optical signal, such that detected phase shifts or other changes in the individual wavelength components are indicative of sensed acoustic signals or other physical parameters.

It will be understood that, in embodiments that do not require frequency multiplexing/demultiplexing of the initial optical signal 211 and the returned optical signal 212, the optical devices 202A and 202C may not be required. The light receiving device 203 may include any suitable device configured to detect incident light, including, for example, a photodetector. The light receiving device 203 may further include, but is not limited to, a photodiode. The light receiving device 203 may be in optical communication with the optical device 202D (e.g., a wavelength division multiplexing splitter) for receiving the individual wavelength components of the returned optical signal 212, such that detected phase shifts, changes in polarization, or other changes in the individual wavelength components are indicative of sensed acoustic signals or other physical parameters. The changes in the returned optical signal 212 may be converted (e.g., by the processing unit 209 and/or by additional optical components such as polarization sensitive couplers and/or frequency shifters) into data representative of sensed acoustic signals or other physical parameters (which may be further used, e.g., to generate data representative of the tissue/anatomical structure of the medium in which the medical device distal end 231 is inserted in the area of a diagnostic or a therapeutic procedure and/or to identify a location of the medical device distal end 231 within the medium). In embodiments, the initial optical signal 211 and returned optical signal 212 signals may undergo pre-processing, beamforming and post-processing, as described in the following documents: U.S. application Ser. No. 18/032,953, filed Apr. 20, 2023 titled Image Compounding for Mixed Ultrasound Sensor Array; U.S. application Ser. No. 18/205,081, filed Mar. 7, 2023 titled Synthetic Aperture Imaging Systems and Methods Using Mixed Arrays; U.S. application Ser. No. 18/091,073, filed Dec. 29, 2022 titled Acousto-Optic Harmonic Imaging with Optical Sensors; PCT Application PCT/US2022/077762, filed Oct. 7, 2022 titled Ultrasound Beacon Visualization with Optical Sensors; PCT Application PCT/US2022/041250, filed Aug. 23, 2022 titled Multi-Dimensional Signal Detection with Optical Sensor; and PCT Application PCT/US2022/018515, filed Mar. 2, 2022 titled Acoustic Imaging and Measurements Using Windowed Nonlinear Frequency Modulation Chirp, each of which is incorporated herein by reference, disclose various methods for ultrasound beamforming and image processing. The image and/or data representative of the medical device distal end 231 (or the fiber optical sensor(s) 101) may then be displayed to the user on output device 208, which may include a computer display or the like. The image and/or data representative of the medical device distal end may further include the distal portion of the medical device in the insonified area.

As discussed above, the light receiving device 203 is in communication with the processing unit 209. The processing unit 209 receives information signals from the light receiving device 203 that are representative of the returned optical signal 212 received at the light receiving device 203. The processing unit 209 may also receive information signals from the light control unit 207 that are representative of the initial optical signal 211 output by the light source 204. The processing unit 209 operates to process the information signals associated with the returned optical signal 212 (optionally in comparison with the information signals associated with the initial optical signal 211) to make determinations about an acoustic environment and/or physical parameters at the fiber optical sensor 101, as discussed further below. Acoustic environment determinations may include the detection, identification, and interpretation of acoustic signals incident upon the fiber optical sensor 101 or sensors 101 of the fiber optical sensor array 201. Processing unit 209 may determine the presence and nature of acoustic signals incident upon the fiber optical sensors 101 of the fiber optical sensor 101. Physical parameter determinations may include having at least one sensor with a different acoustic sensitivity physical sensitivity (i.e., temperature or pressure) than another sensor and then detect, identify and interpret which physical stimuli is causing a signal shift.

Accordingly, the fiber optical sensors 101 may function to detect and/or receive acoustic (e.g., ultrasound) signals, and provide optical signals that are representative of and consistent with the acoustic signals or other physical parameters through an optical receive chain (e.g., optical devices 202C, 202B, 202D) to a light receiving device 203 configured to detect and/or receive the optical signals and provide electrical signals representative of and consistent with the optical signals to the processing unit 209 for processing and interpretation. Thus, the processing unit 209 may be configured to receive electrical signals that are representative of and consistent with the received acoustic signals and to process and interpret the electrical signals to reconstruct an image from the acoustic signals. An ultrasound image can be reconstructed using e.g., delay-and-sum beamforming principle (a common way of reconstructing an ultrasound image). In delay-and-sum beamforming, the spatial distribution of the ultrasound field amplitude in the volume of interest (area of image) is reshaped according to the delay timing between transmit, image pixel and receiver, and the received ultrasound signals are consequently recombined for the purpose of generating images. In delay-and-sum beamforming, the signals are coherently summed at each image pixel location according to the delay.

The processing unit 209 may further be configured to receive electrical signals that are representative of and consistent with the sensed physical parameters and to process and interpret the electrical signals to provide data or information related to the physical parameters, such as disclosed in PCT Application PCT/US2022/041250, filed Aug. 23, 2022 titled Multi-Dimensional Signal Detection with Optical Sensor, which is incorporated by reference.

The processing unit 209 may further be in communication with an acoustic control unit 222. The acoustic control unit 222 may be configured to provide control data to and receive signal data from the acoustic probe 245 and/or the acoustic transducers 221. The acoustic probe 245 may be configured for ex vivo or in vivo use and may include an AEG transducer or an array of AEG transducers (or any other suitable acoustic transducers) configured to generate and/or receive acoustic signals, such as ultrasound signals. The acoustic probe 245 may also include a mixed array of both AEG transducers (or any other suitable acoustic transducers) configured to generate and/or receive acoustic signals and optical sensors configured to receive optical sensors such as disclosed in US Patent Publications US2022/0365036, US2023/0097639; US2022/0350022, and US2023/0148869, each of which is incorporated herein by reference. The one or more array elements of the first type (e.g., AEG transducers) may be used to form a first image. In parallel, the one or more array elements of the second type (e.g., the optical sensors) are used to detect acoustic echoes that can be used to form a second image. The second image that is generated by highly sensitive and broadband optical sensors may be used independently or can be combined with the first image to form an even further improved image. Because of the high sensitivity and broad bandwidth of optical sensors, the image produced by the optical sensors may have improved spatial resolution, improved penetration depth, improved signal-to-noise ratio (SNR), improved tissue harmonic imaging, and/or improved Doppler sensitivity.

The acoustic transducers 221 may be a component of a medical device system that is configured for in vivo deployment within the medium where the diagnostic or therapeutic procedure is or will be performed. The acoustic transducers 221 may include endoluminal or endocavity transducers located on a catheter, cannula or the like, or may be an intraoperative transducer that may allow for transducer positioning during a minimally invasive procedure, such as on a laparoscopic tool, positioned on the end of a robotic arm or held by a surgeon, assistant, or any other medical personnel for selectively positioning. In embodiments, the acoustic transducers 221 may be disposed on a same medical device as the medical device distal end 231, e.g., along with the fiber optical sensor(s) 101. In embodiments, the acoustic transducers 221 may be disposed on one or more devices separate from that of the medical device distal end 231.

In vivo transducers 221 may be positioned on catheters/endoscopes/cannulas and transmit acoustic waves outward that insonify the region of interest in the medium and may be referred to as forward viewing probes, as is known in the art. Alternatively, the acoustic transducers 221 may emit acoustic waves to the side. For example, the transducers 221 may be part of side emitting phased array used in IVUS applications. In another example, the transducers 221 may be used in a guide catheter with two side by side lumens, one capturing the guidewire and one working lumen that does not extend as distally as the guidewire lumen. Further, the transducers 221 may radially transmit acoustic waves. For example, the transducers 221 may be included in an echoendoscope with a radial (or sector), linear, curvilinear (convex array), trapezoidal, or any other image format used in ultrasound imaging. A radial echoendoscope may provide circumferential views at rights angles to the shaft of the echoendoscope or in other words an image perpendicular to the insertion tube. Different ultrasound frequencies may be used to provide ultrasound imaging of distant and proximal structures. A radial echoendoscope may provide a 360-degree image of anatomy, which may be used in screening but may be limited for therapeutic applications, such as obtaining tissue samples. A curvilinear, linear or other appropriate array may be used for therapeutic applications, such as tissue or fluid sample collection, cyst drainage, biopsies of lesions/lymph nodes and injection for pain management. In embodiments, the transducers 221 may be incorporated in a curvilinear echoendoscope that visualizes in a range dependent upon the curvilinear radius and allows for real time insertion of needle/therapeutic device. In such an embodiment, the ultrasound view may be in the same line or plane as the scope shaft. In further embodiments, the transducers 221 may be incorporated in a transverse array and provide an image in a plane perpendicular to shaft of scope.

In further procedures, a moveable intraoperative transducer may be positioned on the end of a robotic arm or other tool (e.g., such as bk Medical Rob12C4) or simply held by the medical professional during the procedure. Further, certain cannulas and endoscopes may have a front-facing emitting transducer 221 for insonifying the region in front of the cannula, catheter, or scope such as a craniotomy transducer.

Typical ex vivo transducers 221 or probes 245 may be positioned on the patient's skin surface, such as commonly used for general imaging or for specific procedures, such as needle guidance, needle location determination, or needle placement.

The processing unit 209 is configured to use the information signals from the acoustic probe 245 or acoustic transducers 221 (as well as any other acoustic signal generator that may be connected to or in communication with the optical acoustic sensor system 200) as received by the fiber optical sensor 101 to sense, track, and monitor the medical device distal end 231 as well as generate ultrasound images of the anatomy in the area of the procedure and may provide data related to sensed physical parameters. In embodiments, the fiber optical sensor 101 or sensor array 201 operates to receive/detect acoustic signals generated by the acoustic probe(s) 245 and/or the acoustic transducers 221, along with scattered signals and tissue harmonics. Imaging of the medium may be accomplished by processing unit 209 according to differences between acoustic signals output or transmitted by the acoustic probe(s) 245 and/or acoustic transducers 221 and corresponding acoustic signals received and/or detected by the acoustic(s) probes 245 and/or acoustic transducers 221 and the fiber optical sensor 101. The signals detected may include the detected scattered signals and tissue harmonics. Portions of the medium through which the acoustic signals generated by the acoustic probe(s) 245 and/or acoustic transducers 221 travel may be imaged according to the detected acoustic signals.

The fiber optical sensor 101 (or sensor array 201) receives the acoustic signal transmitted from the acoustic probe 245 and/or acoustic transducers 221. Based on the signals received from the fiber optical sensor 101, the location of the fiber optical sensor 101 (and thus, the location of the medical device distal end 231) may be calculated either by triangulation (e.g., based on the receipt of one or more acoustic signals transmitted from a known origin) and/or by coherent image formation. More details can be found in co-pending application U.S. Provisional No. 63/522,994, titled Transponder Tracking and Ultrasound Image Enhancement, filed on Jun. 23, 2023 and U.S. application Ser. No. 18/382,984 titled Transponder Tracking and Ultrasound Image Enhancement filed on Oct. 23, 2023. The location of the fiber optical sensor 101 may be overlayed on an ultrasound image of the anatomy to determine the relative location of the fiber optical sensor 101 with respect to a known location of the acoustic probe 245 and/or acoustic transducers 221. Further, an ultrasound image of the surrounding anatomy may be coherently reconstructed according to a combination of acoustic signals received by the fiber optical sensor 101 and by one or more of the acoustic probe 245 and/or the acoustic transducers 221. Such a combination may produce a better image quality than an image formed using acoustic probes 245 and/or acoustic transducers 221 alone.

In embodiments for tracking, sensing, and monitoring the medical device distal end 231, the optical acoustic sensor system 200 may include a plurality of acoustic probes 245 that are either fixed in place or have their locations tracked. Tracking, sensing, determining, and monitoring the location and movement of the medical device distal end 231 may be accomplished, for example, by identifying timing and/or directional differences between a plurality of acoustic signals detected by the fiber optical sensor 101 and the acoustic transducer 221.

It will be understood that the configuration of the optical acoustic sensor system 200 as illustrated in FIG. 2 is provided by way of example. Different configurations may be employed without departing from the scope of this disclosure. For example, different arrangements of optical devices 202A/B/C/D, different numbers and arrangements of fiber optical sensors 101 and fiber optical sensor arrays 201 may be employed. In embodiments, the light source control unit 207 and the acoustic control unit 222 may be incorporated or integrated within the processing system 250. Additional combinations of the components of the optical acoustic sensor system 200 may be selected as appropriate to achieve the functionality as described herein.

Figure 3A:
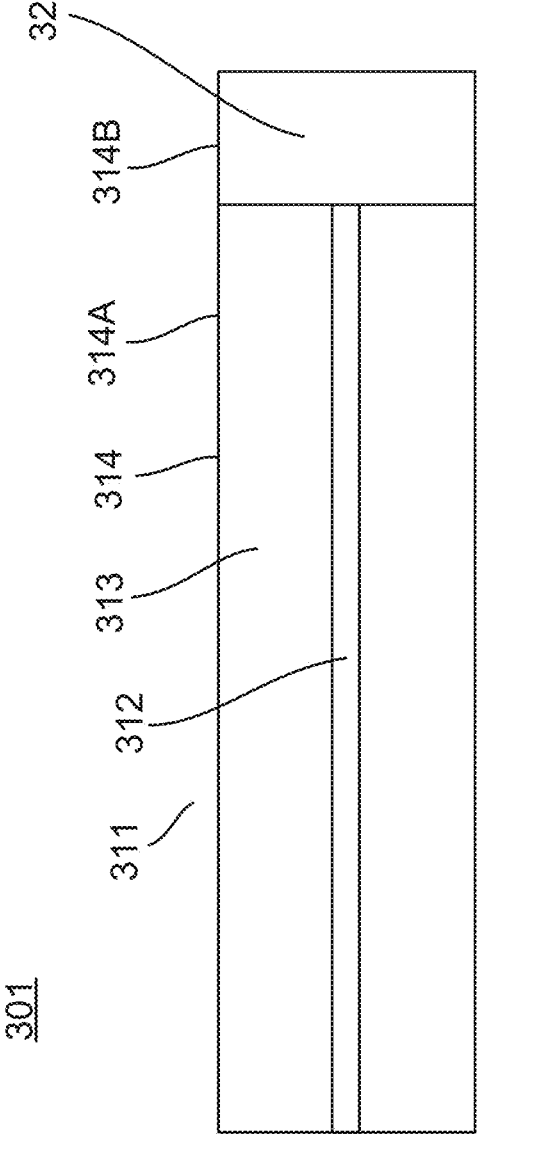
FIG. 3A illustrates a sensor fiber including a fiber optical sensor and associated optical fiber.

FIG. 3A illustrates a sensor fiber including a fiber optical sensor and associated optical fiber. An apparatus, as illustrated in FIG. 3A, may include a sensor fiber 301. The sensor fiber 301 may be an optical fiber configured with a fiber optical sensor disposed on an end thereof. Sensor fiber 301 includes an optical waveguide 311 comprising a core 312 and a cladding structure 313. The optical waveguide 311 is configured to transmit or carry light therein, e.g., within the core 312. The core 312 is surrounded by and protected by the cladding structure 313. The optical waveguide 311 may be substantially cylindrical along its length and/or may be of another suitable shape. The core 312 may be substantially in the center of the cladding structure 313. In embodiments, the optical waveguide 311 may be an optical fiber and may include any materials common to optical fibers. For example, core 312 may include silica glass, polymer, or other appropriate material. The cladding structure 313 material may be selected to be responsive to, for example, changes in ultrasound-induced pressure or strain. The pressure or strain induced by ultrasound will introduce a deformation or refractive index changes, leading to variations in optical signals passing through the optical fiber. When used as an ultrasound sensor, for example, the larger the variation, the higher the sensitivity and the better the detection limit. The cladding material may have at least one material property associated therewith, where the at least one material property may be a lower refractive index (RI) than a refractive index of the optical fiber core 312. Material properties such as the Young's modulus and photo-elastic coefficient of the fiber core, cladding materials, and encapsulating structures, which may be identical or different materials, can be tailored for the application. A smaller Young's modulus and larger photo-elastic coefficient may be preferred for increased ultrasound sensitivity and for acoustic responsiveness. As used herein, sensitive or responsive to acoustic signals may refer to materials that have a relatively small Young's modulus (E), a relatively high photo-elastic coefficient, and/or a relatively large refractive index (n), for example, as compared to silica materials. As used herein, a relatively small Young's modulus may refer to a Young's modulus less than 3.0 GPa, less than 2.0 GPa, less than 1.2 GPa, or within a range between 1.2 and 0.8 GPa. A relatively high photo-elastic coefficient C (i.e., $|C_1-C_2|$) may refer to photo-elastic coefficients greater than $C=2*10^{12}$ 1/Pa. A relatively large refractive index may refer to a refractive index greater than approximately 1.46 for optical signals that range between approximately 300 nm-2000 nm. Such materials may be selected to increase, improve, or optimize the ability of optical structures discussed herein to detect acoustic signals. Because the optical structures described herein are configured to detect acoustic signals (e.g., ultrasound signals), the materials of which they are constructed may be selected to maximize or increase the sensitivity of the optical properties of the structures with respect to incident acoustic signals. For example, a material with a lower Young's module requires less stress to deform. In some applications, increased deformation may be undesirable. However, increased deformation in response to incident acoustic signals may amplify or increase detectable changes in optical signals that pass through the optical structures experiencing greater deformation. Similarly, increases in the photo-elastic effect are desirable in optical structures as described herein, but may be undesirable in different structures configured for different purposes. As discussed above, materials may further be selected according to their sensitivity to other physical parameters, e.g., temperature.

It should be understood that the optical fiber core 312 may be any suitable type of optical fiber core, such as those made from silica, silicon, optically transparent polymers, or the like. As a non-limiting example, if the optical fiber core 312 is made from silica ($SiO_2$), the cladding material may be MY-133, a low refractive index optical coating manufactured by MY Polymers Ltd. of Israel, or BIO-133, also a low refractive index optical coating manufactured by MY Polymers Ltd. of Israel. As a further non-limiting example, if the core is silicon, which has a higher RI than silica, the cladding structure 313 may be polyvinylidene fluoride (PVDF), polystyrene (PS), parylene, benzocyclobutene (BCB), MY-133, or BIO-133.

The optical waveguide 311 may be configured for single mode (SM) transmission or for multi-mode (MM) transmission, depending upon the form factor and laser and sensor wavelength tuning requirements, as a SM fiber will be smaller in size. For example, a single mode fiber configured to operate in a 1550 nm band may have a 50 um cladding structure diameter and a core D=>4.2 um. Such a fiber may be a polarization maintaining fiber. A multimode fiber configured to operate in the 1550 nm band may have a core D=50 um-60.5 μm and a 125 um cladding diameter. In embodiments, a polymer fiber (e.g., PMMA, polystyrene) may be used. Such a fiber may have a larger diameter and a larger minimum bending radius than typical glass optical fibers. In other embodiments, a photonic crystal fiber (having a hollow structure/periodic pattern) may be used.

Disposed at an end (e.g., a distal end) of the sensor fiber 301 is an optical resonator structure 321. The present disclosure refers generally to fiber end sensors. Such fiber end sensors may include optical sensing structures such as optical resonator structure 321 disposed at an end (e.g., a distal end) thereof. The optical resonator structure 321 is coupled to the end of the optical waveguide 311 and may include an optical resonator, such as a Fabry-Perot (FP) resonator, whispering-gallery mode resonator, micro-ring, micro-toroid, spiral resonator, or a photonic crystal resonator integrated therein. The optical resonator structure 321 and other optical resonator structures described herein may include, in addition to the optical resonator, additional structures and components configured to facilitate the functionality of the optical resonator, as described below. The optical resonator is configured for receiving a first optical signal (e.g., light) supplied to it via the optical waveguide and providing a second optical signal back along the optical waveguide. The second optical signal may correspond to and represent an acoustic signal incident upon the optical resonator structure 321. As discussed above, the incident acoustic signal may cause physical deformation and/or material property alteration of the optical resonator structure 321. Accordingly, an optical signal provided along the optical waveguide 311 by the optical resonator structure may be altered by, influenced by, or otherwise indicative or representative of the acoustic signal and therefore may be used to characterize the incident acoustic signal.

The sensor fiber 301 may further comprise an encapsulating structure 314, which may include, for example, an outer coating, shielding, protective outer layer, and/or fiber jacket. The encapsulating structure 314 is configured with a first portion 314A surrounding the optical waveguide and 311 and a second portion 314B that at least partially surrounds the optical resonator structure 321. The encapsulating structure 314 may include a polymer, such as parylene, MY-133, BIO-133, or other suitable polymer that is sensitive or responsive to acoustic signals, as discussed above. The acoustic impedance of the encapsulating structure 314 may be selected to match an impedance of the optical resonator structure 321 so as to enhance the sensitivity of detection of acoustic signals. As used herein, "matching the impedance" may refer to selecting materials and/or structures that have acoustic impedances that match, generally it is well known to those of skill in medical ultrasound that acoustic impedances within 20% of one another provide an acceptable match. Closer matches in acoustic impedance lead to a better transmission of the acoustic signal (e.g., a smaller portion of the acoustic signal is reflected) and thus higher sensitivity. In embodiments, the first portion 314A surrounding the optical waveguide and 311 and a second portion 314B that at least partially surrounds the optical resonator structure 321 may comprise different materials selected for different purposes. For example, the first portion 314A may include an acoustically transmissive material, e.g., having an acoustic impedance selected to increase matching and thereby minimize reflection of acoustic signals. The second portion 314B may include acoustically responsive/sensitive materials, as discussed above, to increase a response to an incident acoustic signal in the area of the optical resonator structure 321. Unless explicitly stated otherwise, all encapsulating structures discussed herein may include properties similar to those of encapsulating structure 314, including a first portion and a second portion comprising different materials selected for different purposes.

The optical resonator structure 321 is disposed at an end of the optical waveguide 311 and may therefore be referred to as a fiber-end sensor. The cladding structure 313 may have a first diameter and the optical resonator structure 321 may have a second diameter. The first diameter and the second diameter may or may not be substantially the same. Depending on the application, it may be advantageous to have the fiber substantially the same size or to have a significantly larger sensor than the fiber, such as a bulb like structure that may or may not be symmetrical. The increased size may further enhance the acoustic sensitive surface area of the sensor, increasing the overall sensitivity. As discussed above, the sensor fiber 301 may be compact as may be needed in view of the small form factor needed for certain medical applications, in some examples, wherein the first diameter and/or the second diameter are less than 200 microns, less than 175 microns, less than 150 microns, less than 130 microns, less than 100 microns, or less than 85 microns.

Figure 3B:
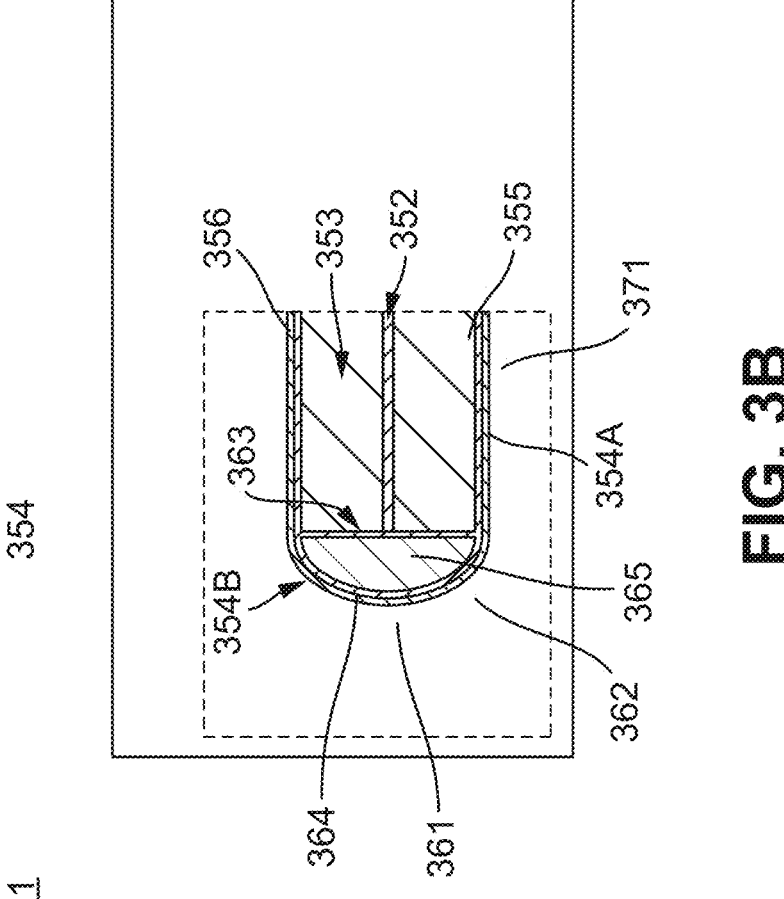
FIG. 3B illustrates a sensor fiber including an optical waveguide and optical resonator structure having a Fabry-Perot resonator as an optical sensor.

FIG. 3B illustrates a sensor fiber including an optical waveguide and optical resonator structure having a Fabry-Perot type resonator as an optical sensor. Sensor fiber 351 is an example of sensor fiber 301 and may include any of the features of sensor fiber 301 as described above. Sensor fiber 351 includes an optical waveguide 371 having a core 352 and a cladding structure 353. The core 352 may have a diameter in a range between 7 and 12 microns or a diameter of approximately 9 microns. These dimensions are provided as an example only and do not limit the sizes and diameters encompassed by embodiments of the present disclosure. The sensor fiber 351 may include an encapsulating structure 354, which may, for example, include an outer coating, protective outer layer, and/or fiber jacket, that encapsulates both the optical waveguide 371 and an optical resonator structure 361 disposed at an end of the optical waveguide 371. The encapsulating structure 354 may be a multi-layer structure, including, for example, an inner layer 355 and an outer layer 356. The inner layer 355 may include gold or any suitable reflective material layer for the optical wave while the outer layer 356 may include parylene, MY-133, BIO-133, or other suitable protective layer that may be acoustically transparent. The encapsulating structure 354 may include a first portion 354A that encapsulates or surrounds the optical waveguide 371 and a second portion 354B that encapsulates or surrounds the optical resonator structure 361. The encapsulating structure 354 may have features similar to those of encapsulating structure 314, including a first portion and a second portion of different materials. The optical resonator structure 361 may be configured with a Fabry-Perot resonator as an optical resonator 362. The optical resonator 362 includes a distal reflecting surface 364 and a proximal reflecting surface 363 arranged at either side of an optical cavity 365. The distal reflecting surface 364 and the proximal reflecting surface 363 may be constructed of any suitable reflective material. As shown in FIG. 3B, the distal reflecting surface 364 and the proximal reflecting surface 363 are formed from and integral with the inner layer 355 of the encapsulating structure 354, and are thus formed of gold or other suitable reflective material. As illustrated in FIG. 3B, the distal reflecting surface 364 may be curved and the proximal reflecting surface 363 may be substantially flat. This arrangement is by way of example only, and the distal and proximal reflecting surfaces 364/363 may be arranged with different shapes and/or configurations. Some additional examples are provided in FIGS. 4A-4E. In other embodiments, the distal reflecting surface 364 and the proximal reflecting surface 363 may be formed from different materials and/or may be structures separate from the encapsulating structure 354. The optical cavity 365 is disposed between the distal reflecting surface 364 and the proximal reflecting surface 363. The term "optical cavity," as used herein, refers to a volume occupied by a material that provides minimal attenuation to light passing therethrough (e.g., having a high Q factor typically higher than 1000). The quality (Q) factor is a dimensionless parameter that describes the amount of damping within a resonator. A higher Q factor corresponds to a more sensitive resonator.

In optics, the Q factor of a resonant cavity is given by:

$$Q = 2\pi f_0 E/P,$$

where $f_0$ is the resonant frequency, E is the stored energy in the cavity, and $P=-dE/dt$ is the power dissipated. The optical Q factor is equal to the ratio of the resonant frequency to the bandwidth of the cavity resonance. The average lifetime of a resonant photon in the cavity is proportional to the cavity's Q factor. Thus, a high Q factor represents low damping, with a high lifetime for a photon within the cavity.

The Q factor, as well as any other determinations of sensitivity and responsiveness, are ultimately limited by the choice of material used for the optical fiber core. A conventional Fabry-Pérot interferometer may be formed uniformly from a single material, such as silica throughout the entire structure. Although silica, for example, has excellent optical transmission capabilities, it does not have equally exceptional acoustic sensitivity. Although numerous materials with superior acoustic sensitivity are known, such materials, on their own, may not make suitable replacements for silica and the like for optical fiber cores. The present invention adapts resonant actuators to take advantage of the acoustic sensitivity found in other materials.

The optical cavity 365 may be composed of a suitable material, such as a polymer. Polymer materials, such as MY-133 or BIO-133, with high acoustic transmissivity may be employed to enhance the sensitivity of the optical resonator structure, as discussed above. The optical resonator structure 361 may be configured to detect acoustic signals. Acoustic signals incident upon the optical resonator structure, e.g., upon the distal reflecting surface 364, the proximal reflecting surface 363, and/or the optical cavity 365 may cause vibrations and/or other physical deformations of these structures, which may alter or influence their optical properties. Further, due to the photo-elastic effect, the material properties of these structures may be altered and thus further change the optical properties. Accordingly, return optical signals provided to the optical waveguide 371 by the optical resonator structure 361 (e.g., in response to optical signals supplied via the optical waveguide 371) may be indicative of or representative of the acoustic signals incident upon the optical resonator structure 361. More particularly, detected phase shifts of the light in the sensor beam, are indicative of sensed acoustic signals. With a polarization based sensor, a polarization analyzer will interpret the phase shift/delays between the different polarization components in order to generate the signal indicative of the sensed acoustic signals. As discussed above, the optical resonator structure 361 may be further configured to detect additional physical parameters.

Figures 4A, 4B, 4C, 4D, 4E:
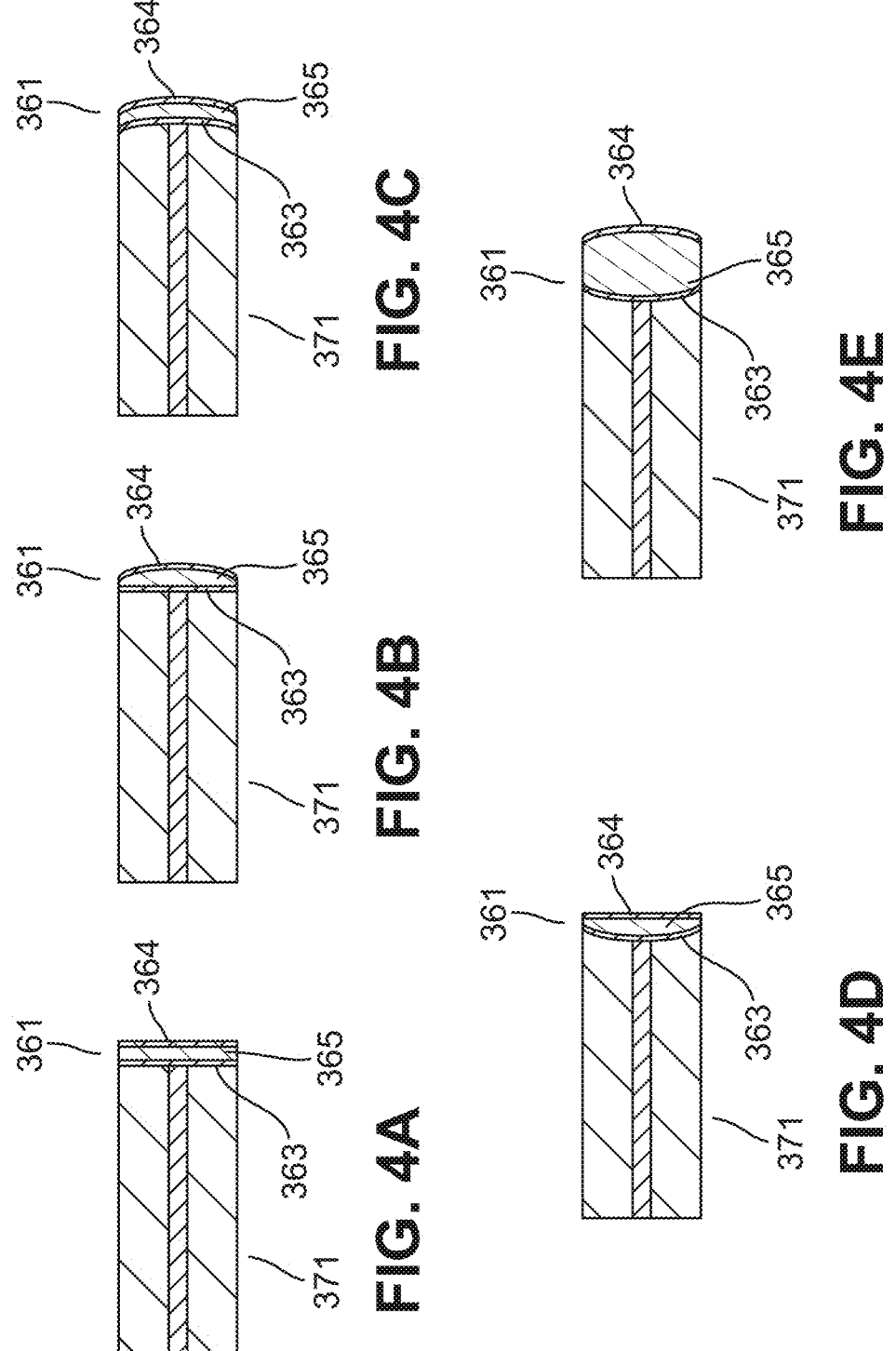
FIG. 4A-FIG. 4E illustrate several variations of the optical resonator structure consistent with embodiments hereof.

FIG. 4A-FIG. 4E illustrate several variations of the optical resonator structure 361 consistent with embodiments hereof. FIG. 4A illustrates an optical resonator structure 361 having a proximal reflecting surface 363 and a distal reflecting surface 364 that are substantially flat and substantially parallel at either end of an optical cavity 365 that is substantially cylindrical. FIG. 4B illustrates an optical resonator structure 361 having a proximal reflecting surface 363 that is substantially flat and substantially square to the optical waveguide 371 and a concave distal reflecting surface 364 with respect to the optical cavity 365. FIG. 4C illustrates an optical resonator structure 361 having a proximal reflecting surface 363 that is convex with respect to the optical cavity 365 and a distal reflecting surface 364 that is concave with respect to the optical cavity. FIG. 4D illustrates an optical resonator structure 361 having a proximal reflecting surface 363 that is concave with respect to the optical cavity 365 and a distal reflecting surface 364 that is substantially planar and substantially square to the optical waveguide 371. FIG. 4E illustrates an optical resonator structure 361 having a proximal reflecting surface 363 and a distal reflecting surface 364 that are both concave with respect to the optical cavity 365.

Figures 5A, 5B:
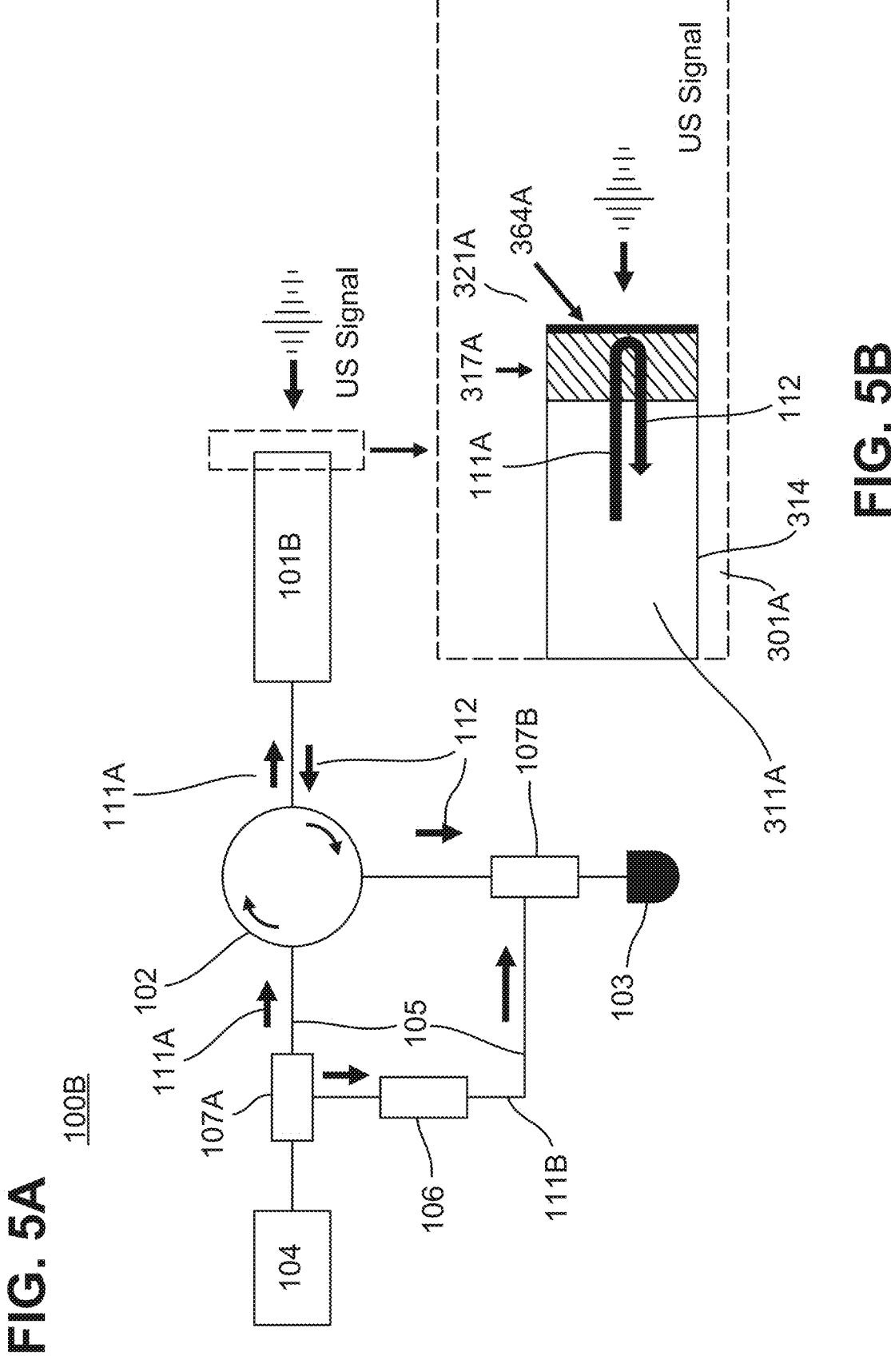
FIGS. 5A and 5B illustrate examples of an optical sensor system and fiber optical sensor consistent with embodiments hereof.

FIG. 5A illustrates an optical sensor system for use with a fiber optical sensor according to embodiments herein. FIG. 5B illustrates an interferometer based optical sensor according to embodiments herein. The optical sensor system 100B of FIG. 5A is configured for use with an interferometer based fiber optical sensor 101B, as shown in FIG. 5B.

The fiber optical sensor 101B may include a fiber end sensor having an interferometer based acoustic sensor. The fiber optical sensor 101B may include a sensor fiber 301A having an interferometer based fiber-end sensor structure 321A disposed at an end thereof, e.g., at the end of an optical waveguide 311A. Except where noted, the sensor fiber 301A may include features and structures consistent with those of sensor fiber 301. The interferometer based fiber-end sensor structure 321A may include, for example, a Mach-Zehnder (MZ) type of interferometer. The interferometer based fiber-end sensor structure 321A is coupled to the end of the optical waveguide 311A. The interferometer based fiber-end sensor structure 321A may include additional structures and components configured to facilitate the functionality of the interferometer based fiber-end sensor, as described below. The interferometer based fiber-end sensor is configured for receiving a first optical signal (e.g., light) supplied to it via the optical waveguide 311A and providing a second optical signal back along the optical waveguide 311A. The second optical signal may correspond to and represent an acoustic signal incident upon the interferometer based fiber-end sensor structure 321A. The incident acoustic signal may cause physical deformation and/or material property alteration of the interferometer based fiber-end sensor structure 321A. Accordingly, an optical signal provided along the optical waveguide 311A by the interferometer based fiber-end sensor structure 321A may be altered by, influenced by, or otherwise indicative or representative of the acoustic signal and therefore may be used to characterize the incident acoustic signal.

The interferometer based fiber-end sensor structure 321A may include an acoustically responsive polymer portion 317A including parylene or other suitable polymer that is sensitive to acoustic signals and/or other physical parameters. The acoustic impedance of the polymer portion 317A may be selected to match (e.g., within 1%, 5%, 10%, or 20%) of the acoustic impedance of an encapsulating structure of the sensor fiber 301A to enhance the sensitivity of the fiber-end sensor structure 321A, as described above. A distal reflecting surface 364A is arranged at the distal end of the fiber-end sensor structure 321A and may be constructed of any suitable material, for example, gold. As shown in FIG. 5B the distal reflecting surface 364A is formed from gold and integral with polymer portion 317A.

The fiber-end sensor structure 321A is disposed at an end of the optical waveguide 311A and may therefore be referred to as a fiber end sensor. The optical waveguide 311A may have a first diameter and the fiber end sensor structure 321A may have a second diameter. The first diameter and the second diameter may be substantially the same and/or may have a ratio in a range between 1.05 and 0.95, a ratio in a range between 1.02 and 0.98, or a ratio in a range between 1.01 and 0.99. As discussed above, the sensor fiber 301A may be compact, e.g., wherein the first diameter and/or the second diameter are less than 200 microns, less than 175 microns, less than 150 microns, less than 130 microns, less than 100 microns, or less than 85 microns.

The optical sensor system 100B is configured for use with an interferometer based fiber optical sensor 101B. The optical sensor system 100B may include a light source 104, such as a laser, a light reception device 103, such as a photodetector, one or more optical waveguides 105, an optical circulator 102, one or more frequency shifters 106, and one or more couplers 107A/B. In operation, the light source 104 supplies the initial optical signal 111A to the fiber optical sensor 101 via the optical waveguides 105, through a coupler/decoupler 107A, and through the optical circulator 102. The supplied initial optical signal 111A is returned by the fiber optical sensor 101 back along the optical waveguide 105. The returned optical signal 112 travels via the optical waveguides 105 through the optical circulator 102 and a coupler/decoupler 107B and is received at the light reception device 103. The coupler/decoupler 107A serves to direct a portion of the initial optical signal 111A through the frequency shifter 106 as reference optical signal 111B to the coupler/decoupler 107B where it may be combined with the returned optical signal 112 for detection and comparison at the light reception device 103. As discussed above, acoustic signals incident on the fiber optical sensor 101 alter the optical characteristics (including the physical structure as well as the optical material properties) of the fiber optical sensor 101. Such optical characteristic alterations may be measured according to changes in the returned optical signal 112 as compared to the reference optical signal 111B. Further, physical parameter changes (e.g., temperature and pressure changes) may also alter the optical characteristics in a manner that can be measured.

Figures 5C, 5D:
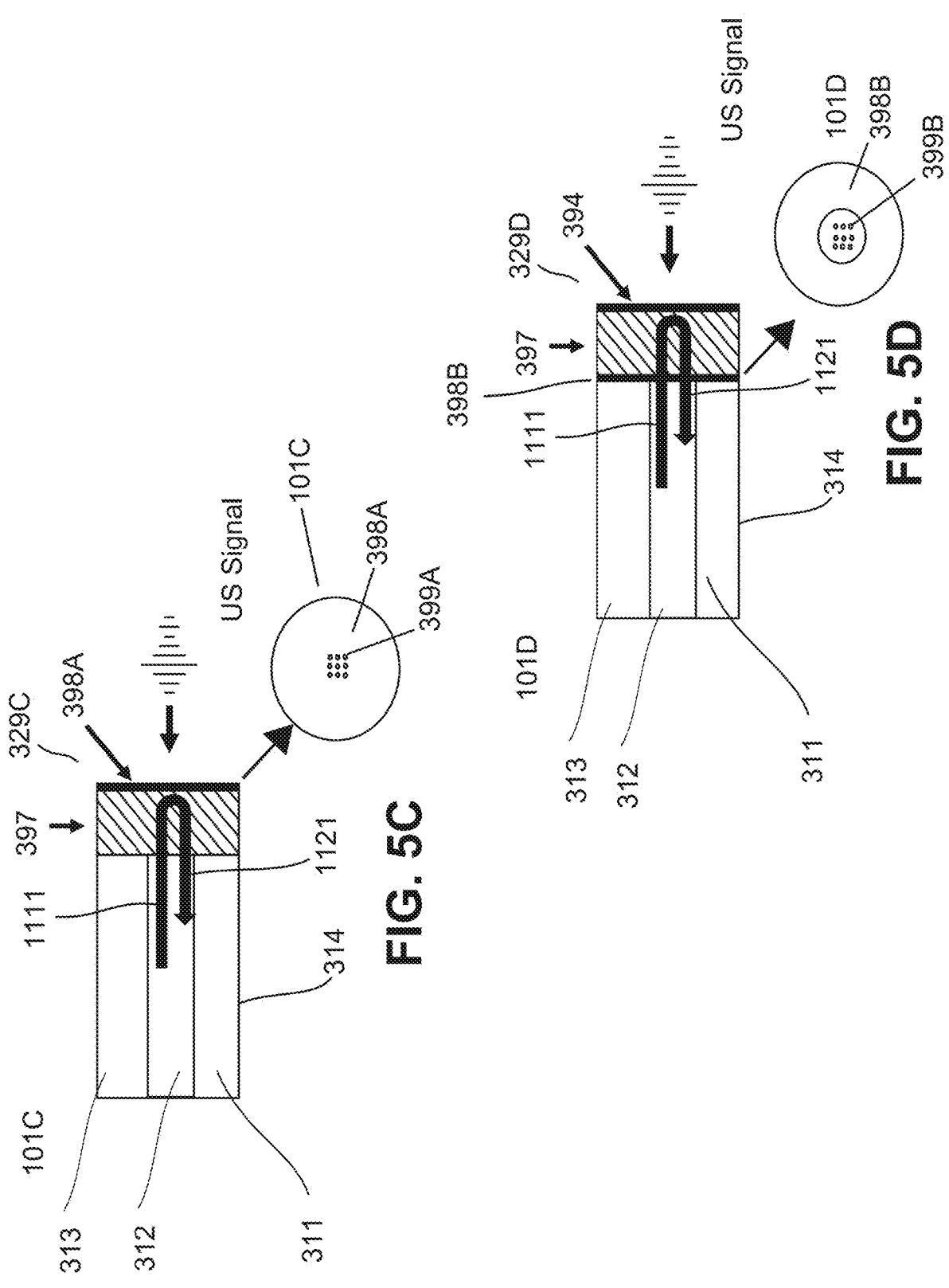
FIGS. 5C and 5D illustrate examples of an optical sensor system and fiber optical sensor consistent with embodiments hereof.

FIGS. 5C and 5D illustrate embodiments of fiber optical sensors that include fiber end facets configured to provide or enhance acoustic detection capabilities. Fiber optical sensor 101C and fiber optical sensor 101D each include at least an optical waveguide 311, a fiber core 312, a cladding structure 313, and an encapsulating structure 314. The fiber optical sensor 101C includes an optical sensor structure 329C that includes an acoustically responsive polymer portion 397 and a facet substrate 398A located at a distal end thereof. The fiber optical sensor 101D includes an optical sensor structure 329D that includes that includes an acoustically responsive polymer portion 397, a facet substrate 398B disposed between the polymer portion 397 and the core 312 and cladding structure 313, and a distal end reflective surface 394 disposed at a distal end of the polymer portion 397.

In the fiber optical sensor 101C, the facet substrate 398A is disposed at a distal end of the fiber optical sensor 101C. The optical sensor structure 329C is formed by the polymer portion 397 and the facet substrate 398A. The facet substrate 398A includes one or more facet structures 399A, as shown in the cross-sectional view. The facet structures 399A may include acoustically responsive microstructures, such as metasurfaces including patterns of small elements arranged to change the wavefront shape of the acoustic signals and maximize the detection of acoustic signals, acoustically responsive low-dimensional materials with optomechanical features selected to optimize acoustic response, e.g., features that are more prone to deformation when receiving acoustic signals, exhibit greater material responses to acoustic signals, and plasmonic structures patterned to amplify light-matter interactions, as described herein. Plasmonic structures may locally amplify incident light due to their plasmonic resonance. The facet structures 399A operate as an optical sensor as described herein. During operation, the supplied optical signal 1111 reflects off of the facet substrate 398A and is returned to the system as the returned optical signal 1121. Because the facet structures 399A are acoustically responsive, the returned optical signal 1121 is modified by changes in the facet structures 399A caused by incident acoustic signals. In embodiments, plasmonic resonance induced in a plasmonic meta-surface serving as the facet structures 399A or Mie resonance induced in a dielectric meta-surface serving as the facet structures 399A may be altered (e.g., shifted) by incident acoustic signals to provide detectable modifications in the returned optical signal 1121. The returned optical signal 1121 may then be interpreted by any of the systems described herein.

In the fiber optical sensor 101D, the facet substrate 398B is disposed between the polymer portion 397 and core 312 and cladding structure 313. The optical sensor structure 329D is formed by the polymer portion 397, the facet substrate 398B, and the distal reflective surface 394. The facet substrate 398B includes one or more facet structures 399B, as shown in the cross-sectional view. The facet structures 399B may include acoustically responsive microstructures similar to those described above with respect to facet structures 399A. The facet structures 399B operate to enhance, improve, or otherwise modify the acoustic response of the optical sensor structure 329D. During operation, the supplied optical signal 1111 reflects off of distal reflective surface 394 and is returned to the system as the returned optical signal 1121. The polymer portion 397 and the distal reflective surface 394 are acoustically responsive and the returned optical signal 1121 is modified according to acoustic signals incident upon these structures. Because the facet structures 399B are acoustically responsive and both the supplied optical signal 1111 and the returned optical signal 1121 pass through the facet substrate 398B, the returned optical signal 1121 is further modified by changes in the facet structures 399B caused by incident acoustic signals. In embodiments, the facet structures 399B may be designed and/or selected to optimize coupling (e.g., decrease signal loss) and/or achieve critical coupling (e.g., eliminate signal loss) for the optical sensor structure 329D. Increased coupling in the optical sensor structure 329D serves to increase the amplitude of optical signals responsive to incident acoustic signals. Thus, the returned optical signal 1121 may exhibit a higher signal to noise ratio. Further, incident acoustic signals that cause deformation in the facet structures 399B may also server to alter the degree to which the facet structures 399B modify the coupling in the optical sensor structure 329D, thus providing another aspect of returned optical signal 1121 that is altered by incident acoustic signals for interpretation. The returned optical signal 1121 may then be interpreted by any of the systems described herein. Accordingly, the facet substrate 398B may serve to enhance, improve, or otherwise modify the acoustic response of the optical sensor structure 329D.

The facet structures 399A and 399B are illustrated in FIGS. 5C and 5D as being incorporated into fiber optical sensors 101C and 101D. Such facet substrates are not limited to use with optical sensors having the interferometer based structure and operation of fiber optical sensors 101C and 101D and may be incorporated into any of the fiber optical sensors discussed herein.

Figures 5E, 5F:
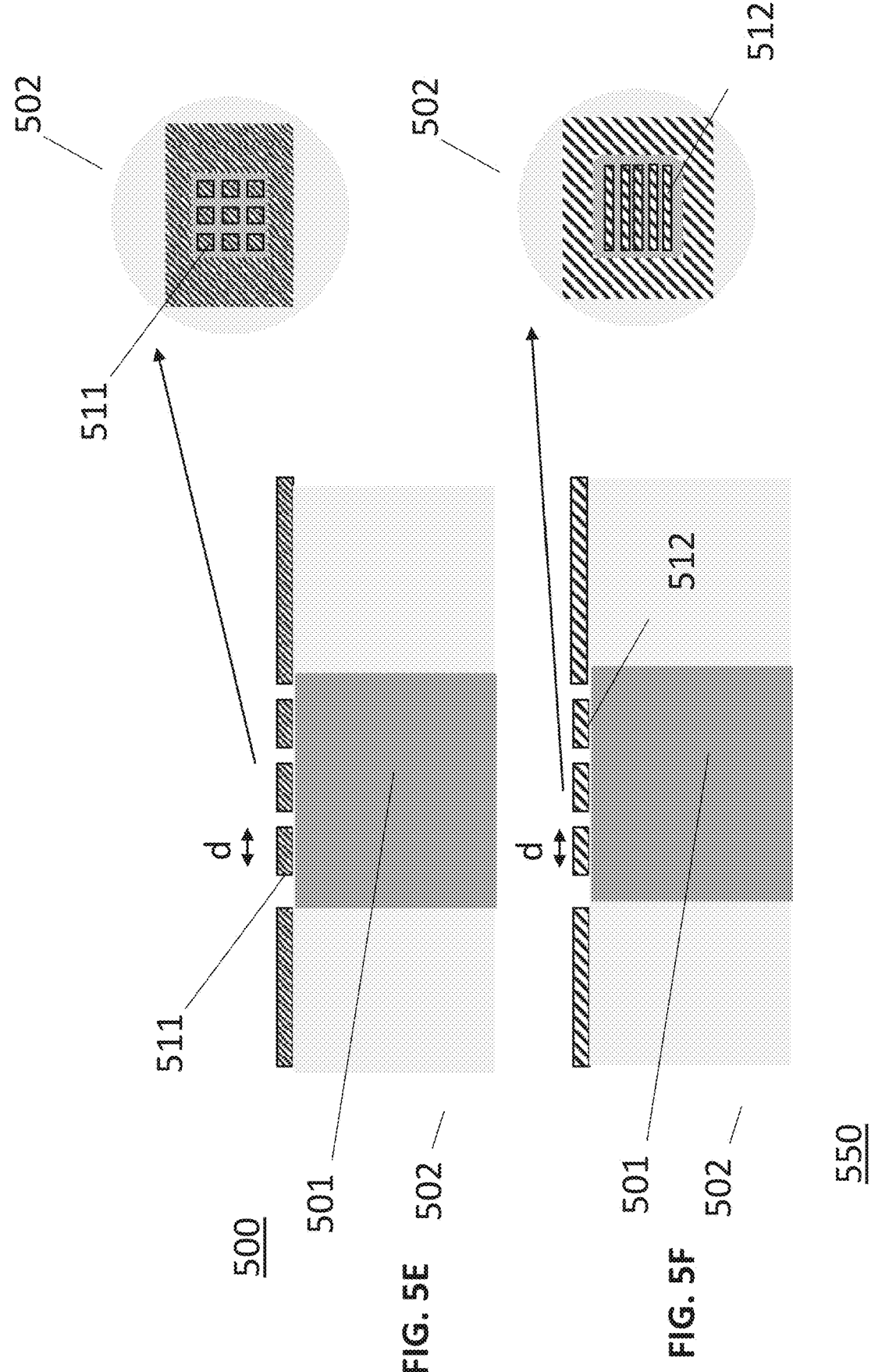
FIGS. 5E and 5F illustrate examples of micro facet structures consistent with embodiments hereof.

FIG. 5E illustrates an example of plasmonic meta-surfaces and FIG. 5F illustrates an example of dielectric meta-surfaces. As illustrated in FIG. 5E, a fiber 500 may include plasmonic meta-surfaces 511 disposed at an end of an optical waveguide 502 having a core 501. The plasmonic meta-surfaces 511 may be disposed on the end of the fiber 500 within the area defined by the core 501. As illustrated, the plasmonic meta-surfaces 511 may be disposed in a pattern of squares, for example, or may also be disposed in any other suitable pattern. The plasmonic meta-surfaces 511 may exhibit plasmonic resonance when struck by an optical signal from the core 501. Deformations caused by incident acoustic signals alter the plasmonic resonance and permit detection and decoding of the acoustic signal as discussed herein. The plasmonic meta-surfaces 511 may include various metals and in particular may include noble metals, such as gold. Further the plasmonic meta-surfaces 511 may be thin film surfaces, having a height less than 50 microns, less than 40 microns, less than 30 microns, less than 20 microns, or less than 10 microns. In further embodiments, the plasmonic meta-surfaces 511 may be low dimensional or two dimensional surfaces, having a height less than 1 micron. In the lateral dimension, the features of the plasmonic meta-surfaces 511 may be small, having lateral dimensions D (e.g., width and/or length) less than the wavelength of optical signals used by the sensors (e.g., less than 600 nanometers, less than 400 nanometers, less than 200 nanometers, etc.) Lateral dimensions of the plasmonic meta-surface 511 features may also refer to spacing between the features. FIG. 5F illustrates dielectric meta-surfaces 512, which may be similarly disposed within the area of a fiber core 501 at the end of an optical waveguide 502 of a fiber 550. The dielectric meta-surfaces 512 may be arranged in strips or rectangles, as illustrated in FIG. 5F, or in any other suitable shape. The dielectric meta-surfaces 512 may be configured to exhibit Mie resonance when struck by an optical signal. The Mie resonance may be altered by an incident acoustic signal, thereby permitting the detection and decoding of the acoustic signal. In embodiments, the dielectric meta-surfaces 512 may include dielectric materials, such as Silicon, Titanium Oxide, etc. In embodiments, the dielectric meta-surfaces 512 may be sized similarly to the plasmonic meta-surfaces 512, as discussed above.

Figures 6A, 6B:
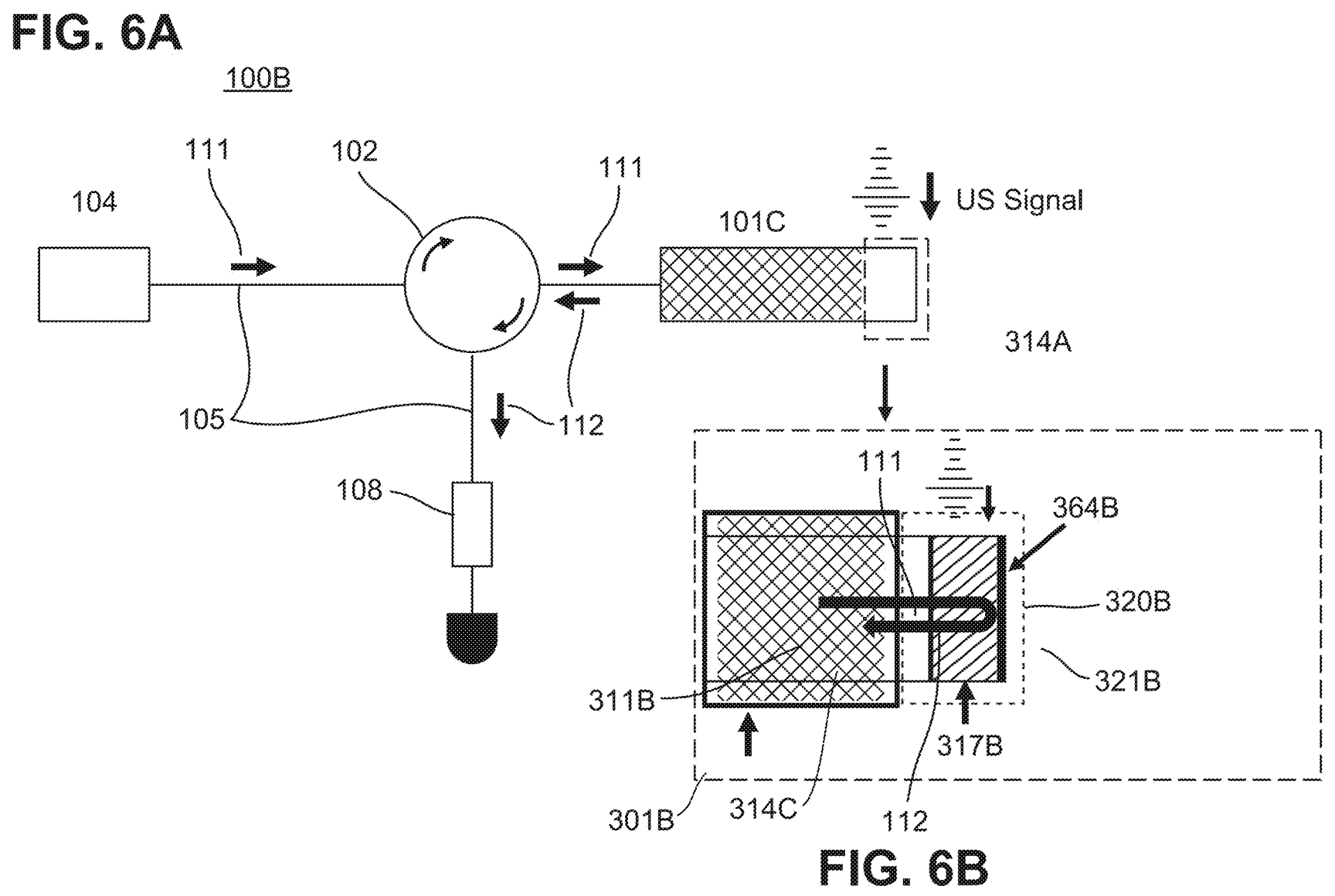

FIG. 6A illustrates an optical sensor system for use with a fiber optical sensor according to embodiments herein. FIG. 6B illustrates a polarization based optical sensor according to embodiments herein. The optical sensor system 100B is configured for use with a polarization based fiber optical sensor 101C. The fiber optical sensor 101C may include a fiber end sensor having a polarization based acoustic sensor. The fiber optical sensor 101C may include a sensor fiber 301B having a polarization based fiber-end sensor structure 321B disposed at an end thereof, e.g., at the end of an optical waveguide 311B. In further embodiments, as discussed below, the polarization based fiber-end sensor structure 321B may be disposed at any location along the sensor fiber 301B. Except where noted, the sensor fiber 301B may include features and structures consistent with those of sensor fiber 301. The sensor fiber 301B includes an encapsulating structure 314C, which may include, for example, an outer coating, protective outer layer, and/or fiber jacket. The encapsulating structure 314C may include a material selected to have a relatively high acoustic impedance mismatch with the cladding structure of the sensor fiber 301B. Accordingly, where the sensor fiber 301B is covered by the encapsulating structure 314C, incident acoustic signals may be reflected. The polarization based fiber-end sensor structure 321B may be exposed by a window 320B defined by a lack of encapsulating structure 314C and may include a polymer portion 317B comprising an acoustically responsive polymer and a distal reflective surface 364B configured to reflect the initial optical signal 111 as a reflected optical signal 112. The polarization based fiber-end sensor structure 321B is configured for receiving a first optical signal (e.g., light) supplied to it via the optical waveguide 311B and providing a second optical signal back along the optical waveguide 311B. The second optical signal may correspond to and represent an acoustic signal incident upon the polarization based fiber-end sensor structure 321B. The incident acoustic signal may cause physical deformation and/or material property alteration of the polarization based fiber-end sensor structure 321B. Accordingly, an optical signal provided along the optical waveguide 311B by the polarization based fiber-end sensor structure 321B may be altered by, influenced by, or otherwise indicative or representative of the acoustic signal and therefore may be used to characterize the incident acoustic signal. In the polarization based fiber-end sensor structure 321B, the incident acoustic signal cause stress in the polymer portion 317B that results in one or more of birefringence and a rotation of the polarization of the light passing through the polymer portion 317B changes in the polarization of the light carried by the optical waveguide 311B, which may be detected and analyzed by the optical sensor system 100B as discussed below. In embodiments, the polarization based fiber optical sensor 101C (and all polarization based sensors discussed and described herein), may be further configured to detect, identify, and/or senses physical parameters, such as pressure and temperature, as described herein.

The optical sensor system 100B includes a light source 104, such as a laser, a light reception device 103, such as a photodetector, one or more optical waveguides 105, an optical circulator 102, and a fiber optical sensor 101B. In operation, the light source 104 supplies the initial optical signal 111 to the fiber optical sensor 101B via the optical waveguides 105 and through the optical circulator 102. The supplied initial optical signal 111 is returned by the fiber optical sensor 101B back along the optical waveguide 105. The returned optical signal 112 travels via the optical waveguides 105 through the optical circulator 102, through the polarization analyzer 108, and is received at the light reception device 103. Use of the polarization analyzer 108 permits the determination of the polarization difference between the initial optical signal 111 and the returned optical signal 112. As discussed above, acoustic signals incident on the fiber optical sensor 101B alter the optical characteristics (including the physical structure as well as the optical material properties) of the fiber optical sensor 101B and cause an alteration in the polarization of the returned optical signal 112. Such polarization changes may be measured according to differences in the returned optical signal 112 and the initial optical signal 111 as determined according to the photodetector.

Figure 6C:
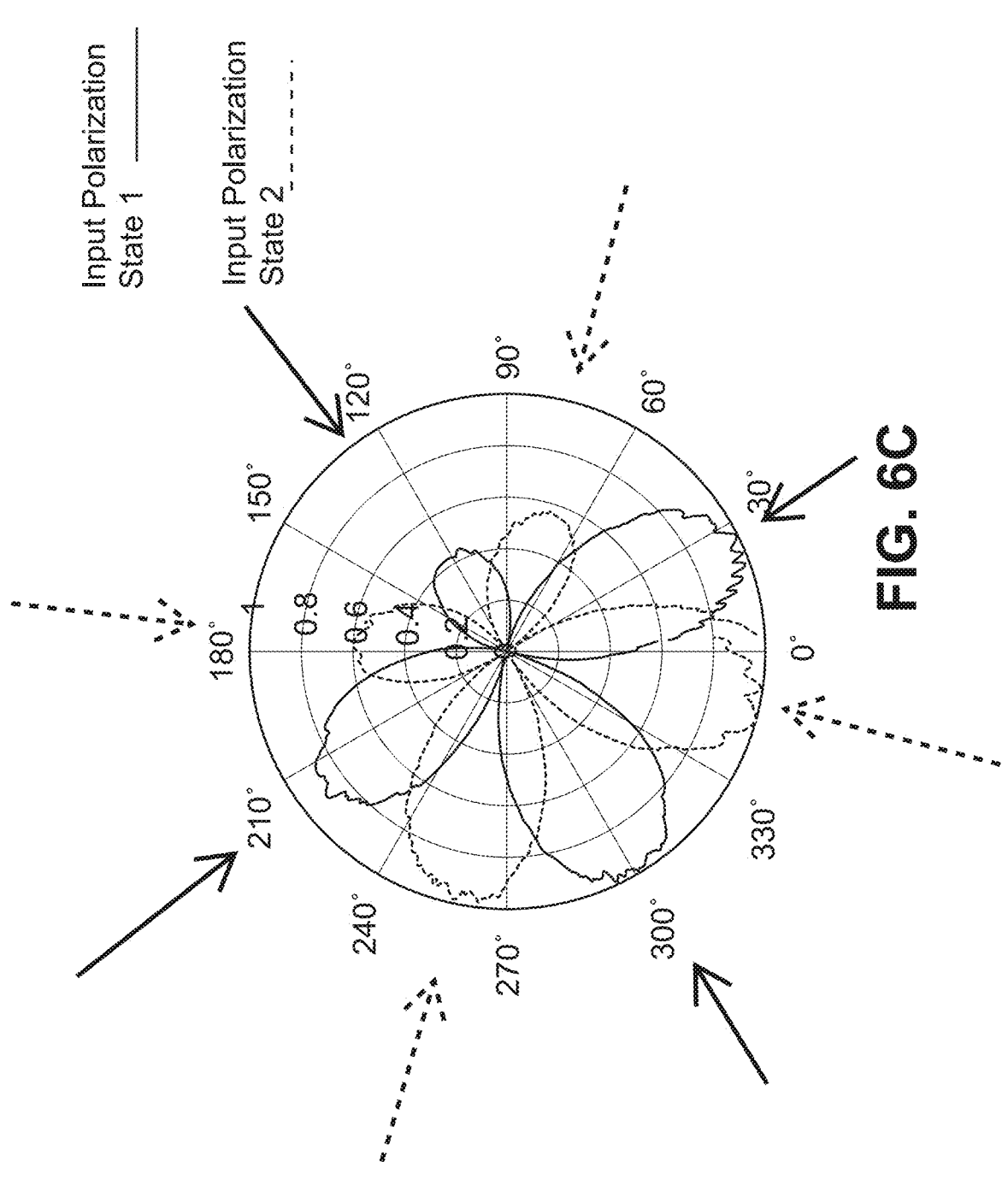

In embodiments, the angular sensitivity of the polarization based fiber-end sensor structure 321B may be subject to differences in the polarization of the initial optical signal 111. Depending on the polarization of the initial optical signal 111, the angle of incident acoustic signals to which the polarization based fiber-end sensor structure 321B is most sensitive may be altered, as shown in FIG. 6C. Accordingly, in embodiments, a control system associated with the optical sensor system 100B may be configured to adjust or optimize the polarization of the initial optical signal 111, such as from input polarization state 1 to input polarization state 2 to increase acoustic sensitivity. These polarization states are provided by way of example only, and may be altered or configured according to operational needs, as discussed below. FIG. 6C illustrates the direction in which input polarization state 1 and input polarization state 2 are most sensitive to incoming acoustic signals. The solid arrows correspond to the directions in which input polarization state 1 is most sensitive, and the dashed arrows correspond to input polarization state 2. Thus, the lobes of the polarization states provide the highest acoustic sensitivity. Accordingly, an input polarization state may be selected and implemented to align with an expected direction of acoustic signals or with a direction in which acoustic sensitivity is most desired. This may permit the optical sensor system 100B to optimize performance of the fiber-end sensor structure 321B according to an incoming direction of an acoustic signal. The angular sensitivity of the polarization based fiber-end sensor structure 321B is not reliant on the structure of the fiber-end sensor structure 321B. In embodiments, a polarization maintaining fiber may be used. After the polarization state is selected and implemented, it is maintained by the optical signal. In embodiments, an adjustable fiber component may be used to provide an adjustable polarization state. In an embodiment, the polarization state may be adjusted during use to account for changing conditions (such as movement of an acoustic transducer 221 generating the acoustic signal and/or movement, rotation, etc., of the fiber-end sensor structure 321B.) Further benefits of the polarization based fiber-end sensor structure 321B may include a simplified sensor structure and no wavelength locking requirements.

Figure 6D:
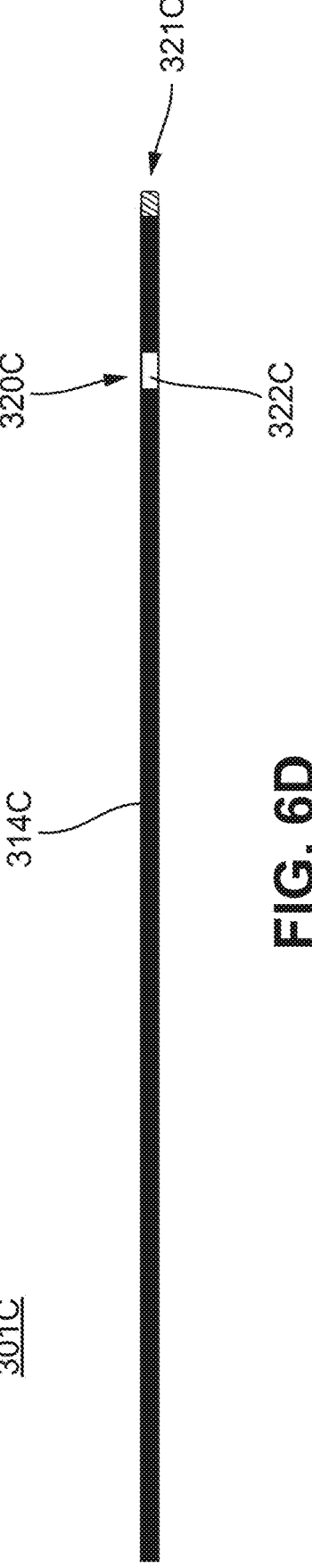

FIG. 6D illustrates a further embodiment of a fiber-based optical sensor consistent with embodiments hereof. A sensor fiber 301C may be an optical fiber configured similarly to sensor fiber 301, including an optical waveguide comprising a core and a cladding structure, as described herein. The sensor fiber 301C may have a fiber end sensor structure 321C disposed on an end thereof. The fiber end sensor structure 321C may include any of the fiber end sensor structures discussed herein, including optical resonator structures, interferometer structures, acoustically responsive fiber end facet structure and polarization based structures and may be configured to measure and/or detect acoustic signals and other physical parameters. The sensor fiber 301C may further include an encapsulating structure 314C configured to reflect incident acoustic signals and a window 320C representing a gap or exposure area that lacks encapsulating structure 314C. The window 320C may expose a polarization based optical sensor structure 322C, e.g., as discussed with respect to FIG. 6B. In embodiments, the polarization based optical sensor structure 322C is formed from the cladding structure and the core of the fiber of which it is a part. That is, the polarization based optical sensor structure 322C may be defined by exposure to incident acoustic signals created by the lack of acoustic shielding at the window 320C, rather than any additional structure within the fiber. The sensor fiber 301C may include any number of windows 320C and polarization based optical sensor structures 322C disposed along its length. Thus, the sensor fiber 301C may include a plurality of optical based acoustic sensor structures, including both fiber end sensor structures 321C and polarization based optical sensor structures 322C configured for mid-fiber location. In further embodiments, the window 320C may be sized along the length of the fiber sufficiently that it will operate as a line sensor as opposed to a point sensor as will be discussed in greater detail below. The line sensor may be a straight line sensor or a curved line receiver. In further embodiments, the sensor fiber 301C may be configured with one or more polarization based optical sensor structures 322C disposed along its length while not including any fiber end sensor structures 321C.

Each of the fiber end sensor structure 321C and the polarization based optical sensor structures 322C may be used to facilitate both imaging and tracking, as described herein. In embodiments, a polarization based optical sensor 322C may be configured, e.g., by size/shape, to facilitate imaging, tracking, or both. For example, a longer polarization based optical sensor structure 322C may increase image quality, acting as a line sensor and the line may be straight or curved. In another example, multiple polarization based optical sensor structures 322C may be used to facilitate tracking methods (multiple sensors along a device may assist with orientation determination, for example.)

In some embodiments, the polarization window portion may also work as a fiber optical sensor that detects scattered acoustic signals and/or tissue harmonics. When the fiber optical sensor is positioned within an imaging area of interest, it may receive weak harmonic or scattered acoustic signals that are unable to propagate very far. The fiber optical may convey optical signals corresponding to the received acoustic signals to a system processor (e.g., processing unit 209). The system processor may use the received optical signals to reconstruct the ultrasound image of the anatomy surrounding the sensor with a delay and sum beamforming method or other suitable image reconstruction method, as discussed in more detail in corresponding U.S. Provisional Application No. 63/522,994, titled Transponder Tracking and Ultrasound Image Enhancement, filed on Jun. 23, 2023 and US Application titled Transponder Tracking and Ultrasound Image Enhancement filed concurrently on Oct. 23, 2023. With this data, the system processor may generate an image of better quality than one generated solely based on the pulses emitted and received by an acoustic probe. In embodiments, the system processor may construct an image based solely on the optical signals received from one or more fiber optical sensors. In embodiments, the optical signals received from one or more fiber optical sensors may be used in conjunction with the acoustic signals received by a traditional ultrasound probe.

This principle is illustrated in greater detail in FIG. 6DD. As shown in FIG. 6DD, an acoustic probe 601 may be used to transmit acoustic signals 620 into an area of interest. The acoustic probe 601 may function as a traditional acoustic probe to detect reflections of the acoustic signals 620 for imaging purposes. These images may be enhanced by additional information obtained by one or more fiber optical sensors. The fiber optical sensor 612 of the sensor fiber 602 may correspond to any of the fiber end optical sensor structures discussed herein and may receive acoustic signals 622. The acoustic signals 622 may result from reflection, scattering, and/or tissue harmonics. As shown in FIG. 6DD, the acoustic signals 622 are generated from points 621 within the area of interest. The fiber optical sensor 612 may be configured to receive acoustic signals 622 from any direction, as discussed herein. The sensor fiber 603 may be configured to act as a polarization based optical sensor, as discussed herein, and may receive acoustic signals 622 from directions lateral to the axis of the sensor fiber 603. As used herein, "lateral" refers to all directions that are not parallel to the axis of the sensor fiber 603. As shown in FIG. 6DD, the acoustic signals 622 may be received by the sensor fiber 602 at any exposed portion along its length and from any direction, as discussed with respect to FIG. 6D. Further, as discussed with respect to and shown in FIG. 6C, the polarization of the sensor fiber 602 may be selected or adjusted to accommodate an expected or desired radial angle of incidence of the acoustic signals 622. FIG. 6DD further illustrates the sensor fiber 604, which may curve within the area of imaging interest. Similar to the sensor fiber 603, the sensor fiber 604 may detect incident acoustic signals 622 lateral, substantially lateral, or from any direction relative to the axis of the sensor fiber 604. Detection of lateral signals at multiple points along the length of the sensor fiber 604 may enhance an ability to track and/or locate the sensor fiber 604 when it is disposed within a medium (e.g., within a human body during a medical procedure). For example, as shown in FIG. 6DD (b), multiple signals incident along the length of the sensor fiber 604 may enhance an ability to determine the location of different portions of the sensor fiber 604 along its length and therefore to identify the location of the entire sensor fiber 604, and not just a tip region. For example, as shown in FIG. 6DD (c), multiple signals incident along the length of the sensor fiber 604 may enhance an ability to determine the location of different portions of the sensor fiber 604 and therefore to identify curvature of the sensor fiber 604 with greater accuracy.

FIGS. 6E and 6F illustrate an optical sensor system for use with a fiber optical sensor according to embodiments herein. FIG. 6F illustrates an optical resonator based optical sensor configured for use with a multi-core optical fiber according to embodiments herein. The optical sensor system 100D of FIG. 6E is configured for use with the multi-core optical resonator based fiber optical sensor 101D, as shown in FIG. 6F. In further embodiments, other optical sensors discussed herein, including, for example, interferometer based sensors may be employed in a multi-core optical fiber based system.

The fiber optical sensor 101D may include a fiber end sensor having an optical resonator based acoustic sensor as described herein. The fiber optical sensor 101D may include a sensor fiber 301D having an optical resonator based fiber-end sensor structure 321D disposed at an end thereof, e.g., at the end of an optical waveguide 311D. Except where noted, the sensor fiber 301D may include features and structures consistent with those of sensor fibers 301 and 351. The optical resonator based fiber-end sensor structure 321D is coupled to the end of the optical waveguide 311D. The optical resonator based fiber-end sensor structure 321D may include an optical resonator sensor 322D, in addition to additional structures and components configured to facilitate the functionality of the optical resonator sensor 322D, as described below. The optical resonator based fiber-end sensor 322D, schematically illustrated in FIG. 6F, may be waveguide-coupled such that it is configured for receiving an initial optical signal 111 (e.g., light) supplied to it via a first optical core 313D of the sensor fiber 301D and providing a returned optical signal 112 back along a second optical core 312D of the sensor fiber 301D. The second optical signal may correspond to and represent an acoustic signal incident upon the optical resonator based fiber-end sensor structure 321D or may correspond to and represent other physical parameters associated with the fiber-end sensor structure 321D. The incident acoustic signal or other physical parameter may cause physical deformation and/or material property alteration of the optical resonator based fiber-end sensor structure 321D. Accordingly, an optical signal provided along the second optical core 312D by the optical resonator based fiber-end sensor structure 321D may be altered by, influenced by, or otherwise indicative or representative of the acoustic signal and therefore may be used to characterize the incident acoustic signal.

The optical resonator based fiber-end sensor structure 321D may include an acoustically responsive polymer portion 317D including parylene or other suitable polymer that is sensitive to acoustic signals. The acoustic impedance of the polymer portion 317D may be selected to match (e.g., within 1%, 5%, 10%, or 20%) of the acoustic impedance of an encapsulating structure or cladding structure 314D of the sensor fiber 301D to enhance the sensitivity of the optical resonator based fiber-end sensor structure 321D, as described above.

The fiber-end sensor structure 321D is disposed at an end of the optical waveguide 311D and may therefore be referred to as a fiber end sensor. The encapsulating or cladding structure 314D may have a first diameter and the fiber end sensor structure 321D may have a second diameter. The first diameter and the second diameter may be substantially the same and/or may have a ratio in a range between 1.05 and 0.95, a ratio in a range between 1.02 and 0.98, or a ratio in a range between 1.01 and 0.99. As discussed above, the sensor fiber 301D may be compact, e.g., wherein the first diameter and/or the second diameter are less than 200 microns, less than 175 microns, less than 150 microns, less than 130 microns, less than 100 microns, or less than 85 microns. With very small fiber diameters, increasing the diameter of the fiber sensor end may further enhance acoustic sensitivity.

The optical sensor system 100D is configured for use with the resonator based fiber optical sensor 101D. The optical sensor system 100D may include a light source 104, such as a laser, a light reception device 103, such as a photodetector, one or more optical waveguides 105, and a multi-core fiber fan-out coupler 109. In operation, the light source 104 supplies the initial light signal 111 to the fiber optical sensor 101D via the optical waveguide 105, through the multi-core fiber fan-out coupler 109. The supplied initial optical signal 111 travels to the optical resonator based fiber-end sensor structure 321D via a first optical core 313D, where it may be affected by an incident acoustic signal, and then is returned by the second optical core 312D as a returned optical signal 112. The returned optical signal 112 travels via the optical waveguides 105 through the fan-out coupler 109 to be received at the light reception device 103. As discussed above, acoustic signals incident on the fiber optical sensor 101D alter the optical characteristics (including the physical structure as well as the optical material properties) of the fiber optical sensor 101D. Such optical characteristic alterations may be measured from the returned optical signal 112 to measure properties and characteristics of the incident acoustic signals. In the embodiment of FIG. 6E, it is not necessary to provide the initial optical signal 111 to the light reception device 103 to measure the optical characteristic alterations, for example, because the parameters of the initial optical signal 111 are known by the system.

The multi-core fiber fan-out coupler 109 serves to couple the single core optical waveguides 105 to the multi-core optical waveguide 311D. Thus, the initial optical signal 111 and the returned optical signal 112 may travel in separate optical cores in the multi-core optical waveguide 311D. As compared to the optical sensor system 100B, use of the multi-core fiber fan-out coupler 109 and multi-core optical waveguide 311D in the optical sensor system 100D may eliminate the need for an optical circulator. Such a design may be advantageous for several reasons. For example, the multi-core fiber fan-out coupler 109 of the optical sensor system 100D may be smaller, lighter, and/or less expensive than an optical circulator, which may permit more flexibility when incorporating the fiber optical sensor 101D into a device or apparatus. In embodiments, other suitable optical couplers configured for coupling single core optical fibers to multi-core optical fibers may take the place of the multi-core fiber fan-out coupler 109.

Figures 6G, 6H:
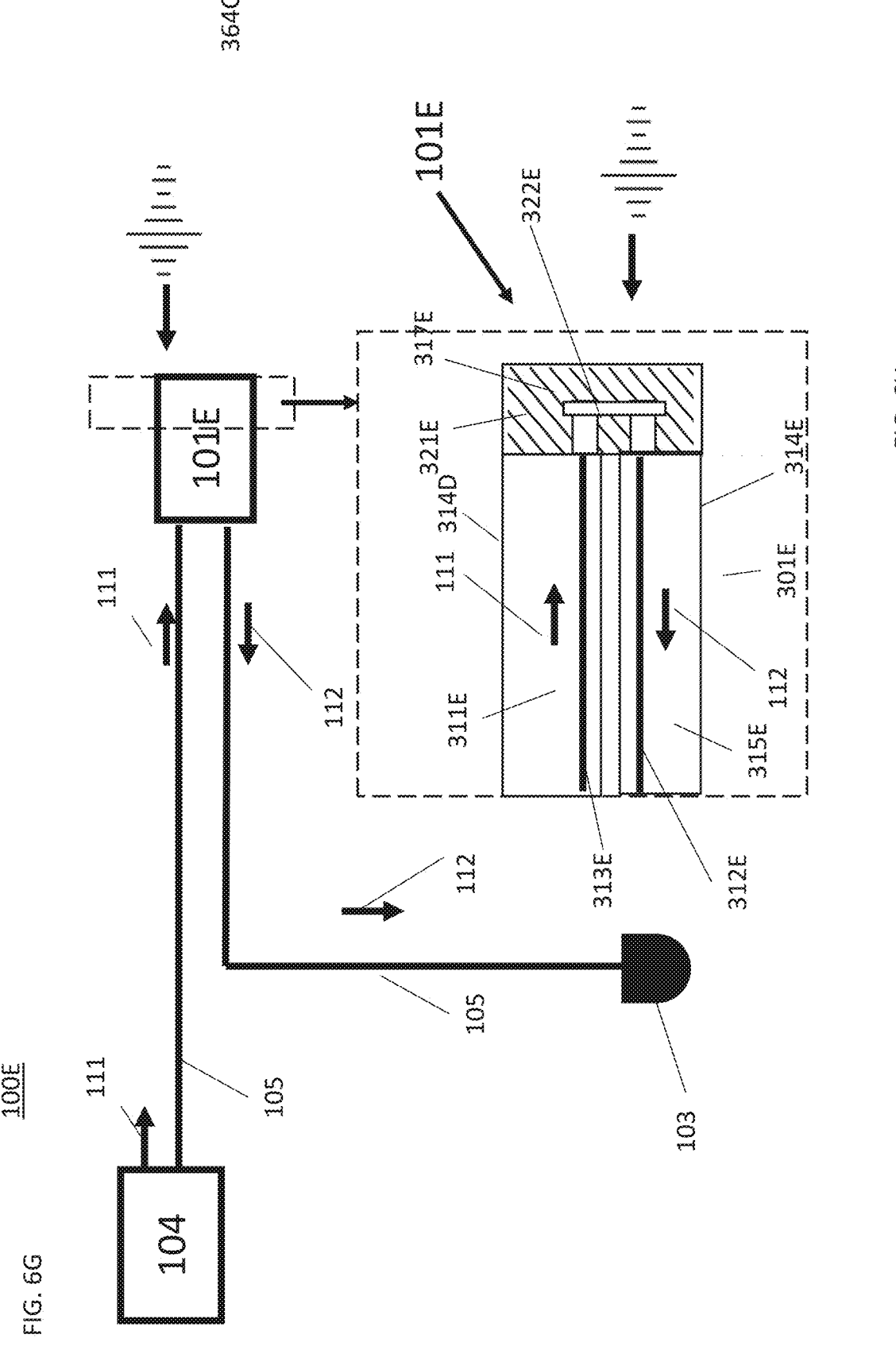
FIGS. 6G and 6H illustrate examples of an optical sensor system and fiber optical sensor consistent with embodiments hereof.

FIGS. 6G and 6H illustrate an optical sensor system for use with a fiber optical sensor according to embodiments herein. FIG. 6H illustrates an optical resonator based optical sensor configured for use with a pair of single core optical fibers according to embodiments herein. The optical sensor system 100E of FIG. 6G is configured for use with the dual fiber optical resonator based sensor 101E, as shown in FIG. 6H. In further embodiments, other optical sensors discussed herein, including, for example, interferometer based sensors may be employed in a dual optical fiber based system.

The fiber optical sensor 101E may include a fiber end sensor having an optical resonator based acoustic sensor as described herein. The fiber optical sensor 101E may include a sensor fiber 301E having an optical resonator based fiber-end sensor structure 321D disposed at an end thereof. Except where noted, the sensor fiber 301E may include features and structures consistent with those of sensor fibers 301 and 351.

The fiber optical sensor 101E may include a dual optical fiber structure. The fiber optical sensor 101E may include a first optical waveguide 311E having a first fiber optical core 313E and a second optical waveguide 315E having a second fiber optical core 312E. Each of the first optical waveguide 311E and the second optical waveguide 315E may be individual optical fibers and may each have a separate cladding structure 314E. The first optical waveguide 311E and the second optical waveguide 315E may be coupled together. For example, the first optical waveguide 311E and the second optical waveguide 315E may be coupled via glue or other adhesive.

The optical resonator based fiber-end sensor structure 321E is coupled to the end of both the first optical waveguide 311E and the second optical waveguide 315E. The optical resonator based fiber-end sensor structure 321E may include an optical resonator sensor 322E, in addition to additional structures and components configured to facilitate the functionality of the optical resonator sensor 322E, as described below. The optical resonator based fiber-end sensor 322E, schematically illustrated in FIG. 6H, may be waveguide-coupled such that it is configured for receiving an initial optical signal 111 (e.g., light) supplied to it via a first optical core 313E of the first optical waveguide 311E and providing a returned optical signal 112 back along a second optical core 312E of the second optical waveguide 315E. The returned optical signal 112 may correspond to and represent an acoustic signal incident upon the optical resonator based fiber-end sensor structure 321E and/or may correspond to and represent one or more other physical parameters associated with the fiber-end sensor structure 321E. The incident acoustic signal and/or other physical parameters may cause physical deformation and/or material property alteration of the optical resonator based fiber-end sensor structure 321E. Accordingly, an optical signal provided along the second optical core 312E by the optical resonator based fiber-end sensor structure 321E may be altered by, influenced by, or otherwise indicative or representative of the acoustic signal and therefore may be used to characterize the incident acoustic signal. In the embodiment of FIG. 6G, it is not necessary to provide the initial optical signal 111 to the light reception device 103 to measure the optical characteristic alterations, for example, because the parameters of the initial optical signal 111 are known by the system.

The optical resonator based fiber-end sensor structure 321E may include an acoustically responsive polymer portion 317E including parylene or other suitable polymer that is sensitive to acoustic signals. The acoustic impedance of the polymer portion 317E may be selected to match (e.g., within 1%, 5%, 10%, or 20%) of the acoustic impedance of an encapsulating structure (or cladding structure) of the sensor fiber 301E to enhance the sensitivity of the optical resonator based fiber-end sensor structure 321E, as described above.

The optical sensor system 100E is configured for use with the resonator based fiber optical sensor 101E. The optical sensor system 100D may include a light source 104, such as a laser, a light reception device 103, such as a photodetector, one or more optical waveguides 105. The one or more optical waveguides 105 may be structurally bound to one another to form the first optical waveguide 311E and the second optical waveguide 315E of the sensor fiber 301E and may be separated to couple with the light source 104 and the light reception device 103. In embodiments, a coupler or other device may be used to facilitate the junction. In operation, the light source 104 supplies the initial light signal 111 to the fiber optical sensor 101E via the optical waveguide 105. The supplied initial optical signal 111 travels to the optical resonator based fiber-end sensor structure 321E via the first optical waveguide 311E, where it may be affected by an incident acoustic signal, and then is returned by the second optical waveguide 315E as a returned optical signal 112. The returned optical signal 112 travels via the optical waveguides 105 to be received at light reception device 103. As discussed above, acoustic signals incident on the fiber optical sensor 101E alter the optical characteristics (including the physical structure as well as the optical material properties) of the fiber optical sensor 101E. Such optical characteristic alterations may be measured from the returned optical signal 112.

The dual fiber design of the sensor fiber 301E eliminates the need for a circulator or a multi-core fan-out coupler. Such a design may be advantageous for several reasons. For example, eliminating a multi-core fiber fan-out coupler and an optical circulator may provide a smaller, lighter, and/or less expensive system, which may permit more flexibility when incorporating the fiber optical sensor 101E into a device or apparatus.

Figures 7A, 7B, 7C, 7D:
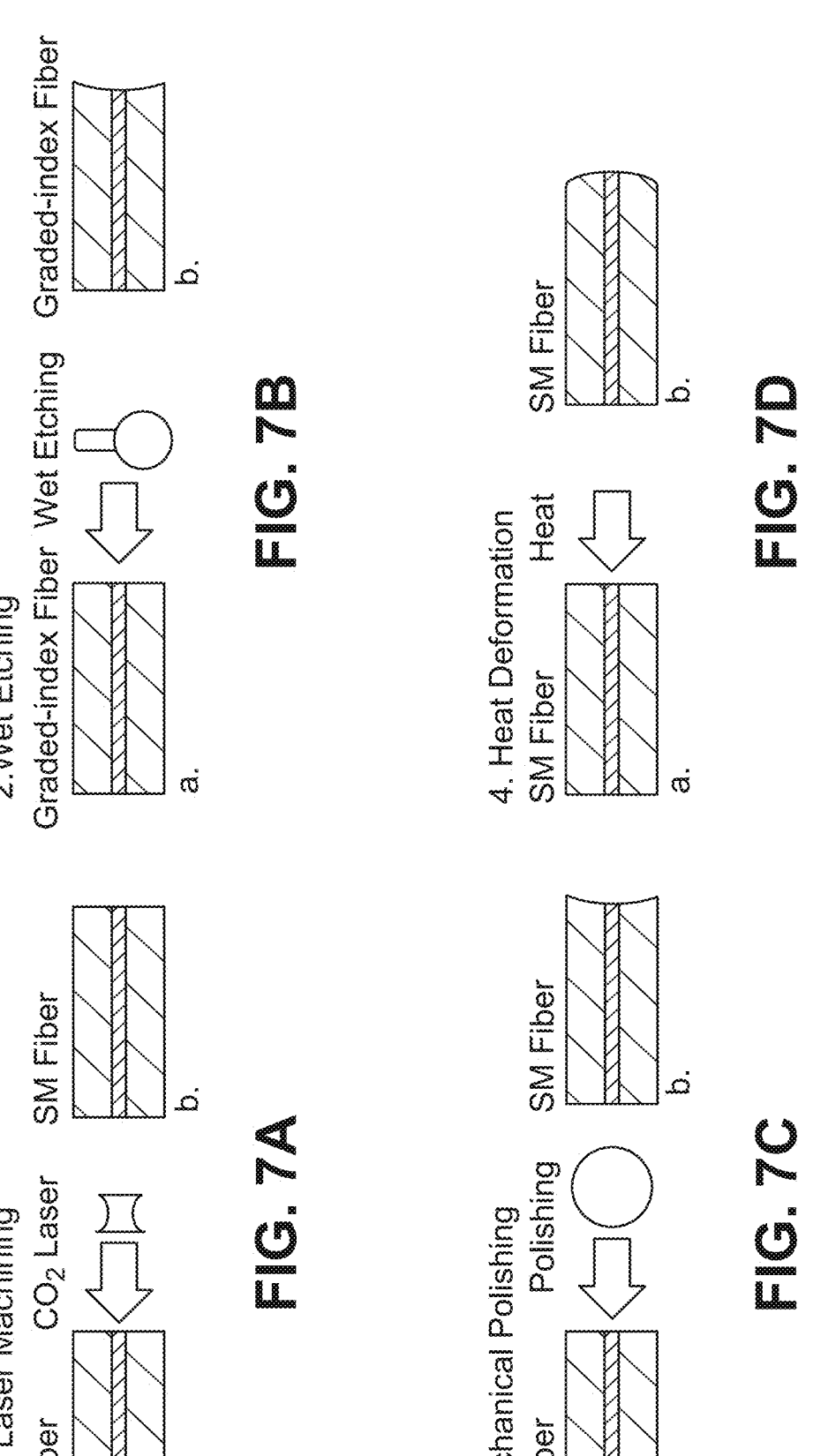
FIG. 7A-FIG. 7D provide examples of manufacturing techniques that may be used to shape or machine an end of an optical waveguide.

FIG. 7A-FIG. 7D provide examples of manufacturing techniques that may be used to shape or machine an end of an optical waveguide. FIG. 7A illustrates a method of $CO_2$ laser machining of an end of an optical waveguide to achieve a concave, for example, to accommodate a proximal reflective surface that is concave with respect to an optical cavity. FIG. 7B illustrates a method of wet etching an end of an optical waveguide to achieve a concave, for example, to accommodate a proximal reflective surface that is concave with respect to an optical cavity. FIG. 7C illustrates a method of mechanical polishing of an end of an optical waveguide to achieve a concave, for example, to accommodate a proximal reflective surface that is concave with respect to an optical cavity. FIG. 7D illustrates a method of $CO_2$ laser machining of an end of an optical waveguide to achieve a concave, for example, to accommodate a proximal reflective surface that is concave with respect to an optical cavity.

FIG. 8A-FIG. 8D provide examples of manufacturing techniques that may be used to manufacture an optical resonator structure at an end of an optical waveguide. FIG. 8A illustrates a method of micro-molding that may be used to form an optical resonator structure. FIG. 8B illustrates a method of dip-coating that may be used to form an optical resonator structure. FIG. 8C illustrates a method of conformal coating that may be used to form an optical resonator structure. FIG. 8D illustrates a method of dip-coating that may be used to form an optical resonator structure.

Figure 9A:
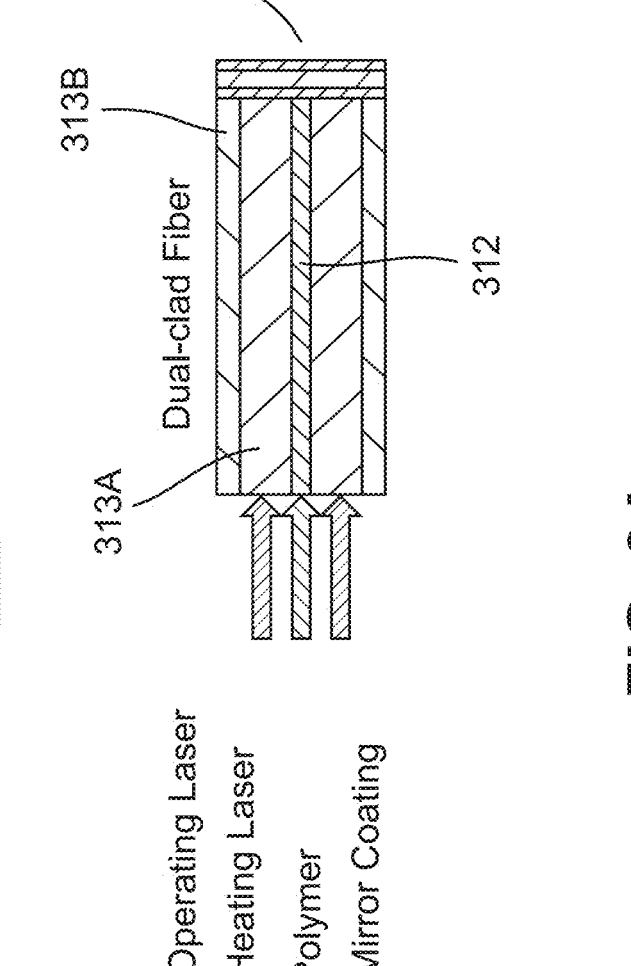
FIGS. 9A-9B illustrate a method of thermal tuning applied to a sensor fiber.

FIG. 9A illustrates a method of thermal tuning applied to a sensor fiber. An interferometer-based fiber sensor (or other optical sensor structure consistent with embodiments hereof) may benefit from a wavelength tuning mechanism to maintain the interferometer-based fiber sensor at an optimum operational point. An optimum operational point may be based on a resonance of the optical sensor structure. In embodiments, the resonance wavelength of the optical sensor structure and the operational wavelength of a laser providing an optical signal may be selected, adjusted, or determined together to optimize or maximize an optical readout. The resonance wavelength of the optical sensor structure and the operational wavelength of the laser may be selected, adjusted, or determined such that the operational wavelength of the laser coincides with a slope of the resonant peak of the optical sensor structure. A specific position on the slope of the resonant peak may vary according to sensor design and application specific requirements. The specific operation position on slope of the resonant peak effects the dynamic range and the sensitivity of the optical sensor structure. In embodiments, an operation position (e.g., wavelength) may be selected so as to have a response amplitude within a range of 10%-90% of a resonance depth, within a range of 10%-30% of a resonance depth, within a range of 30%-50% of a resonance depth, within a range of 50%-70% of a resonance depth, or within a range of 70%-90% of a resonance depth. Accordingly, wavelength tuning according to embodiments hereof may include tuning either the operational wavelength or the laser or the resonance wavelength of the optical sensor to achieve this.

Wavelength tuning mechanism consistent with embodiments hereof may include, for example, a heating or tuning laser or an external tuner configured for tuning via the application of mechanical stress and/or electrothermal heating. While a tunable laser in the back-end system may provide tunability, individual tunability at the sensing front-end (localized tuning) is also desirable, because it may allow (1) a less expensive laser without wavelength tunability and (2) a scalable sensor array with a shared laser. FIG. 9A illustrates one method for localized tuning using photothermal tuning, which does not require extra cabling. In an embodiment, light from an operating laser and a heating laser (at different wavelengths) is guided by the fiber together. The operating laser wavelength may be selected to optimize the sensing performance, and at least one structure on the fiber end (e.g., optical resonator structure 321, part of the encapsulating structure 314 etc. is absorptive at the heating wavelength. By tuning the power of the heating laser light, the local temperature in the optical resonator structure 321 is changed and therefore the temperature sensitive optical transmissivity of the fiber optical sensor is tuned so as to better coincide with the wavelength of the operating laser. Accordingly, the heating laser is operated to adjust the temperature of the optical resonator structure 321 according to the wavelength of the operating laser. The heating laser may be either continuous-wave or pulse-width-modulated. In an embodiment, a sensor fiber 301C may have a dual clad structure. Any of the sensor fibers 301/301A/301B may incorporate the features of sensor fiber 301C. The sensor fiber 301C may include an inner cladding structure 313A and an outer cladding structure 313B. The outer cladding structure 313B may be introduced if the heating wavelength is longer than the cut-off wavelength of the core, which is optimized for operating light transmission.

Figure 9B:
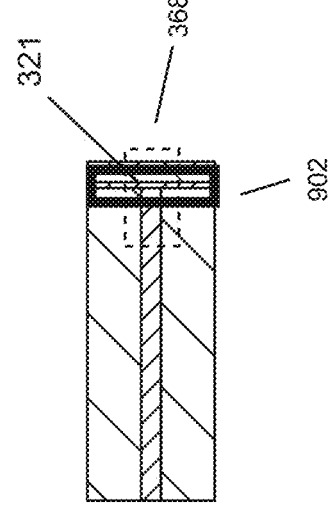

In another localized tuning method, illustrated in FIG. 9B, an external tuner 902 may be provided to replace the heating laser for tuning the sensor transmission through application of, for example, mechanical stress or electrothermal heating. FIG. 9B illustrates sensor fiber 301 having an optical resonator structure 321 by way of example. Any suitable sensor fiber and fiber optical sensor may be used with the external tuner 902. The external tuner 902 may include, for example, a piezoelectric and/or an electrothermal element external to the optical cavity that may be configured to apply pressure (i.e., squeeze) or heat to the optical resonator structure 321. This may require additional electrical cabling, wires, traces, and/or a microheater printed flex circuit along the length of the fiber sensor to enable the external tuners. The extra structures do not affect the optical properties of the sensor as long as the sensor optical path (within dashed frame 368) in the optical resonator structure 321 is not interrupted.

In a further example the optical resonator structure 361 may have an operational wavelength adjusted to more closely align with the wavelength of a light source (e.g., source laser). When multiple fiber optical sensors are arranged in an array, the capability to individually calibrate and fine tune each fiber optical sensor within the array offers the potential to drive and synchronize the operations of each sensor in an array. This synchronization may also empower a user to drive multiple (≥2) fiber optical sensors with one source laser and capture signals from multiple sensors simultaneously. Such a feature is advantageous in constructing a sensor array for imaging. In this process, a feedback loop may be employed to monitor and adjust the heat source or stress to fine tune the operation wavelength of the sensor to ensure its alignment with the source laser. Through simultaneous capture of multiple data points or the collaborative analysis of sophisticated imaging patterns, the synchronized operation of the sensor arrays warrants robust data interpretation.

Figure 10:
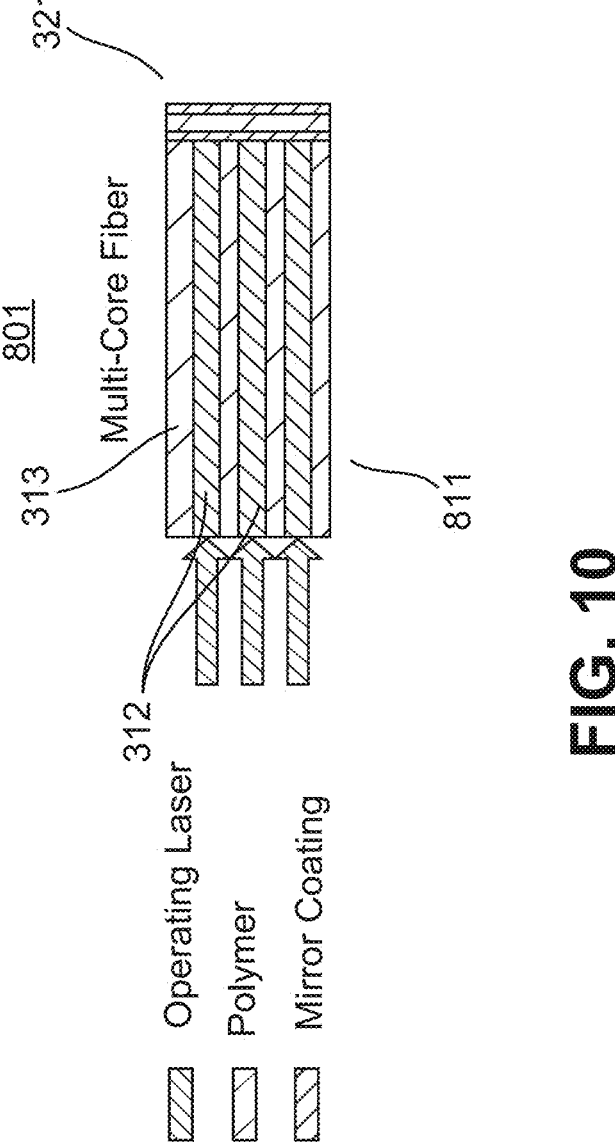
FIG. 10 illustrates an embodiment of a sensor fiber including a multi-core optical waveguide.

FIG. 10 illustrates an embodiment of a sensor fiber including a multi-core optical waveguide. The sensor fiber 801 may include any or all of the features of sensor fibers 301 and 351, as described above. The sensor fiber 801 may include an optical waveguide 811 and an optical resonator structure 321. The optical waveguide 811 includes a plurality of cores 312, for example, 2, 3, 4, 5, 6, 7, 8, 9, etc., within the cladding structure 313.

Figures 11A, 11B:
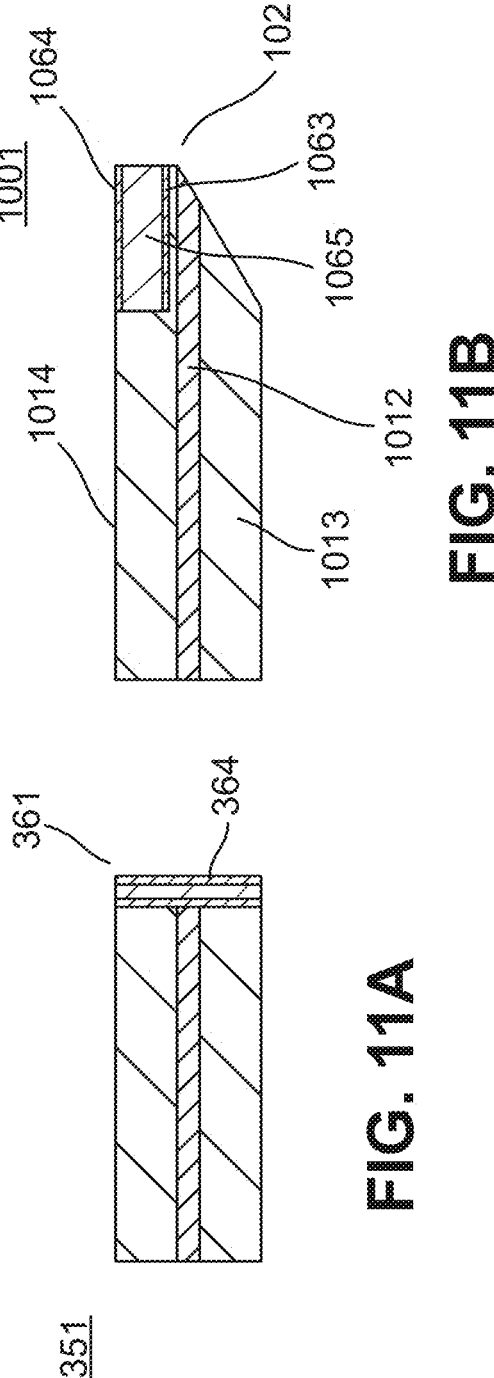
FIG. 11A and FIG. 11B illustrate a comparison between sensor fibers arranged with a forward facing optical sensor and a side facing optical sensor.

FIG. 11A and FIG. 11B illustrate a comparison between sensor fibers arranged with a forward-facing optical sensor and a side facing optical sensor. Consideration of the environment in which the sensor will be used and the direction of the transmitted acoustic beams is an important consideration when incorporating the sensor with the device. For example, some use cases of optical sensors disclosed herein may benefit from a forward-facing arrangement while other use-cases may benefit from a side-facing arrangement.

FIG. 11A illustrates the sensor fiber 351 having a Fabry-Perot resonator functioning as an optical resonator as part of an optical resonator structure, consistent with that shown in FIG. 3A. The optical resonator structure 361 is disposed in a forward facing configuration. In a forward facing configuration, a face(s) or surface(s) of the optical resonator structure 361 that is configured to receive and detect acoustic signals (in optical resonator 362, this face may be the distal reflecting surface 364 or the proximal reflecting surface 363) is arranged such that that the acoustically responsive face(s) or surface(s) is oriented in the same direction as the sensor fiber 351 extends. The sensor fiber 351 and the acoustically responsive surface(s) or face(s) may share an axis. As discussed above, the optical resonator structure 361 may further be configured to detect, measure, and/or respond to other physical parameters.

FIG. 11B illustrates a sensor fiber 1001 having a Fabry-Perot resonator functioning as an optical resonator as part of an optical resonator structure 1021 arranged for side facing capture of incident acoustic signals. The sensor fiber 1001 may include all of the features (even if not illustrated) of sensor fibers 301, 351, and 801. The sensor fiber 1001 may include one or more cores 1012, one or more cladding structures 1013, an encapsulating structure 1014, and an optical resonant structure 1021. The optical resonant structure 1021 may include a Fabry-Perot resonator, as illustrated in FIG. 11B, and/or any other type of optical resonator discussed herein. The optical resonant structure 1021 may include a distal reflecting surface 1064 and a proximal reflecting surface 1063 arranged at either side of an optical cavity 1065. In an embodiment, the optical resonant structure 1021 is configured in a sideways facing configuration. In a sideways facing configuration, an acoustically responsive face or surface of the optical resonator structure 1021 is configured to receive and detect acoustic signals (in optical resonator 362, this face may be the distal reflecting surface 364 or the proximal reflecting surface) is arranged such that that the acoustically responsive face(s) or surface(s) is oriented in the same direction as the sensor fiber 351 extends. The sensor fiber 351 and the acoustically responsive surface(s) or face(s) may have an axis that is substantially perpendicular to an axis of the sensor fiber 1001. In further embodiments, an angle between an axis of the acoustically responsive surface(s) or face(s) and the axis of the sensor fiber 1001 may be between 0° and 90°, depending upon a desired angle of acoustic sensitivity. As discussed above, the optical resonator structure 1021 may further be configured to detect, measure, and/or respond to other physical parameters.

Figure 12:
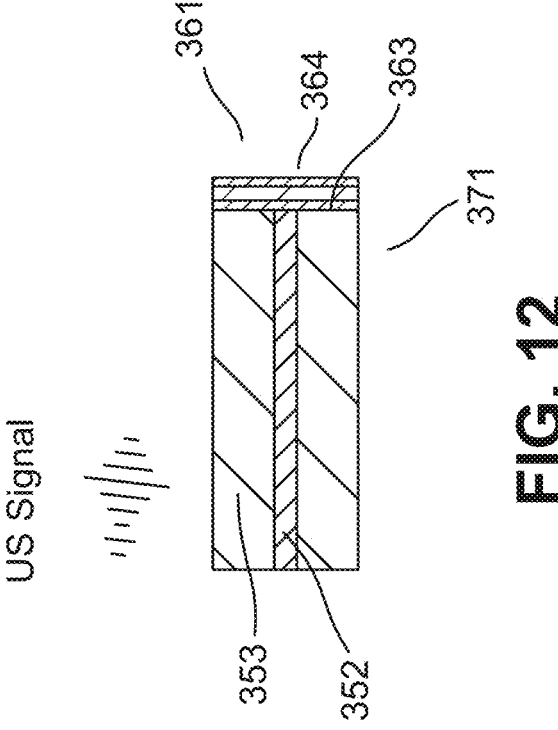
FIG. 12 illustrates an embodiment of a sensor fiber providing backwards looking acoustic detection capabilities consistent with embodiments hereof.

FIG. 12 illustrates an embodiment of a sensor fiber providing acoustic detection capabilities from a direction behind the distal end of the sensor, or proximal detection capabilities and consistent with embodiments hereof. Sensor fibers described herein, such as sensor fiber 301, sensor fiber 351, sensor fiber 801, may be provided with increased proximal detection capabilities. FIG. 12 illustrates sensor fiber 351, having an optical resonator structure 361 having a proximal reflecting surface 363 and a distal reflecting surface 364 arranged to share an axis with the optical waveguide 371. Both the proximal reflecting surface 363 and the distal reflecting surface 364 operate as acoustically responsive surfaces. To increase backwards looking capabilities, the cladding structure 353 may include a material selected to minimize acoustic impedance mismatch with an intended medium within which the sensor fiber 351 is to be used. By minimizing the acoustic impedance mismatch, the critical angle of the boundary between the sensor fiber 351 and the medium in which it is disposed is increased, permitting the optical resonator structure 361 to receive acoustic signals from a greater range of angles. For example, a sensor fiber 351 intended for use within the human body may be include a cladding structure 353 comprising a polymer selected to optimize the detection sensitivity by minimizing any acoustic impedance mismatch. In embodiments, the cladding structure 353 may be selected to have at least one of a Young's modulus (E) smaller than that of the core 352, a photo-elastic coefficient larger than that of the core 352, and a refractive index smaller (n) than that of the core 352. In embodiments, the cladding structure 353 may include benzocyclobutene (BCB) or Polydimethylsiloxane (PDMS), each of which has a small Young's modulus (E), a high photo-elastic coefficient, and a small refractive index (n). Reducing acoustic impedance mismatch serves to increase the acoustic signal that penetrates the cladding structure 353 and strikes the proximal reflecting surface 363. A smaller Young's modulus may increase stress related deformation of the cladding structure 353, which may increase the sensitivity to incident acoustic signals. A higher photo-elastic coefficient may also result in greater sensitivity to acoustic signals, as the optical properties of such material exhibit larger strain related changes. Further suitable materials for the cladding structure 353 may include ultrasonic enhancement materials such as polyvinylidene fluoride, parylene, polystyrene, and/or the like.

Figure 13:
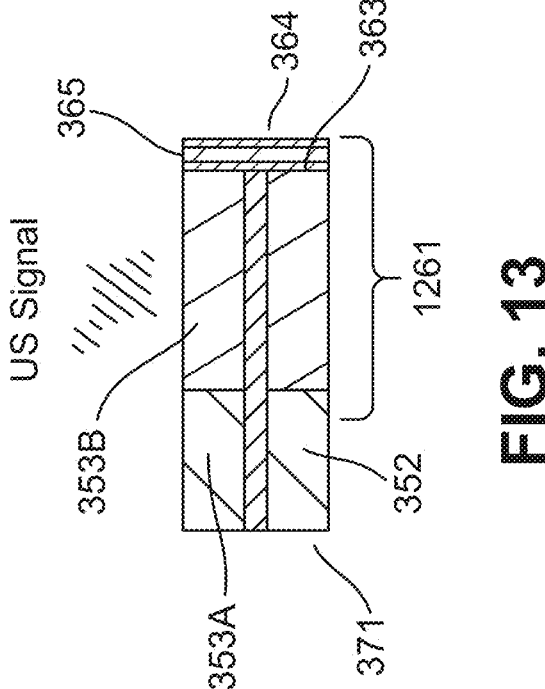
FIG. 13 illustrates an embodiment of a sensor fiber providing increased backwards looking acoustic detection capabilities consistent with embodiments hereof.

FIG. 13 illustrates an embodiment of a sensor fiber providing increased backwards looking acoustic detection capabilities consistent with embodiments hereof. Sensor fibers described herein, such as sensor fiber 301, sensor fiber 351, sensor fiber 801, may be provided with increased backwards looking detection capabilities as shown in FIG. 13. FIG. 13 illustrates sensor fiber 1251, having an optical resonator structure 1261. The optical resonator structure 1261 includes an optical resonator defined by a proximal reflecting surface 363 and a distal reflecting surface 364 arranged to share an axis with the optical waveguide 371 (e.g., the optical resonator is disposed in the same fashion as the forward facing configuration described above). An optical cavity 365 is arranged between the proximal reflecting surface 363 and the distal reflecting surface 364. Both the proximal reflecting surface 363 and the distal reflecting surface 364 operate as acoustically responsive surfaces. The optical resonator structure 1261 may further include any features of optical resonators and optical resonator structures discussed herein in any suitable combination. To increase backwards looking capabilities, the optical resonator structure 1261 may include a distal portion of the optical waveguide 371, specifically structured to increase acoustic sensitivity at the proximal reflecting surface 363. The optical resonator structure 1261 may include the cladding structure of the distal end of the optical waveguide 371, which may include a proximal cladding structure portion 353A and a distal cladding structure portion 353B. The distal cladding structure portion 353B is disposed closer to the optical resonator. The distal cladding structure portion 353B may be selected so as to have a material that reduces or minimizes acoustic impedance mismatch with an intended medium within which the sensor fiber 1251 is to be used. For example, the distal cladding structure 353B may include a polymer, as discussed above. In embodiments, the distal cladding structure 353B may include benzocyclobutene (BCB) or Polydimethylsiloxane (PDMS), each of which has a small Young's modulus (E), a high photo-elastic coefficient, and a smaller refractive index (n). The distal cladding structure 353B may have a length dimension sufficient to permit acoustic signals from backwards looking angles to reach the proximal reflecting surface 363 of the optical resonator. The proximal cladding structure portion 353A may include any suitable material for optical waveguides, including, for example silica. As discussed above, the optical resonator structure 1261 may further be configured to detect, measure, and/or respond to other physical parameters.

Figure 14:
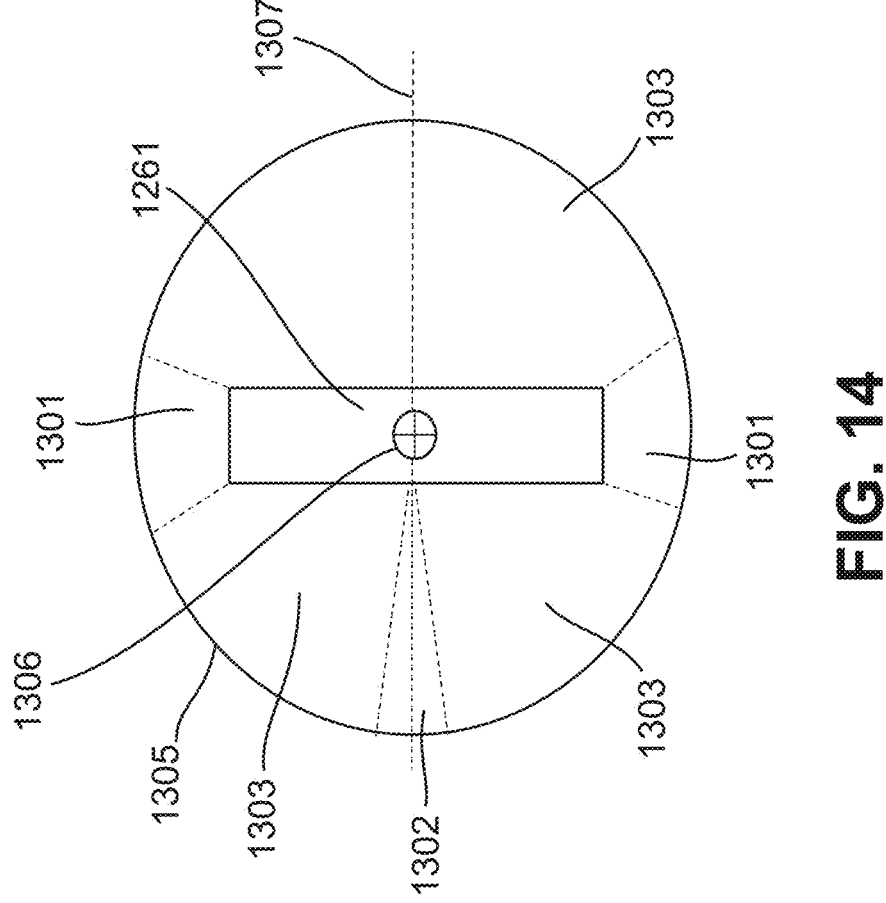
FIG. 14 illustrates a directional range of optical resonant structures consistent with embodiments hereof.

FIG. 14 illustrates a directional range of optical resonant structures consistent with embodiments hereof. As discussed above, the optical resonator structure 1261 may be configured to detect acoustic signals at a broad range of incidence. In embodiments, the optical resonator structure 1261 may be configured to detect acoustic signals across a directional range of at least 180 degrees, at least 270 degrees, at least 300 degrees, or at least 330 degrees. In some embodiments, the optical resonator structure 1261 may be configured to detect acoustic signals in an omni-directional fashion, e.g., across a range of 360 degrees. FIG. 14 illustrates a side view of an optical resonator structure 361 consistent with embodiments hereof. The circle 1305 represents a 360 range around the optical resonator structure 1261 and has an axis 1306 substantially perpendicular to an axis 1307 of the optical resonator structure 1261. The circle 1305 represents the 360 range from which acoustic signals may be incident upon the optical resonator structure 1261. The optical resonator structure 1261 may be configured to detect acoustic signals in the acoustically responsive portions 1303 of the circle 1305 and may have reduced sensitivity or detection ability in the portions of reduced acoustic sensitivity, including lateral portions 1301 and core portion 1302. In the lateral portions 1301, incident acoustic signals may be less detectable due to their oblique angle of incident upon the reflecting surfaces of the optical resonator. In the core portion 1302, acoustic signals may be less detectable due to blockage from the core of the optical waveguide. The sum of the ranges of the acoustically responsive portions 1303 may represent the range over which the optical resonator structure 1261 detects acoustic signals. Different arrangements of optical resonator structures (e.g., the side facing optical resonator structure 1021) may have different arrangements of acoustically responsive portions 1303 and portions of reduced acoustic sensitivity.

In embodiments, the optical resonator structure 361 is radially symmetric. Accordingly, the acoustically responsive range defined by the two dimensional circle 1305 may be rotated around the axis 1307 to define a three dimensional acoustically responsive range of the optical resonator structure 1261. It will be understood that further effects on the acoustically responsive range may be caused by structures around the optical resonator structure 1261, including, for example, a medical device distal end 231.

Figure 15:
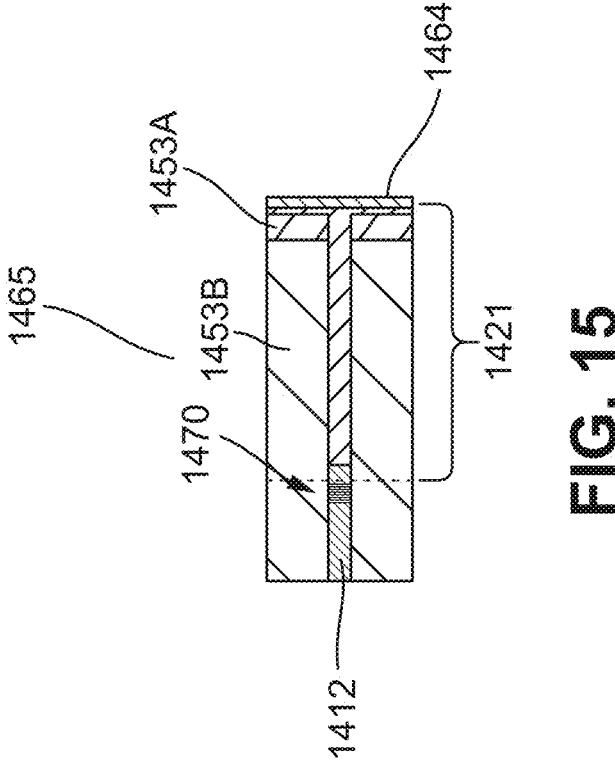
FIG. 15 illustrates an optical resonator structure including an in fiber Bragg grating consistent with embodiments hereof.

FIG. 15 illustrates an optical resonator structure including an in-fiber Bragg grating consistent with embodiments hereof. The optical resonator structure 1421 may be provided in combination with any of the sensor fibers discussed herein. The optical resonator structure 1421 includes a distal reflecting surface 1464, an elongated optical cavity 1465 comprising a distal cladding structure 1453A, and a proximal cladding structure 1453B, and a Bragg grating 1470. As in the optical resonator structure 1261, the distal cladding structure 1453A may include a polymer (e.g., benzocyclobutene (BCB) or Polydimethylsiloxane (PDMS)) while the proximal cladding structure 1453B may include, for example, silica glass. The proximal cladding structure 1453B may be greater in length than the distal cladding structure 1453A, for example, more than 2×, more than 5×, more than 10×, etc. In an embodiment, the proximal cladding structure 1453B may be approximately 10 times the length of the distal cladding structure 1453A, e.g., the distal cladding structure may be approximately 10 microns in length while the proximal cladding structure is approximately 100 microns in length. In embodiments, the proximal cladding structure 1453B may have a Young's modulus in the range of 60-80 GPa while the distal cladding structure 1453A has a Young's modulus in the range of 0.8-1.2 GPa. In embodiments, the proximal cladding structure 1453B may have photo-elastic coefficients $C1=-6*10^{-13}$ 1/Pa and $C2=-4.2*10^{-12}$ 1/Pa while the distal cladding structure 1453A has photo-elastic coefficients $C1=-4.8*10^{-11}$ 1/Pa and $C2=-2.9*10^{-11}$ 1/Pa. While these numbers are provided, such photo-elastic coefficients are a relative number depending on the material selected. For the distal end, a material with larger C1 or C2 values is preferable to optimize the acoustic sensitivity. The Bragg grating 1470 is integrated within the structure of the core 1412 and defines variations in the refractive index of the core 1412, thereby producing a structure that may reflect light of specific wavelengths. The optical resonator structure 1421 operates as a hybrid Fabry-Perot resonator. In this configuration, the distal cladding structure 1453A (e.g., the polymer structure) provides the major response of the acoustic signal. The distal cladding structure 1453A may be directly fabricated via two-photon-polymerization (TPP) 3D printing on the top of the fiber with an in-fiber Bragg grating reflector. One advantage of the hybrid optical resonator structure 1421 is the combination of broad bandwidth and high sensitivity. In some designs, there is a trade-off between broad bandwidth and high sensitivity. In this hybrid configuration, the total length of the elongated optical cavity 1465 is longer because it is the sum of the distal cladding structure 1453A and the proximal cladding structure 1453B. With a longer cavity length, in regular design, the frequency bandwidth response may be narrower. However, in this hybrid configuration, since the major response of the FPI sensor is coming from the polymer region, the effective sensor thickness is still very small and provides a broadband response. As discussed above, the optical resonator structure 1421 may further be configured to detect, measure, and/or respond to other physical parameters.

Figure 16:
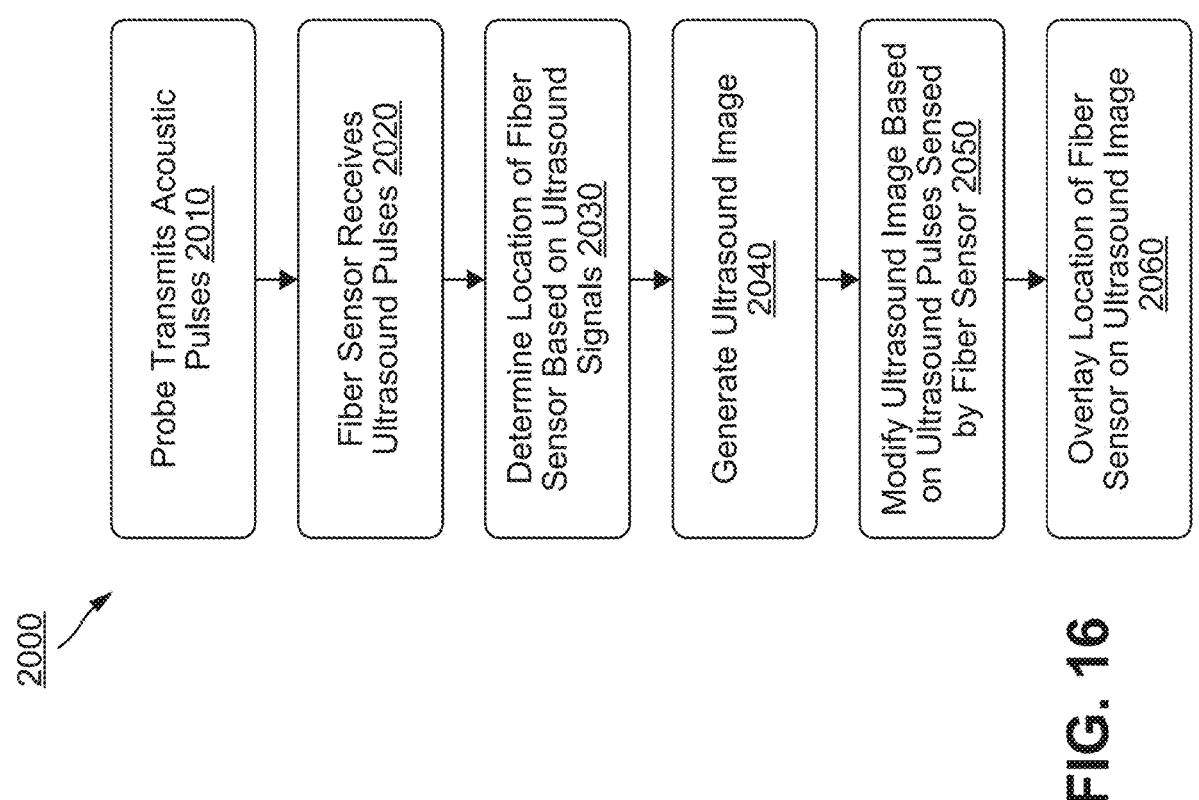
FIG. 16 illustrates a method of operating a fiber based optical sensor consistent with embodiments hereof.

FIG. 16 illustrates steps in a method of generating location and imaging information by a fiber based optical sensor. More details can be found in co-pending application U.S.

Provisional No. 63/522,994, titled Transponder Tracking and Ultrasound Image Enhancement, filed the Jun. 23, 2023 and US Patent Application titled Transponder Tracking and Ultrasound Image Enhancement filed concurrently on Oct. 23, 2023.

The method 2000 may include block 2010, wherein the transponder, for example, the acoustic probe 245 shown in FIG. 2, transmits acoustic pulses into the medium. The transponder may transmit these pulses using a variety of known methods or as described above.

At block 2020, the fiber optical sensor 101 receives the ultrasound pulses transmitted from probe 245 and/or scattered signals or tissue harmonics. The fiber optical sensor 101 then converts the ultrasound pulses, scattered signals and/or tissue harmonics to signals that are then transmitted to the processing unit 209.

At block 2030, the processing unit 209 determines the location of the fiber sensor based at least in part on the signals received from the probe 245. For example, the processing unit 209 may utilize triangulation or coherent image formation to determine the position of the medical device distal end based on a plurality of signals received from the probe 245 and fiber optical sensor 101.

At block 2040, the processing unit 209 and image reconstruction or data unit 206 generates an ultrasound image based on signals returned to the probe 245 and/or scattered signals and tissue harmonics sensed by the fiber sensor. The ultrasound image may be transmitted to and displayed on the display.

At block 2050 the processing system modifies the ultrasound image based on the ultrasound pulses received from the fiber optical sensor 101. In embodiments, the processing system may also produce and display the ultrasound image based on the ultrasound pulses received by the fiber optical sensor without information from the ultrasound pulses received by probe 245.

At block 2060, the processing system 200 overlays the location of the fiber optical sensor 101 over the ultrasound image. Thus, when viewed by a user, such as an ultrasound technician, physician, other medical personnel, or patient, the fiber optical sensor 101 on the medical device distal end are shown on the same display as the ultrasound image, indicating where in the medium, the fiber optical sensor 101 on the medical device distal end is located.

Figures 17A, 17B:
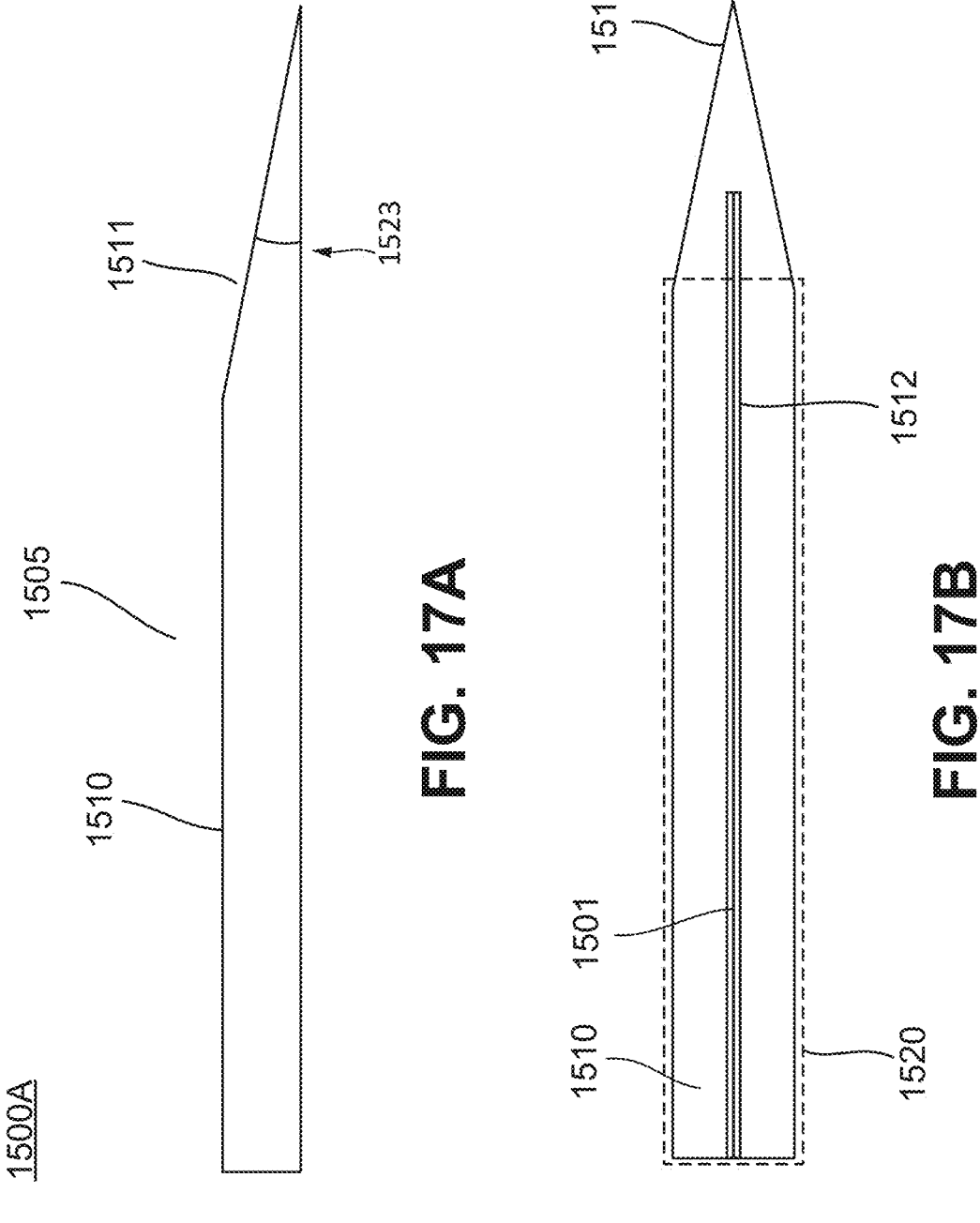
FIGS. 17A-17B illustrate needles configured with a sensor fiber according to embodiments herein.

FIGS. 17A and 17B illustrate a needle configured with a sensor fiber according to embodiments herein. The needle 1500A may be an example of a medical device distal end 231 and may include one or more sensor fibers 1501 integrated therewith. The sensor fiber 1501 may include any of the sensor fibers (having any of the optical resonator structures) described herein and/or may include any combination of features of the sensor fibers described herein. The needle 1500A may be any type of needle of any appropriate size or functionality. The needle 1500A comprises a needle body 1505 having a needle shaft portion 1510 and a needle tip portion 1511. The needle tip portion 1511 may be characterized by a needle polishing angle 1523. Further, the needle 1500A includes at least one sensor channel 1512 extending over the needle body 1505 for at least a portion of the length of the needle shaft portion 1510 and the needle tip portion 1511.

In embodiments, the sensor channel 1512 may include a trench, depression, or groove in the needle body 1505. The sensor channel 1512 may be sized and configured to receive a sensor fiber 1501 consistent with embodiments hereof. For example, in embodiments, the sensor channel 1512 may be approximately 125 to 250 microns in width to accommodate a sensor fiber 1501 that is 80 microns in diameter. The needle 1500A may include a plurality of sensor channels 1512 to accommodate multiple sensor fibers 1501. For example, the needle 1500A may include 2, 3, 4, or more sensor channels 1512 accommodating multiple sensor fibers 1501 arranged around a circumference of the needle 1500A. The sensor fiber 1501 is arranged within the sensor channel 1512 such that the distal end, bearing the optical resonator structure, is positioned at or adjacent the distal end. The sensor channel 1512 may be configured with a depth such that the sensor fiber 1501 does not extend beyond the outer surfaces of the needle body 1505.

In further embodiments, a sensor channel may be created by adding material to the outer surface to form the channel, e.g., as a guide. In an example, material may be layered onto the exterior of the needle to create the channel 1512, as raised continuous or intermittent structures. In another example, an adhesive material or tape may be wrapped in a spiral configuration with spaces within the spirals to form the sensor channel or may be selectively positioned along the needle length to form the sensor channel and guide the sensor fiber along the length. In still another example, an extruded needle may include a tubular sensor channel in the form of a lumen running therethrough.

The sensor channel 1512 allows the sensor fiber 1501 to sit within a protected area of the needle body 1505. This serves to protect the sensor fiber 1501 and to create a smooth needle surface for insertion. The sensor channel 1512 may be disposed on an outer surface of the needle body 1505 (as illustrated in FIG. 17B) or on an inner surface of the needle body 1505.

The sensor fiber 1501 may be secured to the needle body 1505. In embodiments, the sensor fiber 1501 may be secured within the sensor channel 1512 by a potting compound, such as Norland-65 glue, Norland 81 glue, MY-132A polymer, MY-133, BIO-133, DC-133 or any other suitable potting compound. The potting compound may be selected according to its acoustic and mechanical properties, for example, the speed of sound, acoustic impedance, thermal conductivity, water proofing, etc. The potting compound may also offer modification of acoustic impedance matching to the surrounding medium in addition to the mechanical fixing and protection of the sensor. The potting compound may be employed over all of or over a portion of the sensor channel 1512. In embodiments, the sensor fiber 1501 may be secured within the sensor channel 1512 by a sheath 1520. The sheath 1520 is configured to wrap around the needle body 1505. The sheath 1520 may mechanically secure the sensor fiber 1501 to the needle body 1505. The sheath may wrap around the needle with the fiber insides the slot, allowing the fiber to be freely floating within the groove/slot. This can allow bending/flexibility of the needle. In embodiments, the sensor fiber 1501 may be secured at least partially by both a sheath 1520 and a potting compound. Such an arrangement may permit relative movement between the sensor fiber 1501 and the needle body 1505, thus providing potential strain relief in the event of needle bending. The needle 1500A may be fabricated of any suitable material, including, for example, medical grade materials including metals such as stainless steel or polymers such as PEEK (Polyetherketone). In embodiments, the needle 1500 may be fabricated via an additive manufacturing technique, such as 3D printing, injection molding or extrusion.

Figures 18A, 18B:
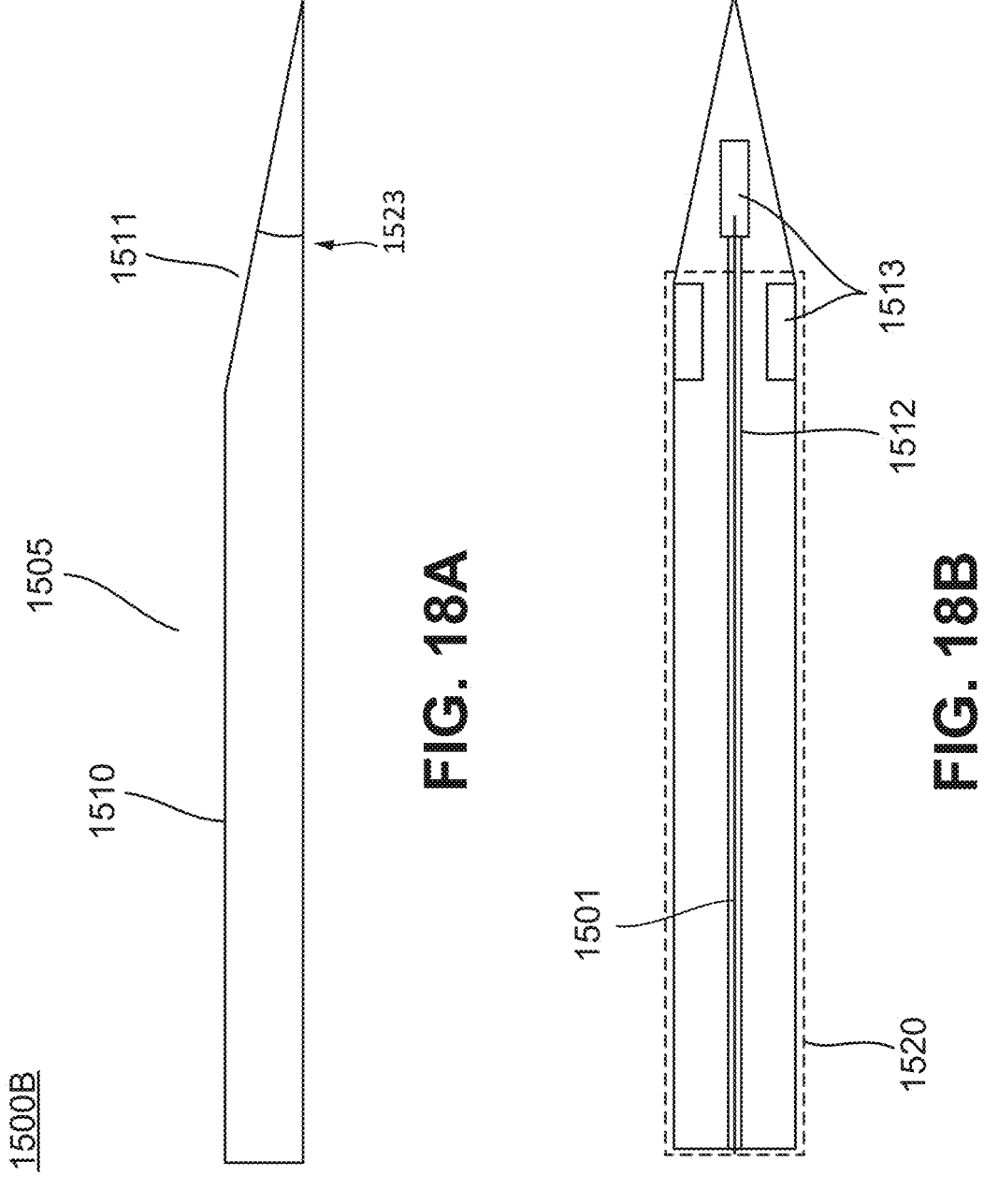
FIGS. 18A-18D illustrate needles configured with a sensor fiber according to embodiments herein.

A further embodiment of a needle incorporating a fiber based optical sensor is illustrated in FIGS. 18A and 18B. The needle 1500B may further include one or more windows 1513. The window 1513 is an opening in the needle body

1505 disposed at end of the sensor channel 1512. The needle 1500B may include a plurality of sensor channels 1512 and a corresponding plurality of windows 1513 to accommodate multiple sensor fibers 1501. The sensor fiber 1501 may be arranged within the sensor channel 1512 such that the distal end, bearing an optical sensor, extends into the window 1513. In this embodiment, the distal end of the sensor fiber 1501 may be secured within the window 1513 by a potting compound while the proximal portion of the sensor fiber 1501 may be secured to the needle body 1505 by the sheath 1520. This will permit relative movement between the sensor fiber 1501 and the needle body, thus providing strain relief in the event of needle bending.

The window 1513 allows acoustic signals to reach the fiber optical sensor of the sensor fiber 1501 without blockage by the needle body 1505. The edge of the window 1513 may create boundaries for acoustic signal diffraction and permit the acoustic signals to bend and propagate around the edges of the window to reach the fiber optical sensor at the end of the sensor fiber 1501. The diffraction effect has the function of increasing the circular range of acoustic signal detection of the sensor fiber 1501. Additionally, the edges of the channel on the surface of the needle may also have a diffraction effect that aids in detection of the needle shaft.

In embodiments, an optical ultrasound sensor consistent with embodiments hereof may integrated with a medical device (e.g., at a medical device distal end 231) and may work with an ultrasound source (array) configured in an ex vivo location to provide location information of the medical device distal end 231 and/or to provide a real-time acoustic monitoring at the target/anatomy area of a procedure. In different application scenarios, the incoming acoustic signal direction may be roughly classified into two types, namely (1) transverse fire; and (2) axial fire, as shown in FIGS. 18C and 18D.

Figures 18C, 18D:
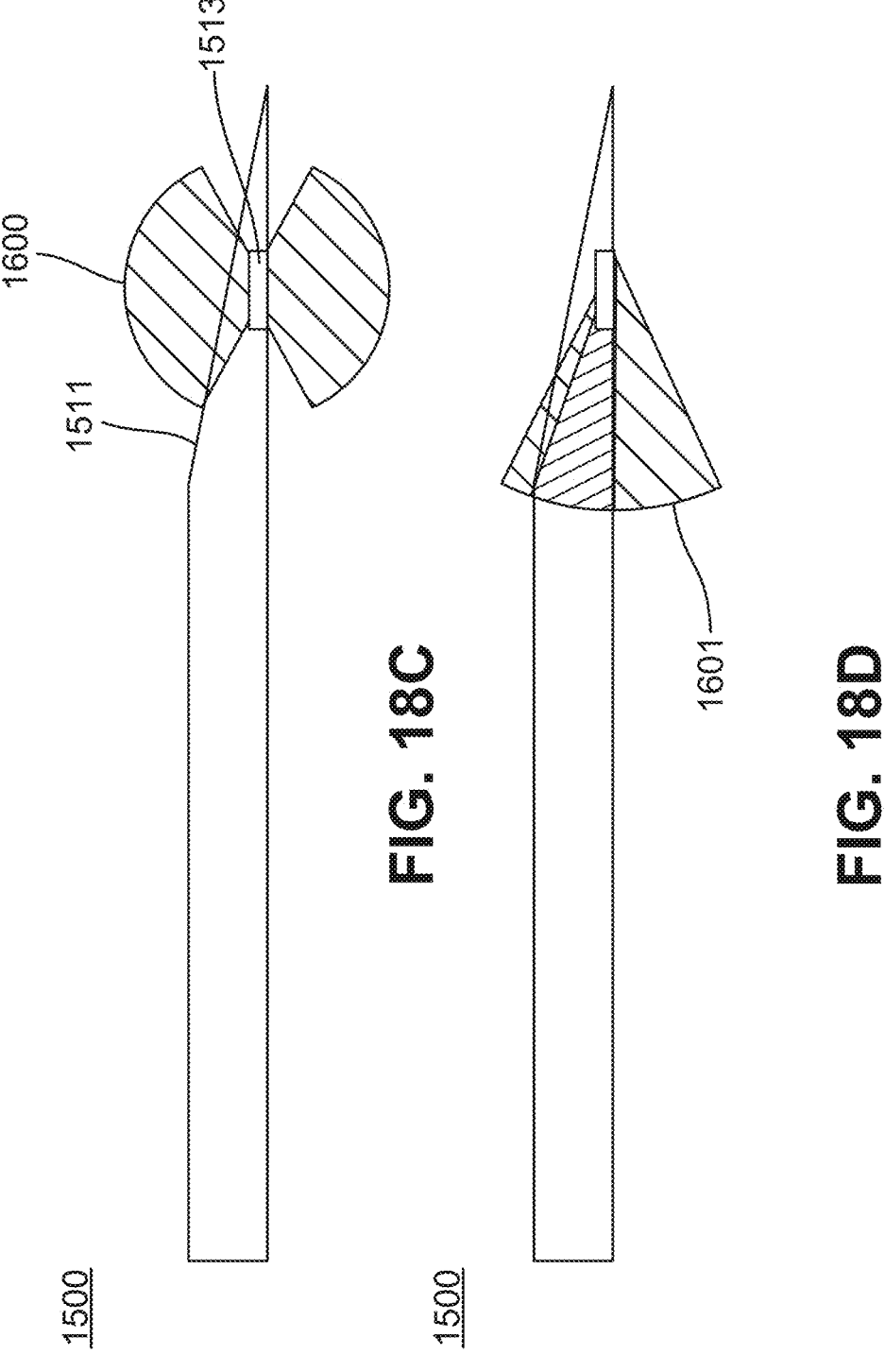

FIGS. 18C and 18D illustrate acoustic signals incident upon a sensor fiber disposed within a needle window 1513. For clarity purposes, the sensor fibers are not shown in these Figures. FIG. 18C illustrates a transverse acoustic signal 1600 while FIG. 18D illustrates an axial acoustic signal.

The transverse acoustic signal 1600 of FIG. 18C is typical of a situation that may occur when using a side-view endoscopic ultrasound transducer or an external transducer. The location of the window 1513 close to the needle tip portion 1511 permits an ultrasound field to reach the window (and fiber end sensor structure located therein) from either side without blockage from an opposite wall of the needle. The fiber end sensor structure itself may be arranged in a side-facing or forward facing fashion and may also be a polarization based sensor configured to receive lateral (transverse) signals, depending on the requirements of the application.

The axial acoustic signal 1601 of FIG. 18D is typical of a situation occurring with respect to a front-view endoscopic ultrasound transducer. Due to the small footprint of an endoscopic device, the typical incident angle may be small with respect to the needle body. As shown in FIG. 18D, when the incident angle is smaller than needle polishing angle 1523 (as shown in FIG. 18D), at least a portion of the acoustic signal 1601 may be blocked by the needle body (shown in thicker crosshatch). To address this, in an embodiment, an additional window 1513 may be included in the needle body 1505 opposite to the sensor window to permit an axial acoustic signal 1601 to pass through and reach the optical resonator structure. In another embodiment, an orientation of the needle 1500A/B may be manipulated to ensure that low angle axial acoustic signals arrive from the portion of the needle where the optical resonator structure is not located. In another embodiment, the polishing angle 1523 may be selected according to expected acoustic angles of incidence.

Figure 19:
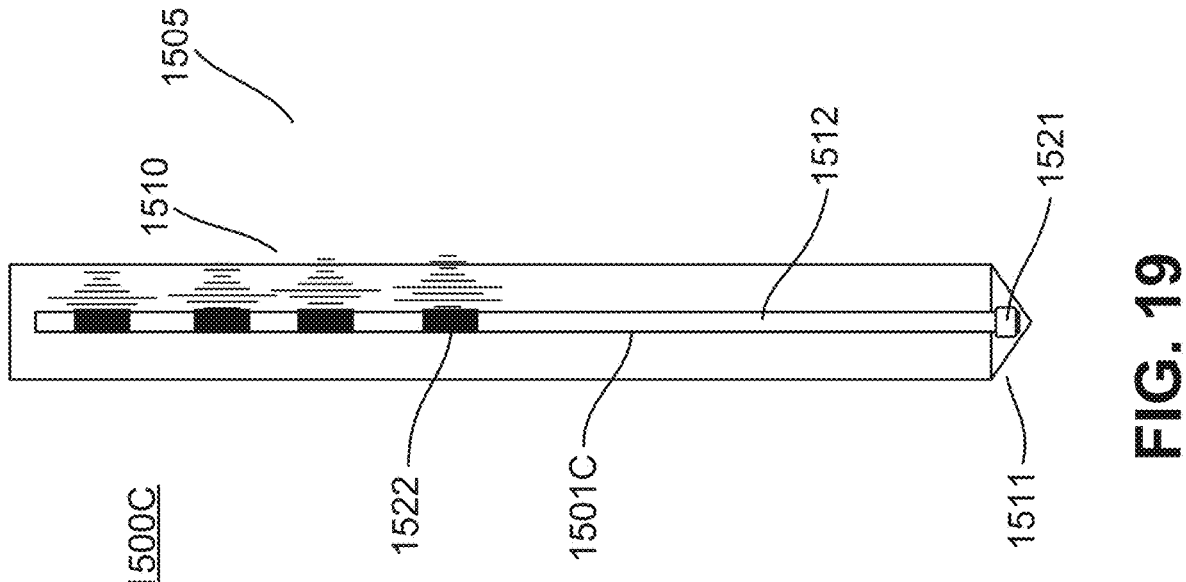
FIG. 19 illustrates acoustic signals incident upon a sensor fiber from a lateral direction.

A further embodiment of a needle incorporating a fiber based optical sensor is illustrated in FIG. 19. Similar to needles 1500A and 1500B, the needle 1500C comprises a needle body 1505 having a needle shaft portion 1510 and a needle tip portion 1511. The needle tip portion 1511 may be characterized by a needle polishing angle. Further, the needle 1500C includes at least one sensor channel 1512 extending over the needle body 1505 for at least a portion of the length of the needle shaft portion 1510 and the needle tip portion 1511. The needle 1500C may include one or more sensor fibers 1501C disposed in one or more sensor channel 1512 thereof. The sensor fibers 1501C may be similar to the sensor fiber 301C and thus may include a fiber end sensor structure 1521 disposed at an end thereof as well as one or more polarization based sensor structures 1522 disposed along a length thereof. The polarization based sensor structures 1522 located along the length of the needle 1500C may provide enhanced visualization of the needle 1500C when acoustic signals used to track or visualize the needle 1500C strike the polarization based sensor structures 1522. Information gathered from the optical signals indicative of the incident acoustic signals may be employed alone and/or in combination with traditional acoustic ultrasound imagery to provide an improved visualization of the needle 1500C. The polarization based sensor structures 1522 may operate according to the principles discussed above with respect to the polarization based sensor structures 322C and with respect to FIGS. 6D and 6DD.

Figure 20B:
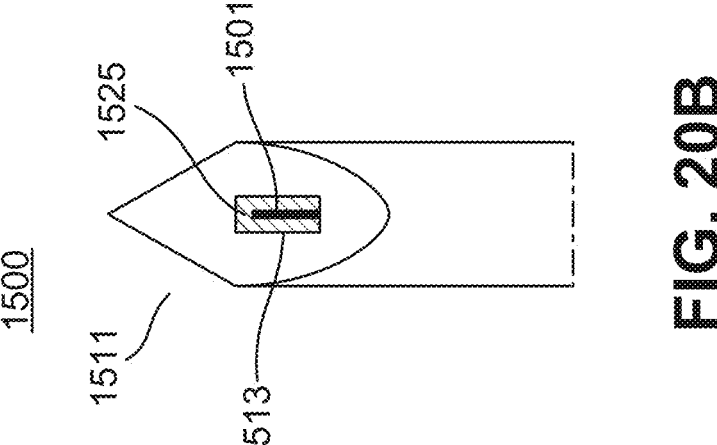
FIGS. 20A-20B provide closeup illustrations of a needle having an integrated sensor fiber consistent with embodiments hereof.
Figure 20A:
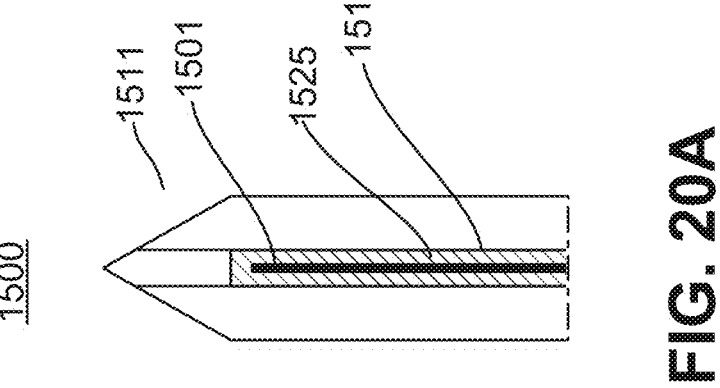

FIG. 20A and FIG. 20B provide further closeup illustrations of the needle 1500 having an integrated sensor fiber 1501. FIG. 20A illustrates a perspective from a first side of the needle 1500 on which the channel 1512 is located and FIG. 20B illustrates a perspective from a second side of the needle 1500 opposite from the first side. The second side of the needle 1500 includes a view of the interior of the needle 1500 at the needle tip portion 1511. As illustrated, the sensor fiber 1501 is disposed within a sensor channel 1512 of the needle 1500 extending from the needle shaft portion 1510 and into the needle tip portion 1511. The window 1513 is disposed within the needle tip portion 1511, thereby ensuring that both sides of the window 1513 (and the sensor fiber 1501 disposed therein) are exposed to incoming acoustic signals. Further, FIGS. 20A-20B illustrate the potting compound 1525 securing the sensor fiber 1501 within the window 1513.

Figure 20D:
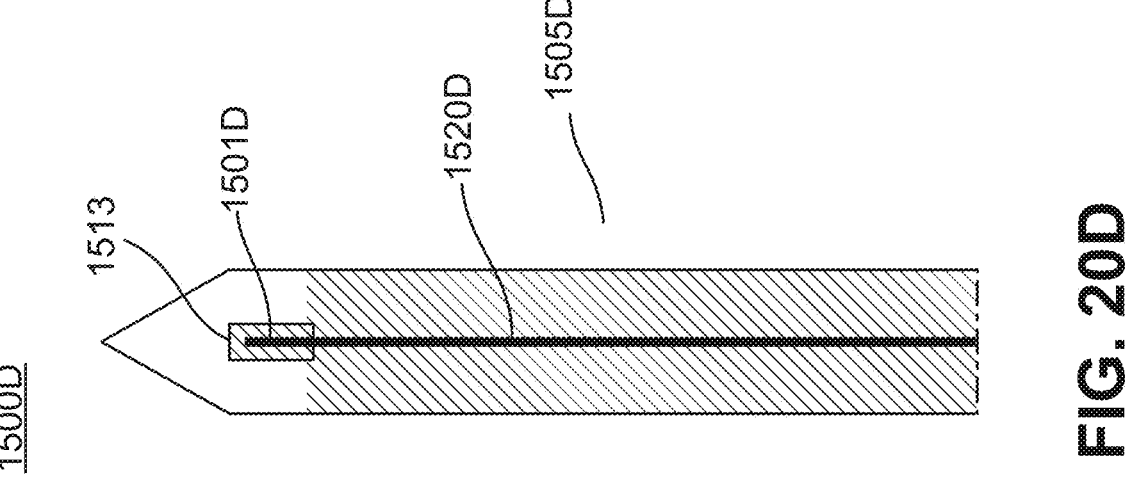
FIGS. 20C-20D illustrate needles having sensor fibers included therein, according to embodiments hereof.
Figure 20C:
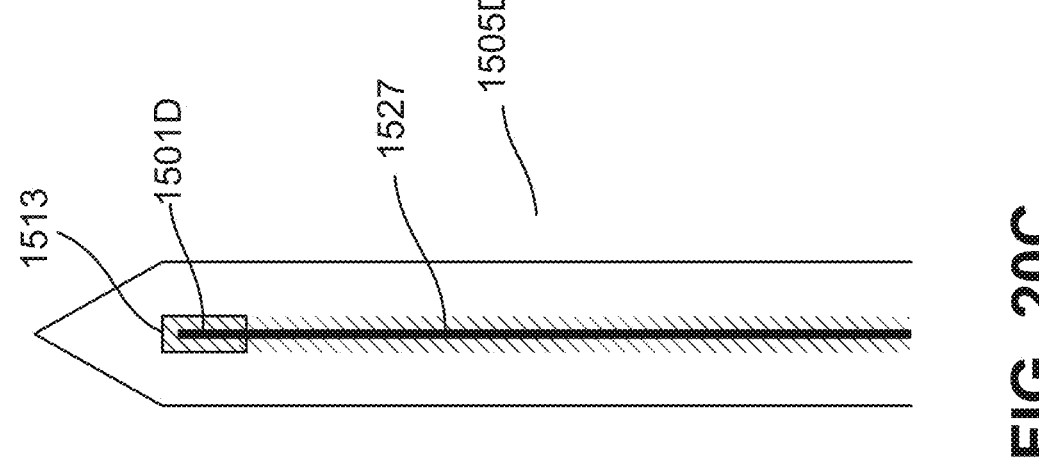

In a further embodiment, shown in FIG. 20C, sensor fiber 1501D may be secured to the surface of the needle body 1505D of needle 1500D without a channel or other fiber receiving structure. A suitable polymer or compound 1527, selected according to its acoustic and mechanical properties, may be used to secure the fiber 1501D to needle 1500D. The suitable polymer or compound 1527 may be selected according to its acoustic and mechanical properties, for example, the speed of sound, acoustic impedance, thermal conductivity, water proofing, etc. The suitable polymer or compound 1527 may also offer modification of acoustic impedance matching to the surrounding medium in addition to the mechanical fixing and protection of the sensor on its surface. Likewise, as shown in FIG. 20D, a sheath 1520D may be used to secure the sensor fiber to the needle body 1505D. The sheath 1520D is configured to wrap around the needle body 1505D. The sheath 1520D may mechanically secure the sensor fiber 1501D to the needle body 1505D. The sheath may wrap around the needle in a manner that allows some movement of the fiber to be within the sheath. This can allow bending/flexibility of the needle. In embodiments, the sensor fiber 1501D may be secured at least partially by both a sheath 1520D and a polymer or compound 1527. Such an arrangement may permit relative movement between the sensor fiber 1501D and the needle body 1505D, thus providing potential strain relief in the event of needle bending. This embodiment may further include a window in the manner of the other embodiments incorporating a window, A potting compound or polymer may be used to further secure the fiber located within the window in the manner of the earlier embodiments.

Figure 21:
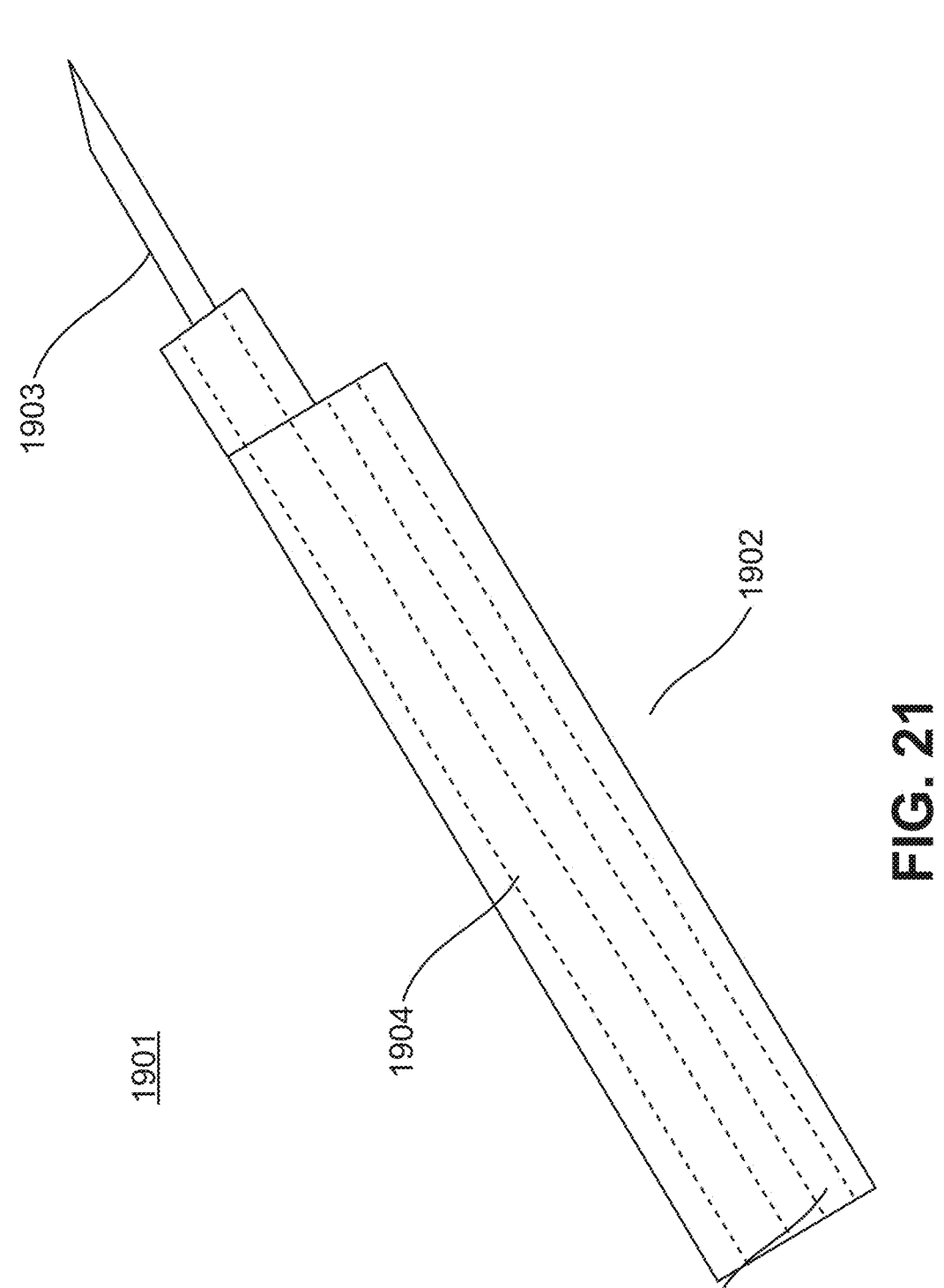
FIG. 21 illustrates a medical device distal end incorporating a catheter delivered needle according to embodiments hereof.

FIG. 21 illustrates a medical device distal end incorporating a fiber end sensor according to embodiments hereof. The medical device distal end 1901 includes a catheter 1902 and a medical tool, such as needle 1903. The catheter 1902 is configured to carry the needle 1903 (e.g., provide access through a lumen through which the needle may be conveyed) to a treatment and/or diagnosis site via the lumen 1904. The catheter 1902 may further include a guidewire lumen 1905 configured to guide the catheter 1902 along a guidewire to the treatment and/or diagnosis site. The needle 1903 is configured to be extended (e.g., by an operator, human or robotic) from the lumen 1904 of the catheter 1902 upon reaching the treatment and/or diagnosis site. In embodiments, the needle 1903 may be configured similarly to the needle 1500, including one or more sensor fibers 1501 disposed on or integrated therewith. In embodiments, the catheter 1902 may include one or more sensor fibers and one or more acoustic transducers disposed on or integrated therewith. In embodiments, the one or more sensor fibers 1501 may be used to sense, monitor, and/or track a location of the needle 1903 (for example, based on acoustic signals generated by acoustic transducers/probes located exterior to the medium in which the catheter 1902 is being used. The one or more sensor fibers 1501 and the one or more acoustic transducers disposed on the catheter 1902 may be used to generate images, e.g., through detection of acoustic echoes by the one or more sensor fibers. The one or more acoustic transducers may generate acoustic signals while the one or more sensor fibers receive echoes or reflections of the acoustic signals based on their interaction with the surrounding medium. The acoustic transducers will also receive reflected or scattered acoustic signals and/or tissue harmonics which may then be used to create an image of the surrounding area to which the tracking information will be added.

Figure 22:
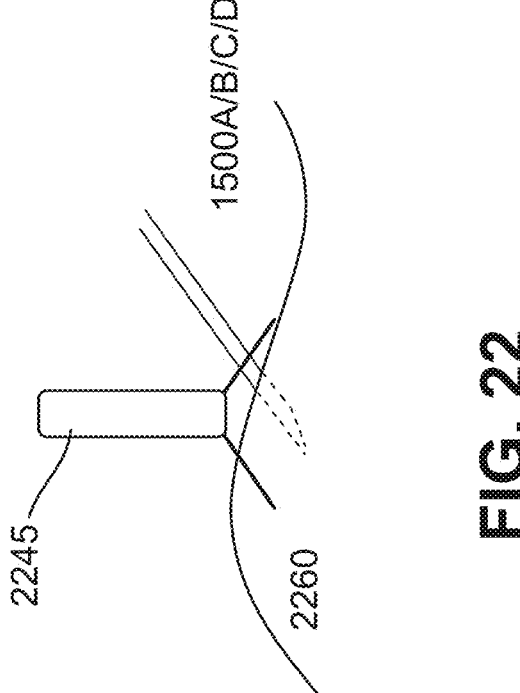
FIG. 22 illustrates uses of a fiber based optical sensor in needle guidance or location according to embodiments herein.

FIG. 22 illustrates an example use of a fiber based optical sensor incorporated into a needle. The uses shown may incorporate needle 1500A, needle 1500B, 1500C, 1500D, or any suitable needle that incorporates a fiber based optical sensor. As shown in FIG. 22, an external acoustic probe 2245 may be employed with a needle 1500A/B/C/D that incorporates a fiber based optical sensor. As discussed herein, in an embodiment for location/guidance, the fiber based optical sensor may receive acoustic signals generated by the external acoustic probe 2245. These acoustic signals may then be used, alone or in combination with reflected acoustic signals captured by the acoustic probe, to determine a location of the needle within the medium 2260 (e.g., the patient's body).

Figure 23B:
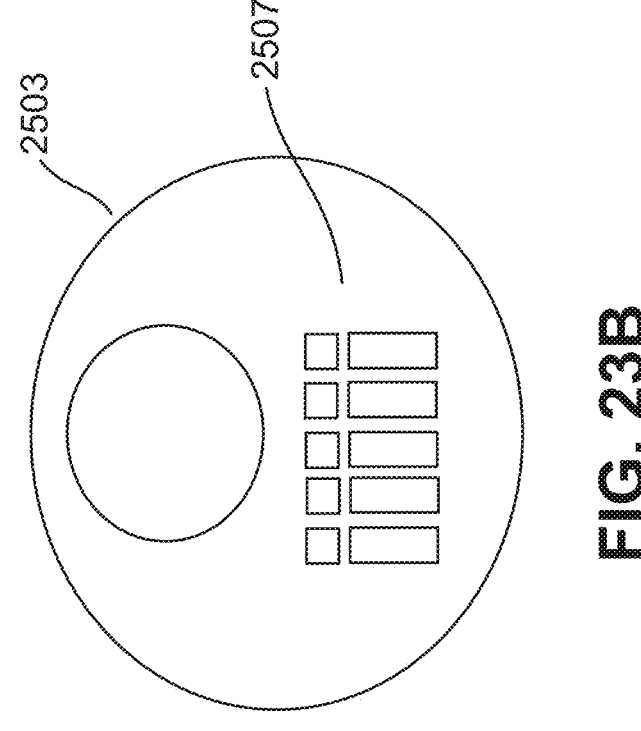
FIGS. 23A-23B illustrate a catheter delivered needle incorporating a fiber based optical sensor according to embodiments herein.
Figure 23A:
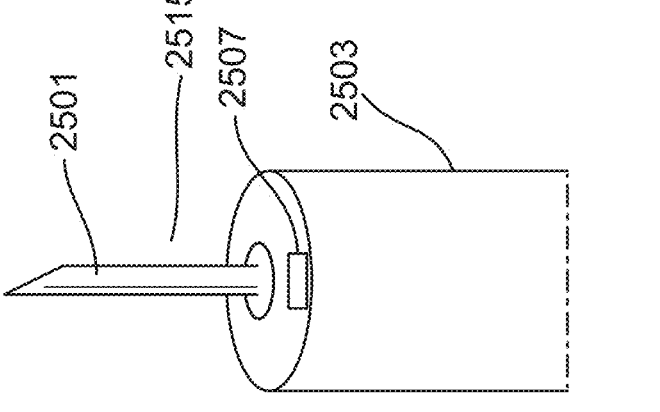

FIGS. 23A-23B illustrate embodiments of a fiber based optical sensor incorporated into a catheter delivered needle. A catheter delivered needle may be used, for example, for biopsy procedures. A needle 2515 may be delivered to a procedure site via a catheter 2503. The needle 2515 may incorporate a fiber based optical sensor 2501, as described in various embodiments herein. Upon delivery to a procedure site via the catheter 2503, the needle 2515 may be extended from a lumen in the catheter 2503 to perform the procedure. The needle 2515 may be monitored, guided, and or located, through the use of one or more external acoustic transducers that provide acoustic signals that are received by the fiber based optical sensor 2501. The acoustic transducers may be associated, e.g., with an optical sensor system. The optical sensor system, which may be an example of various optical sensor systems described herein, may provide the necessary processing and signal generation/reception requirements to perform the optical acoustic signal sensing methods described herein. In further embodiments, as illustrated in FIG. 23B, the catheter 2503 may include one or more additional transducers. For example, the catheter may include a mixed sensor array 2547 that includes one or more of an AEG (or other suitable acoustic transducer array) array 2548 and a PIC (photonic integrated circuit) optical sensor array 2549. In embodiments, the mixed sensor array 2547 may include any suitable fiber optical sensors discussed herein, including, for example, fiber-end sensors and polarization based sensors in addition to or in place of PIC optical sensor array 2549. In embodiments, US Application Publication 20230148869, filed on Nov. 18, 2022, entitled Mixed Ultrasound Transducer Arrays and incorporated herein by reference; US Application Publication US20220350022, filed on Apr. 29, 2021, entitled Modularized Acoustic Probe and incorporated herein by reference, and U.S. Application No. 63/550,515, filed on Feb. 6, 2024 and incorporated by reference disclose various optical sensors that may be used in a mixed transducer array. The PIC array 2549 may be adapted for detection of acoustic signals. Similar to the fiber end sensors discussed herein, the PIC array 2549 may be adapted for detection of acoustic signals by measuring or detecting changes in the optical characteristics of the PIC array 2549 that result from the incidence of acoustic signals. In embodiments, acoustic signal data captured variously by the fiber based optical sensors 2501, PIC array 2549, AEG array 2548, and external acoustic transducers may be used in any combination by the optical sensor system to monitor, guide, and locate the needle 2515 (and the catheter 2503 adapted to deliver it) as well as to generate images of the medium in which the catheter 2503 is deployed (e.g., a procedure site).

In further embodiments, fiber based optical sensors consistent with embodiments herein may be employed in various additional uses. For example, fiber based optical sensors may be used for tracking a cannula configured with an optical camera and moveable ultrasound transducer used in vivo during a minimally invasive surgery. In another embodiment, a transcutaneous or percutaneous ultrasound probe may be configured with one or more fiber based optical sensors according to embodiments hereof. In another embodiment, a guide wire may be configured with one or more fiber based optical sensors according to embodiments hereof. In another embodiment, a stylet may be configured with one or more fiber based optical sensors Embodiments of mixed sensor arrays are presented in FIG. 24A through FIG. 40. Generally, the mixed sensor arrays (e.g., including both AEG elements and fiber optical sensors) may be incorporated into mixed sensor transducers which may be used in any appropriate ultrasound environment, including at least handheld probe heads, intravascular ultrasound (IVUS), intraluminal ultrasound, endoluminal ultrasound (EUS), endobronchial ultrasound (EBUS), intraoperative ultrasound (IOUS), endoscopic ultrasound, robotic ultrasound probe heads, and others. As discussed herein, the mixed sensor arrays may operate by employing the AEG elements to generate acoustic signals (e.g., ultrasound) and employing both the AEG elements and the fiber optical sensors to receive reflected acoustic signals. In some embodiments, the AEG elements are optimized for transmission of acoustic signals and may or may not operate to receive acoustic signals. Mixed sensor arrays described herein may further include fiber optical sensors configured to measure, sense, and/or detect physical parameters. In additional embodiments, mixed sensor arrays described herein may include fiber optical sensors having different physical parameters sensitivities, as discussed above, to improve physical parameter measurements. Processing systems associated with these mixed sensor arrays may then be used to interpret the received acoustic signals and provide ultrasound images and/or data related to sensed physical parameters. The sizes and shaped of probe heads illustrated in FIG. 24A through FIG. 40 are provided by way of example only. For example, FIGS. 26A and 26B illustrate a mixed sensor transducer probe 2500 that may be suitable for external or ex vivo use. In embodiments for alternative uses, e.g., intravascular ultrasound (IVUS), intraluminal ultrasound, endoluminal ultrasound (EUS), endobronchial ultrasound (EBUS), intraoperative ultrasound (IOUS), endoscopic ultrasound, etc., mixed sensor transducer probes incorporating the various embodiments discussed herein may be provided with appropriate form factors (for example, having smaller mixed sensor arrays and being configured for deployment via catheter, guidewire, endoscope, or other device intended for internal or in vivo use.)

Generally, in embodiments, a mixed sensor array apparatus for imaging a target may include an ultrasound transducer array that includes one or more array elements of a first type and one or more array elements of a second type different from the first type. The first type may be a transducer (e.g., AEG materials including, for example, piezoelectric materials such as lead-zirconate-titanate (PZT), ceramic, piezoelectric single crystal (e.g., PIN-PT, PIN-PMN-PT), polymer thick film (PTF), polyvinylidene fluoride (PVDF), capacitive micromachined ultrasonic transducers (CMUT), piezoelectric micromachined ultrasound transducers (PMUT), among many other materials among many other materials configured to transmit acoustic waves, and the second type may be any optical sensor described herein (e.g., an interference-based optical sensor such as an optical resonator, an optical interferometer, etc.) to detect acoustic signals (such as echoes or reflections) corresponding to the transmitted acoustic waves. In some embodiments the array elements of the first and second types are configured to detect acoustic signals. In embodiments, the array elements of the first type are configured to transmit and detect acoustic signals and the array elements of the second type are configured to detect acoustic signals. In embodiments, a mixed ultrasound imaging probe comprises an AEG material subarray and a fiber optic sensor array, which may include, for example, a photonic integrated circuit (PIC) receiver subarray or a structured collection of individual fiber optic sensors (each of which may be referred to as an optical subarray), as discussed below. In embodiments, mixed ultrasound imaging probes may include mixed sensor arrays discussed herein enclosed and incorporated within a suitable housing.

Generally, mixed sensor arrays may provide an improvement over conventional AEG-only transducers by permitting reception of ultrasound at wider bandwidths and greater incident angles. As discussed herein, fiber optical sensors may be configured to receive a wider bandwidth of reflected acoustic signals, for example, those signals created by tissue harmonics (e.g., returned acoustic signals at integer multiples of a transmitted acoustic frequency), thereby permitting potentially greater resolution of tissue imaging. The ability to receive signals in a wider bandwidth may improve axial resolution due to a shorter pulse length caused by the use of higher frequency signals (e.g., tissue harmonics). For example, a 5 MHz acoustic signal may induce tissue harmonics at 10 MHz, 15 MHz, 20 MHz, 25 MHz or higher. An AEG transducer that is optimized to transmit at a particular frequency (e.g., 5 MHz) may not be suited to receive signals at other frequencies (10 MHz, 15 MHz, 20 MHz, 25 MHz). Use of an AEG transducer in a transmit-only mode may permit the AEG transducer to be optimized for transmission at a first frequency while an optical acoustic sensor according to embodiments herein is optimized for reception across a wide bandwidth of higher frequencies that may result from tissue harmonics.

Further, as discussed herein, fiber optical sensors may have a wider reception angle, which may further provide imaging advantages. For example, a wider reception angle may improve lateral resolution due to the existence of a larger aperture that can improve the diffraction limit. Further, such wider reception angles may benefit doppler imaging techniques as well as increase usable angular ranges for beam steering. Additionally, as discussed herein, due to the small size of acoustic optical transducers discussed herein, larger reception angles may be achieved without requiring a very large array (as may be the case with AEG reception arrays).

Mixed sensor arrays may further permit improvements and/or alterations to transducer housings that might function poorly with AEG only transducers. For example, because optical acoustic sensors as discussed herein are not sensitive to electromagnetic interference (EMI), transducer housings may be made thinner, lighter, and less expensive, because EMI shielding is only required for the AEG transducer component. The reduction/elimination of EMI that may be realized with optical acoustic sensors may also improve the performance of optical acoustic based reception transducers.

Other benefits of mixed sensor arrays resulting from the use of one type of sensor array (for example, AEG arrays) to transmit and a second type (for example, acoustic optical sensors) to receive may result from optimizing the positioning of the separate transmit and receive transducers. By altering the locations of the separate transducers with respect to one another, improved imaging may be achieved. For example, separating the transmit and receive transducers may permit a reduction in edge diffraction (side lobing).

Additionally, mixed sensor arrays may provide the benefit of multi-dimensional sensing provided by fiber optic sensors incorporated therein. As discussed above, fiber optic sensors may be configured to measure, detect, and/or sense physical parameters beyond acoustic signals. Incorporating such fiber optic sensors into mixed sensor arrays may provide for greater flexibility in the use of mixed sensor array probes by permitting the same sensors to detect and/or measure additional physical parameters. In embodiments, each of the mixed sensor arrays described with respect for FIGS. 24A-35C and 39A-39C may be further configured with multi-dimensional sensing capabilities, including the use of sensor fibers having differing physical sensitivities. Additionally, each of the systems described with respect to FIGS. 36-38 and FIG. 40 may include processing systems configured to and capable of interpreting optical signals from mixed sensor arrays to measure physical parameters in addition to acoustic signals.

Figures 24A, 24B:
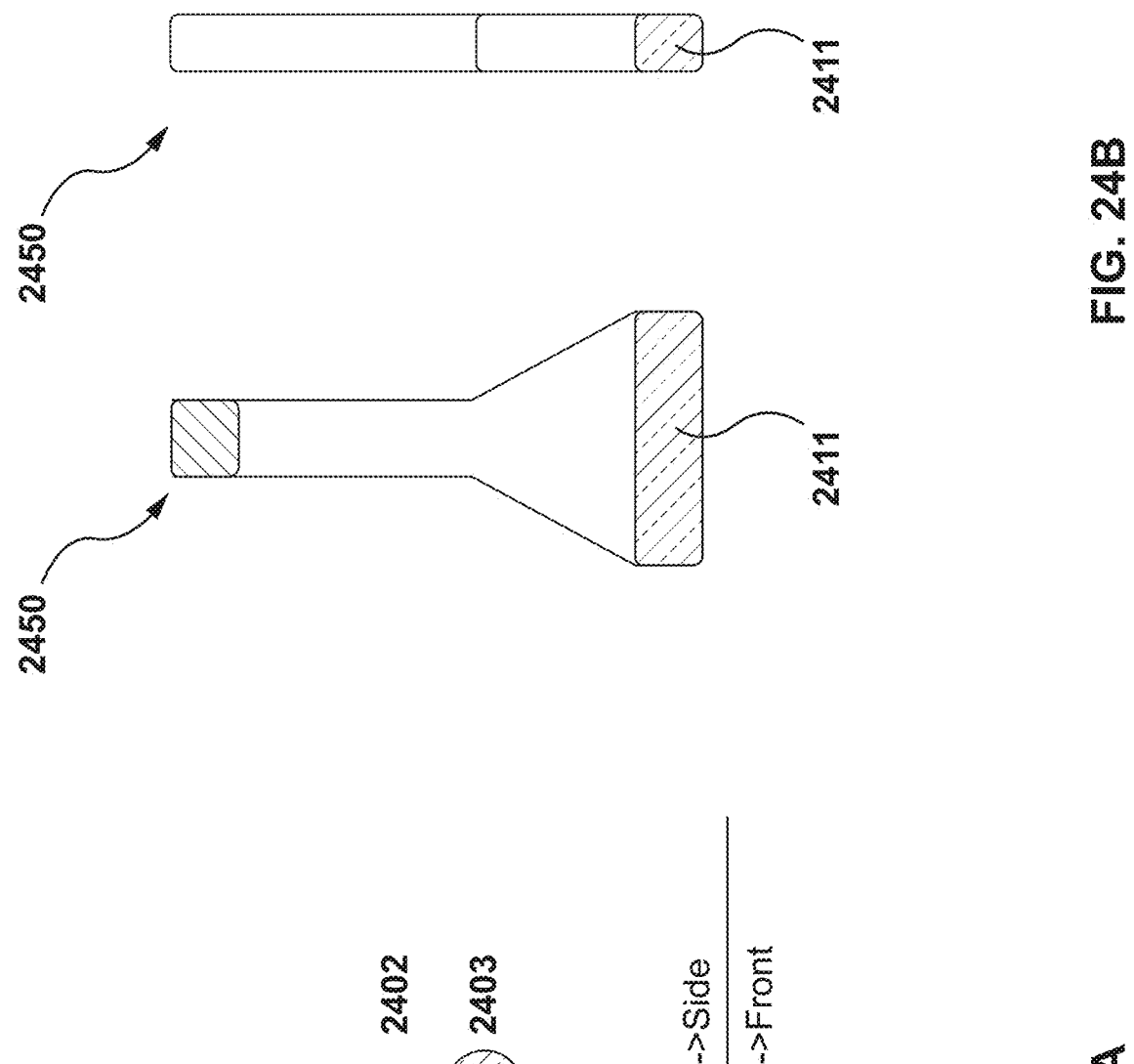
FIGS. 24A and 24B illustrate embodiments including a mixed sensor probe and mixed sensor array according to embodiments herein.

FIGS. 24A and 24B illustrate a mixed sensor probe and a mixed sensor array according to embodiments hereof. In an embodiment, as shown in FIG. 24A, the mixed sensor probe 2401 includes an array of one or more AEG elements 2403 arranged circumferentially around a fiber optical sensor 2402. The fiber optical sensor 2402 may include any of the fiber optical sensors (e.g., fiber end sensors) discussed herein. The mixed sensor probe 2401 may be used in conjunction with any suitable optical acoustic sensor system (e.g., system 200) described herein. In further embodiments, as shown in FIG. 24B, a mixed sensor probe 2450 may include a mixed sensor array 2411, which may include a plurality of fiber optical sensors in combination with an array of one or more AEG elements.

Figures 24C, 24D:
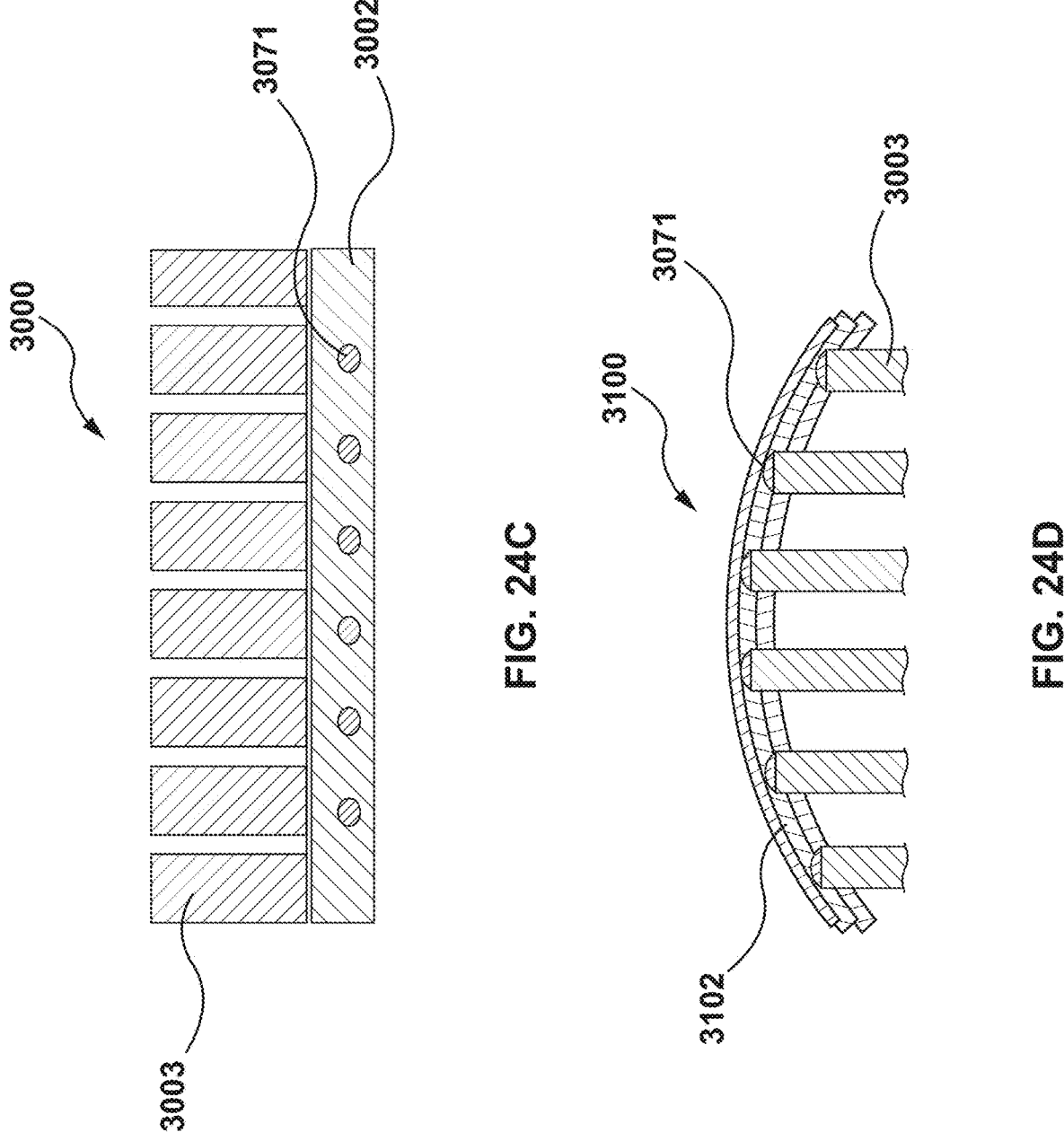
FIGS. 24C and 24D illustrate additional embodiments of mixed sensor array transducers according to embodiments herein.

FIGS. 24C and 24D illustrate additional embodiments of mixed sensor array transducers. The mixed sensor array transducer 3000 and the mixed sensor array transducer 3100 are arrays of multiple fiber sensors 3071 arranged in a transducer head. The fiber sensors 3071 may be any fiber sensors described herein and, in particular, may be fiber end sensors consistent with embodiments hereof. The mixed sensor array transducer 3000 and the mixed sensor array transducer 3100 may each also include AEG elements to generate acoustic signals. The mixed sensor array transducer 3000 includes a fiber optic sensor substrate 3002 to capture the fiber optical sensor 3071 and a plurality of AEG elements 3003. The fiber optic sensor substrate 3002 may include a structure configured to hold the fiber sensors 3071. A probe head including the mixed sensor array transducer 3000 may further include appropriate structures and materials to form an interface layer which may further include matching layers, a couplant and an acoustic lens. The fiber sensor array transducer 3000 is a linear structure and forms a linear sensor array. The fiber optic sensor substrate 3102 is similar to the transducer head substrate 3002 and may include the same elements. The fiber optic sensor substrate 3102 is curved and provides a curvilinear array and is incorporated into the mixed sensor array transducer 3100. AEG elements of the mixed sensor array transducer 3000 are not shown.

Any of the mixed sensor array transducers described herein may be linear or curvilinear. Curvilinear arrays may provide benefit or a wider field of view and better contact for a probe head incorporating these. Linear arrays may provide benefits related to ease of manufacture. Further, the broad field of view of fiber optical sensors described herein may at least partially make up for the narrower field of view associated with the linear structure.

FIGS. 25A, 25B, 25C, 25D, and 25E illustrate additional embodiments of mixed sensor arrays according to embodiments hereof. The mixed sensor array embodiments of these Figures may be configured to include fiber optical end sensors as discussed herein and/or any other fiber optical sensor discussed herein. Each of FIGS. 25A-25E illustrate the face of a mixed sensor transducer array, e.g., the face from which acoustic energy is emitted and received. Although the mixed sensor transducer array faces are illustrated as circles and rectangles, suitable variations of these shapes may be used without departing from the scope of the invention. Mixed sensor arrays disclosed herein are not drawn to scale. Because fiber optical sensors disclosed herein may be as much as ten to twenty or more times smaller than AEG elements (e.g., 125 microns vs 3 mm in a linear dimension), the associated arrays may also be smaller. Arrays illustrated and described herein may include any appropriate number of sensors and may include sensors arranged in more than one row, column, line, etc. A "linear" array, as described herein, is not required to be a single line of sensors, but generally denotes the shape of the array as a whole extending further in a first dimension than a second. The number of sensors and the spacing (e.g., pitch) therebetween in the following sensor arrays may vary according to applications. In examples, the pitch may be selected as approximately a quarter wavelength or a half-wavelength of expected incoming acoustic waves.

Figures 25A, 25B, 25C, 25D:
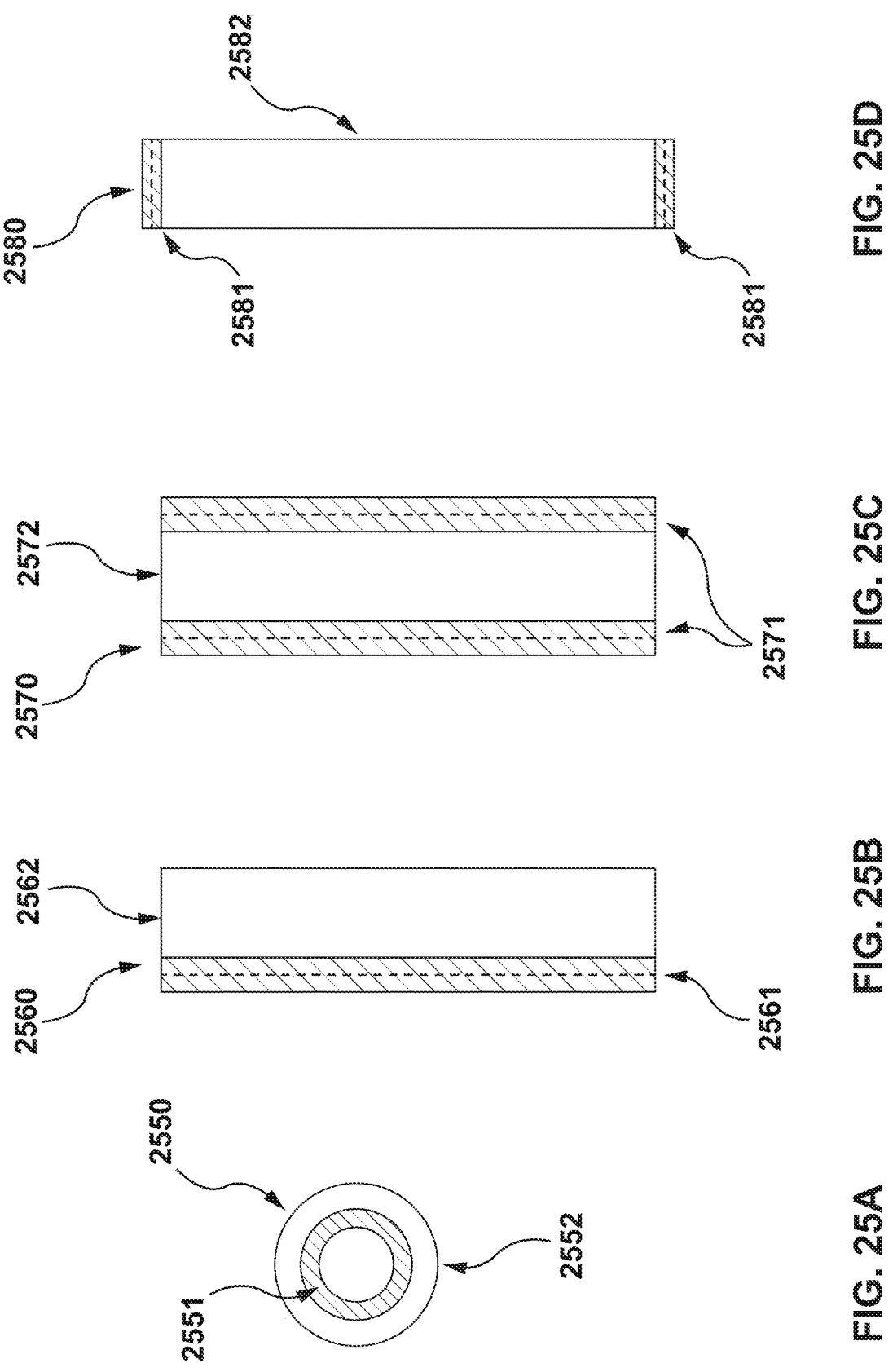
FIG. 25A illustrates a concentric mixed sensor array according to embodiments herein.
FIG. 25B illustrates a linear mixed sensor array according to embodiments herein.
FIG. 25C illustrates a linear mixed sensor array according to embodiments herein.
FIG. 25D illustrates a linear mixed sensor array according to embodiments herein.
Figure 26B:
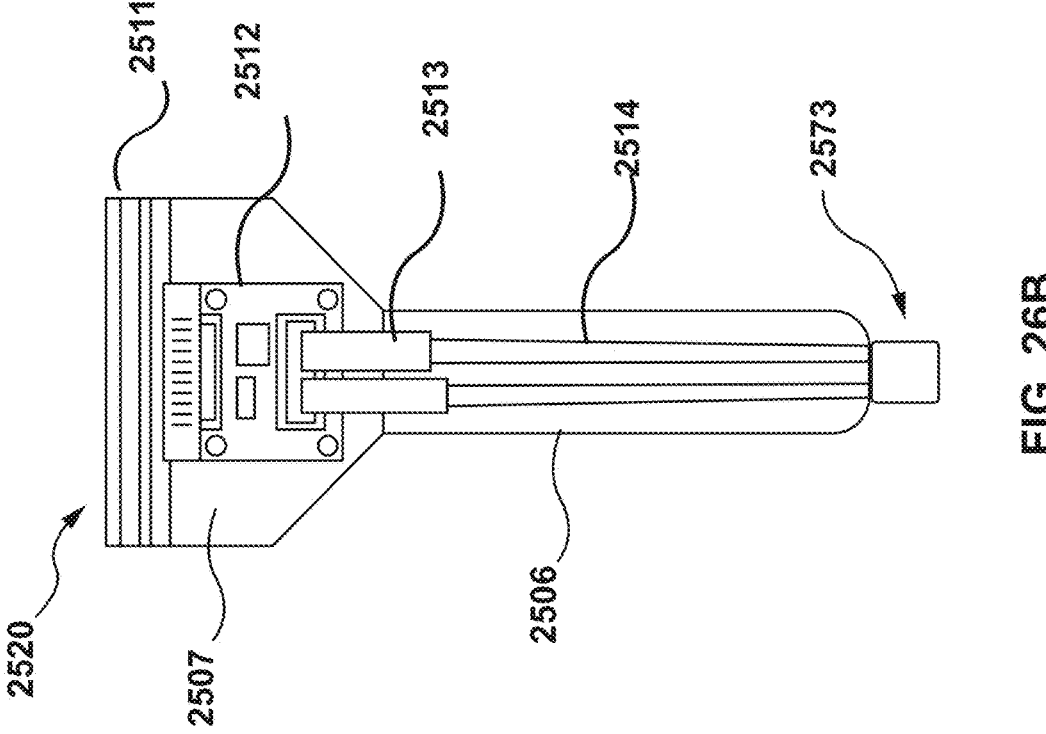
FIGS. 26A and 26B illustrate a mixed sensor transducer probe according to embodiments herein.
Figure 26A:
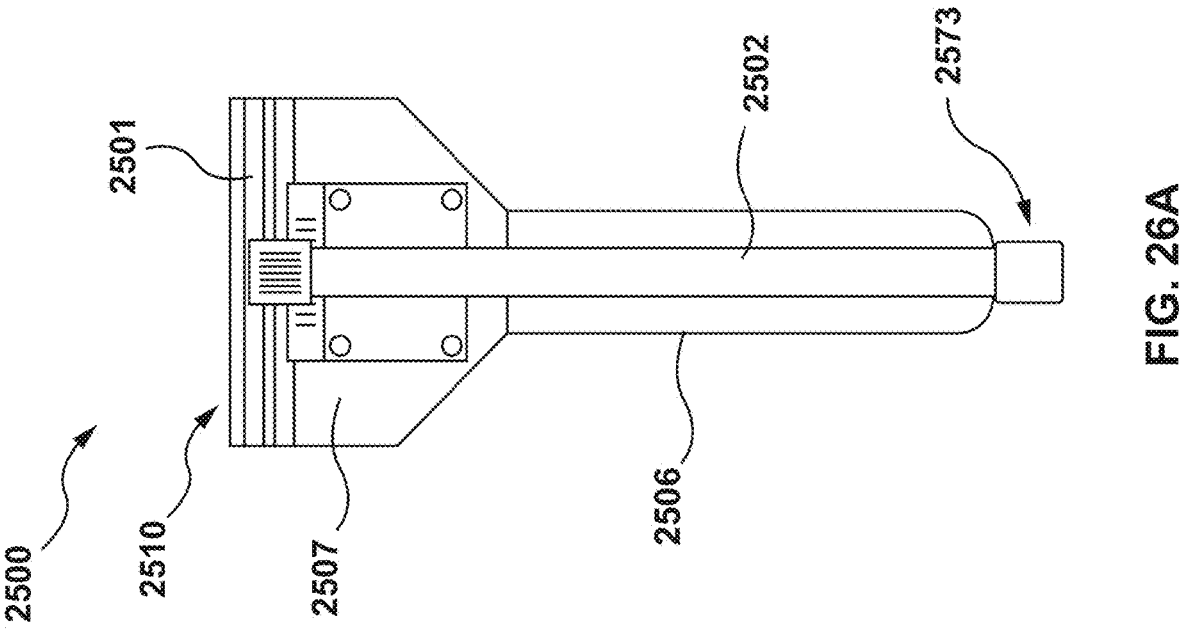

FIG. 25A illustrates a concentric mixed sensor array 2550. A plurality of fiber optical sensors may be arranged in a ring shape to form a fiber optical sensor array 2551. A plurality of AEG elements may be arranged concentrically in a ring shape surrounding the fiber optical sensor array 2551 to form an AEG element array 2552. In embodiments, the relative positioning of the fiber optical sensor array 2551 vs the AEG element array 2552 may be reversed. The concentric mixed sensor array 2550 may provide an array with a reduced footprint as compared to linear arrays discussed herein.

FIG. 25B illustrates a linear mixed sensor array 2560. A plurality of fiber optical sensors may be arranged linearly to form a fiber optical sensor array 2561 along a long dimension of the mixed sensor array 2560. A plurality of AEG elements may be arranged linearly substantially parallel (e.g., within 10% of parallel) to the fiber optical sensor array 2561 to form an AEG element array 2562. In this embodiment, a single fiber optical sensor array 2561 and a single AEG element array 2562 may be provided. The linear mixed sensor array 2560 provides an array with ease of manufacture.

FIG. 25C illustrates a linear mixed sensor array 2570. A plurality of fiber optical sensors may be arranged linearly to form two fiber optical sensor arrays 2571, substantially parallel to one another along a long dimension of the mixed sensor array 2570. A plurality of AEG elements may be arranged linearly substantially parallel to the fiber optical sensor arrays 2571 to form an AEG element array 2572. The linear mixed sensor array 2570 may provide an array with increased field of view as well as "1.5 D" imaging. 1.5 D imaging provides additional imaging information in the elevational dimension (e.g., a wider elevational aperture) by using two different fiber optical sensor arrays 2571 displaced from one another in the elevation dimension of the sensor array.

FIG. 25D illustrates a linear mixed sensor array 2580. A plurality of fiber optical sensors may be arranged linearly to form a fiber optical sensor array 2581, substantially parallel to one another along a short dimension of the mixed sensor array 2580. A plurality of AEG elements may be arranged linearly substantially perpendicular (e.g., within 10% of parallel) to the fiber optical sensor arrays 2581 to form an AEG element array 2582. The linear mixed sensor array 2580 provides an array with an increased field of view as well as "1.5 D" imaging. 1.5 D imaging provides additional imaging information in the elevational dimension (e.g., a wider elevational aperture) by using fiber optical sensor arrays 2581 that extend in the elevation dimension of the sensor array.

In some embodiments, a mixed sensor array may include the fiber optical sensor arrays 2571 and 2581 to create a "box-like" fiber optical sensor array providing increased field of view in multiple dimensions.

Figure 25E:
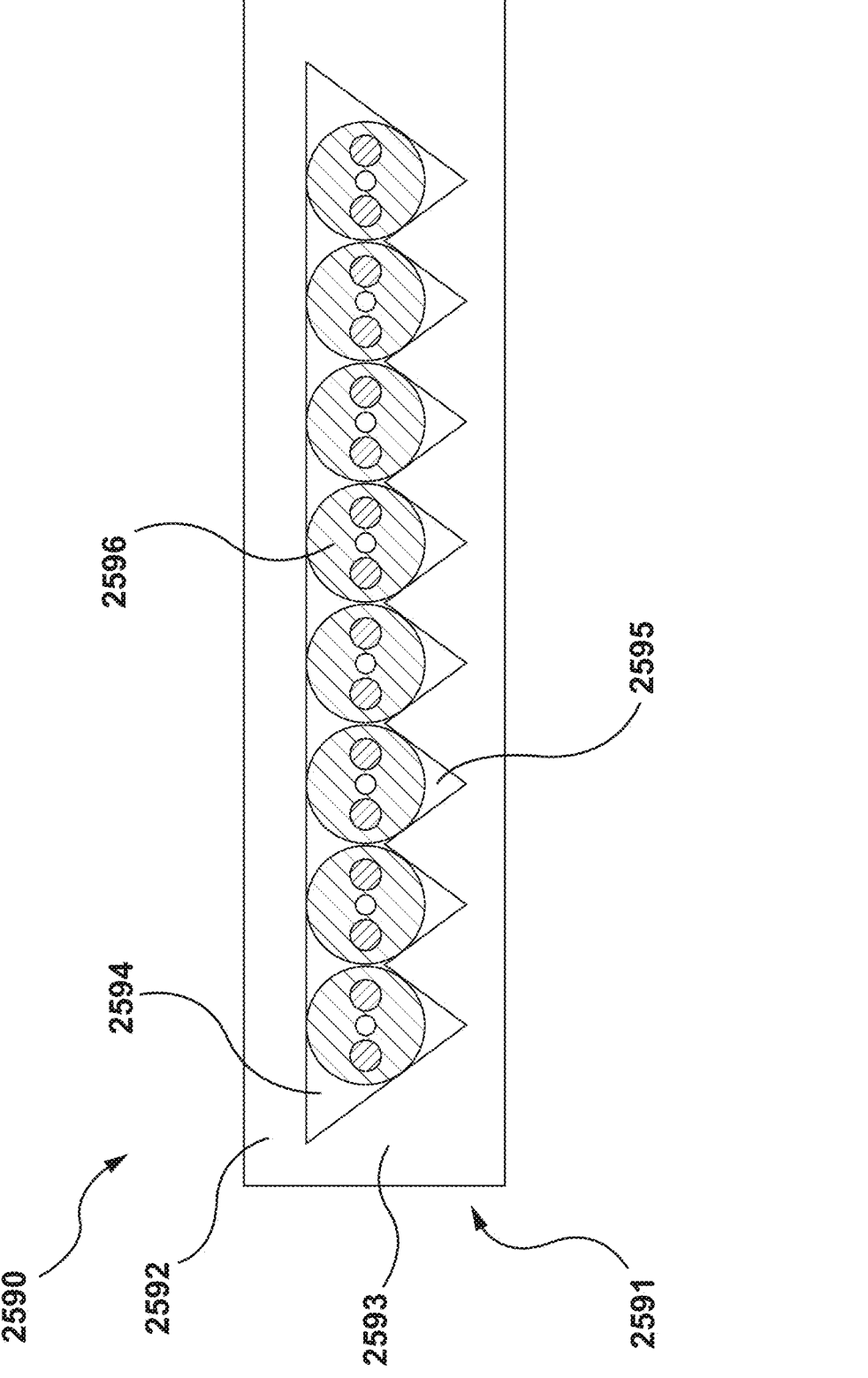
FIG. 25E illustrates an example of a structure securing fiber optical sensors within an array for incorporation into a mixed sensor array according to embodiments herein.

FIG. 25E illustrates an example of a structure securing fiber optical sensors within an array for incorporation into a mixed sensor array. The structure of the mixed sensor array 2590 may be configured or adapted for incorporation within any mixed sensor array discussed herein. The mixed sensor array 2590 may include a substrate 2591 having a first portion 2592 and a second portion 2593. The substrate 2591 may include a polymer or any suitable material. Sensors may include silica or germanium doped chalcogenide. The substrate 2591 may include hard plastic, acrylic, glass, silicon. Preferably, rigid and thermally insensitive materials may be selected. The second portion 2593 may be configured with one or more fiber optic sensor receiving portions 2595, which may be grooves, channels, notches, trenches, depressions, openings or holes, etc., in the second portion 2593 that provide a space for arranging the fiber optic sensors 2596. An epoxy, resin, or other adhesive 2594 may be deposited around the fiber optic sensors 2596 arranged in the receiving portions 2595. The adhesive 2594 may include, for example, but not limited to, polymer epoxies exhibiting low shrinkage and optical grade qualities (e.g., transparency). The first portion 2592 may be applied as a "lid" to complete the capture of the fiber optic sensors 2596. In embodiments, the first portion 2592 is not required and the fiber optic sensors 2596 may be secured with only the adhesive 2594. In embodiments, the adhesive 2594 is not required, and the fiber optic sensors 2596 may be secured only via the mechanical clamping of the lid 2592. The substrate 2591 serves to capture the fiber optic sensors 2596 and to maintain appropriate positioning and distancing therebetween when employed in a mixed sensor array.

FIGS. 26A and 26B illustrate a mixed sensor transducer probe. The mixed sensor transducer probe 2500 may be suitable for external use and may include any of the mixed sensor arrays and their associated components as described herein. The mixed sensor transducer probe 2500 may include two components—an optical acoustic transducer 2510 and an AEG based transducer 2520. These two components are illustrated here as separate portions for ease of discussion. It is understood that the features of these two components may be mixed and intermingled as necessary for functionality, as discussed in greater detail below.

The optical acoustic transducer 2510 may include a fiber optical sensor array 2521 (which may be any fiber optical sensor array disclosed herein) including one or more fiber optical sensors consistent with embodiments hereof contained within a probe head 2507 of the mixed sensor transducer probe 2500. The optical acoustic transducer 2510 may further include an optical waveguide 2502 (e.g., fiber optic cable) disposed within a handle 2506 of the mixed sensor transducer. The optical sensor array 2521 and optical waveguide 2502 may be optically coupled to the light source through the use of an optical sensor circuit such as that disclosed in U.S. application Ser. No. 18/429,517, titled Optical Sensor Circuit and Optical Sensing Method, filed Feb. 1, 2024 and incorporated by reference. Such an arrangement would further require a component such as a fan out coupler on the probe head to direct the light to and from the various sensors on the array. The AEG based transducer 2520 may include an AEG transducer stack 2511 comprising one or more AEG transducers and components necessary for their operation contained within a probe head 2507 of the mixed sensor transducer probe 2500. The AEG based transducer 2520 may further include a circuit 2512, such as a flex circuit, interconnect 2513, and connection cable 2514 (e.g., coaxial cable or the like). These may be disposed within a handle 2506 of the mixed sensor transducer probe 2500 and/or within the probe head 2507, as necessary. The mixed sensor transducer probe 2500 may further include a mixed cable 2573 configured to carry both the optical waveguide 2502 and the connection cables 2514 back to a system.

Figure 27A:
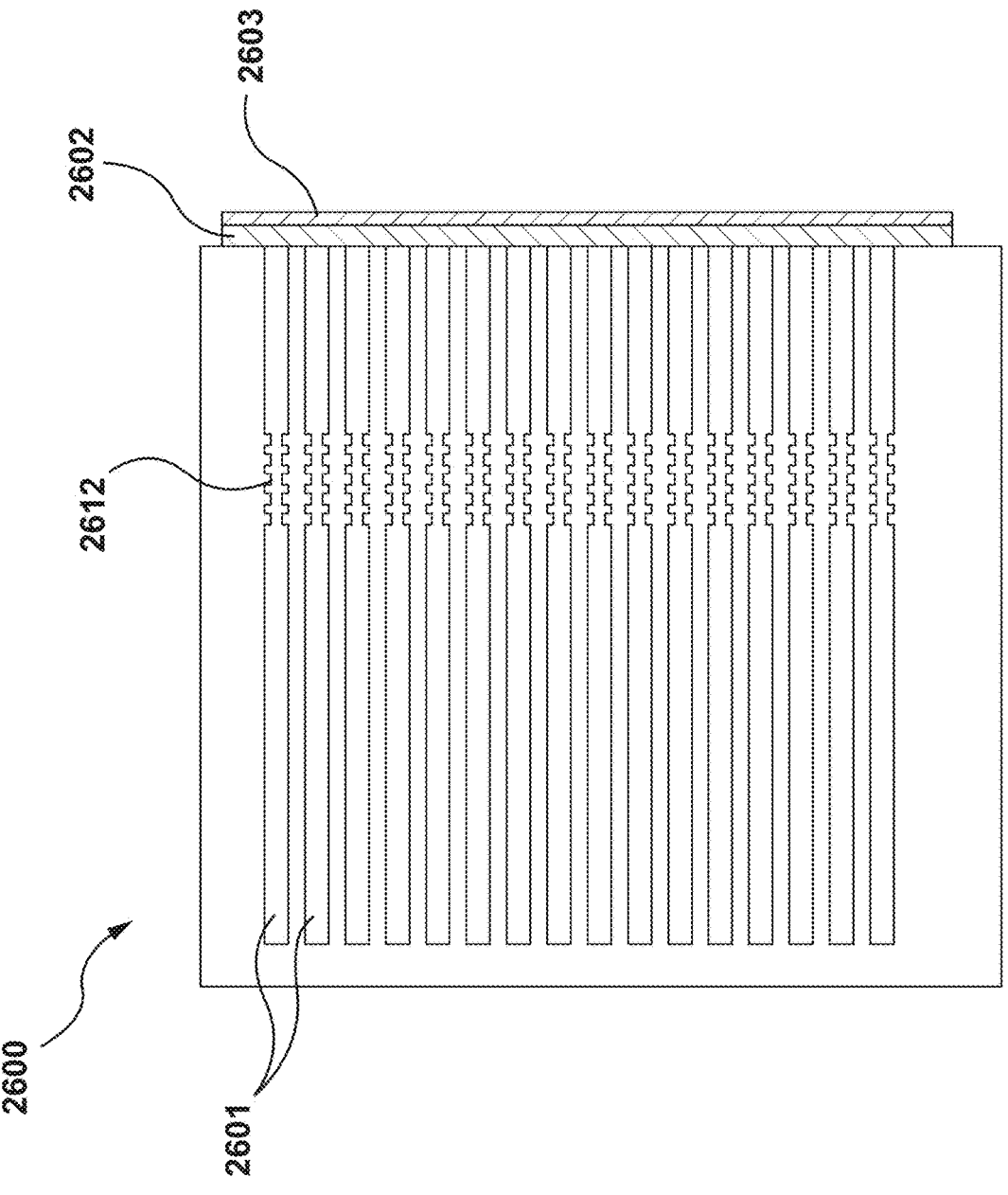
FIGS. 27A and 27B illustrate an on-chip fiber optical sensor array according to embodiments herein.
Figure 27B:
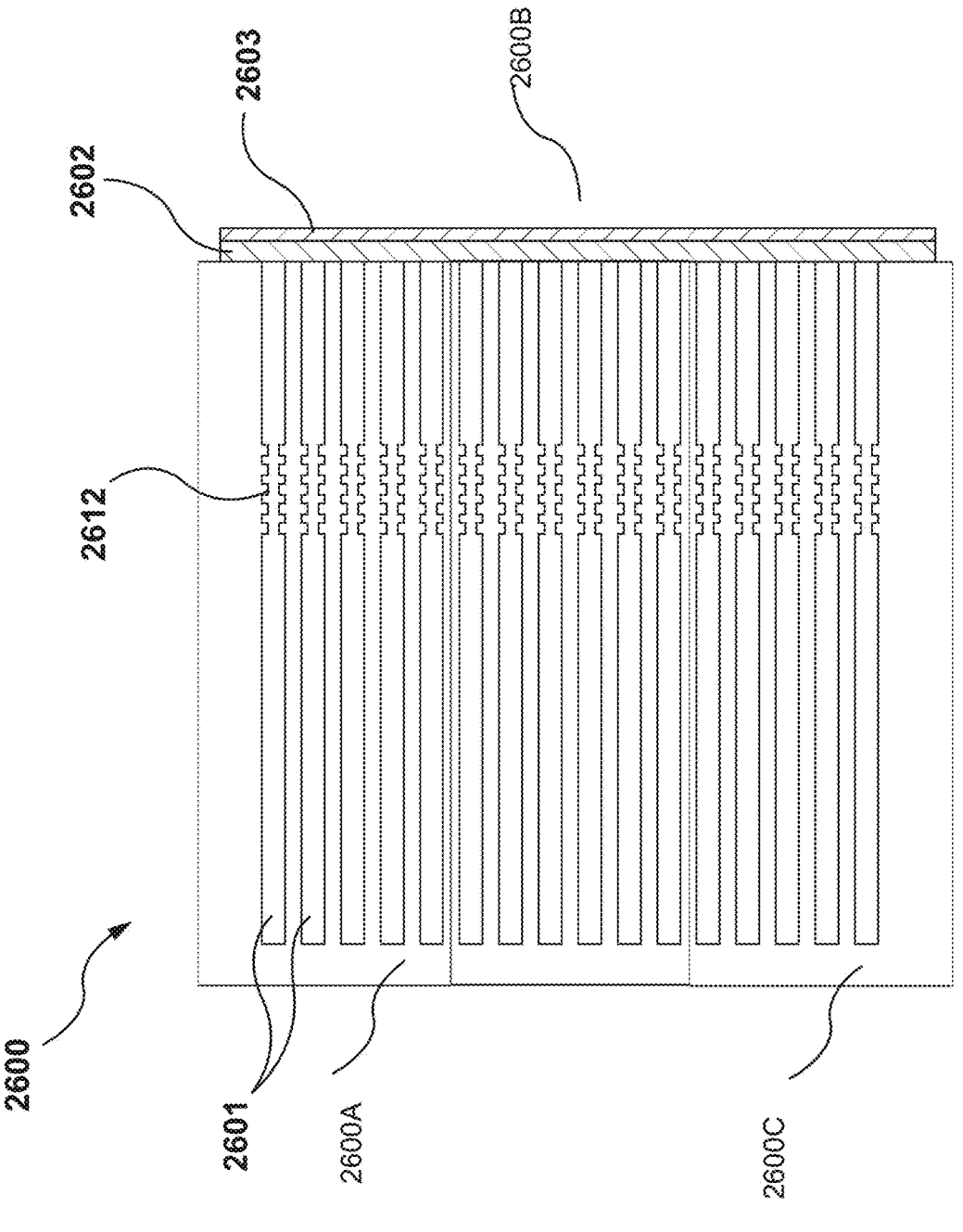

In embodiments, the fiber optical sensor array 2521 may include a bundle of fiber optical sensors, as disclosed herein. In further embodiments, the fiber optical sensor array 2521 may include an on-chip fiber optical sensor array 2600, as shown in FIG. 27A. FIG. 27A illustrates an on-chip fiber optical sensor array 2600 may include an array of fiber optical sensors formed together on a single chip. In an embodiment, the on-chip fiber optical sensor array 2600 may include a plurality of optical waveguides 2601 (which may be fiber optic cores, for example) sharing a distal reflecting surface 2603 and an acoustically sensitive polymer portion 2602. The distal reflecting surface 2603 and an acoustically sensitive polymer portion 2602 stretch across the entirety of the sensor array 2600. This design is similar to the interferometer based fiber-end sensor structure 321A of FIG. 5B. In further embodiments, any suitable fiber end optical sensor structure of the current disclosure may be suitable for the on-chip fiber optical sensor array 2600. In embodiments, each of the optical waveguides 2601 may include a Bragg grating 2612. In embodiments, the fiber optical sensor array 2600 may be manufactured by mounting individual optical fibers to the substrate, optionally performing one or more operations to smooth the faces of the optical fibers, and then applying the distal reflecting surface 2603 and the acoustically sensitive polymer portion 2602. In embodiments, the fiber optical sensor array 2600 may be manufactured, e.g., through the use of UV lithography or other suitable additive manufacturing technique to write the optical waveguides 2601. Accordingly, in embodiments, at least a portion of the fiber optical sensor array 2600 may be formed of the chip (e.g., the substrate) itself. In other embodiments, as shown in FIG. 27B, the fiber optical sensor array 2600 may be formed from a plurality of fiber optical sensor arrays 2600A, 2600B and 2600C forming one array 2600. Each of fiber optical sensor arrays 2600A, 2600B and 2600C may be formed on individual chips or substrates and arranged side by side to form a single array 2600. In embodiments, the distal reflecting surface 2603 and the acoustically sensitive polymer portion 2602 may be applied continuously across the multiple fiber optical sensor arrays 2600A/B/C (as shown in FIG. 27B). In embodiments, the distal reflecting surface 2603 and the acoustically sensitive polymer portion 2602 may be applied individually to each of the multiple fiber optical sensor arrays 2600A/B/C prior to their alignment. The fiber optical sensor array 2600 may be linear (as shown) or curvilinear.

The orientation of on-chip fiber optical sensor array 2600 can be such that acoustic waves are incident on distal reflecting surface 2603. Alternatively, the on-chip fiber optical sensor array 2600 can be oriented such that the acoustic waves are incident along the length of the distal portion of the optical waveguides 2601, including the Bragg gratings 2612. In such an arrangement, the Bragg gratings may be acoustic sensitive Bragg gratings such as disclosed in pending U.S. Application 63/522,793, titled Optical Fiber with Acoustically Sensitive Fiber Bragg Gratings, filed Jun. 23, 2023.

Figures 28A, 28B:
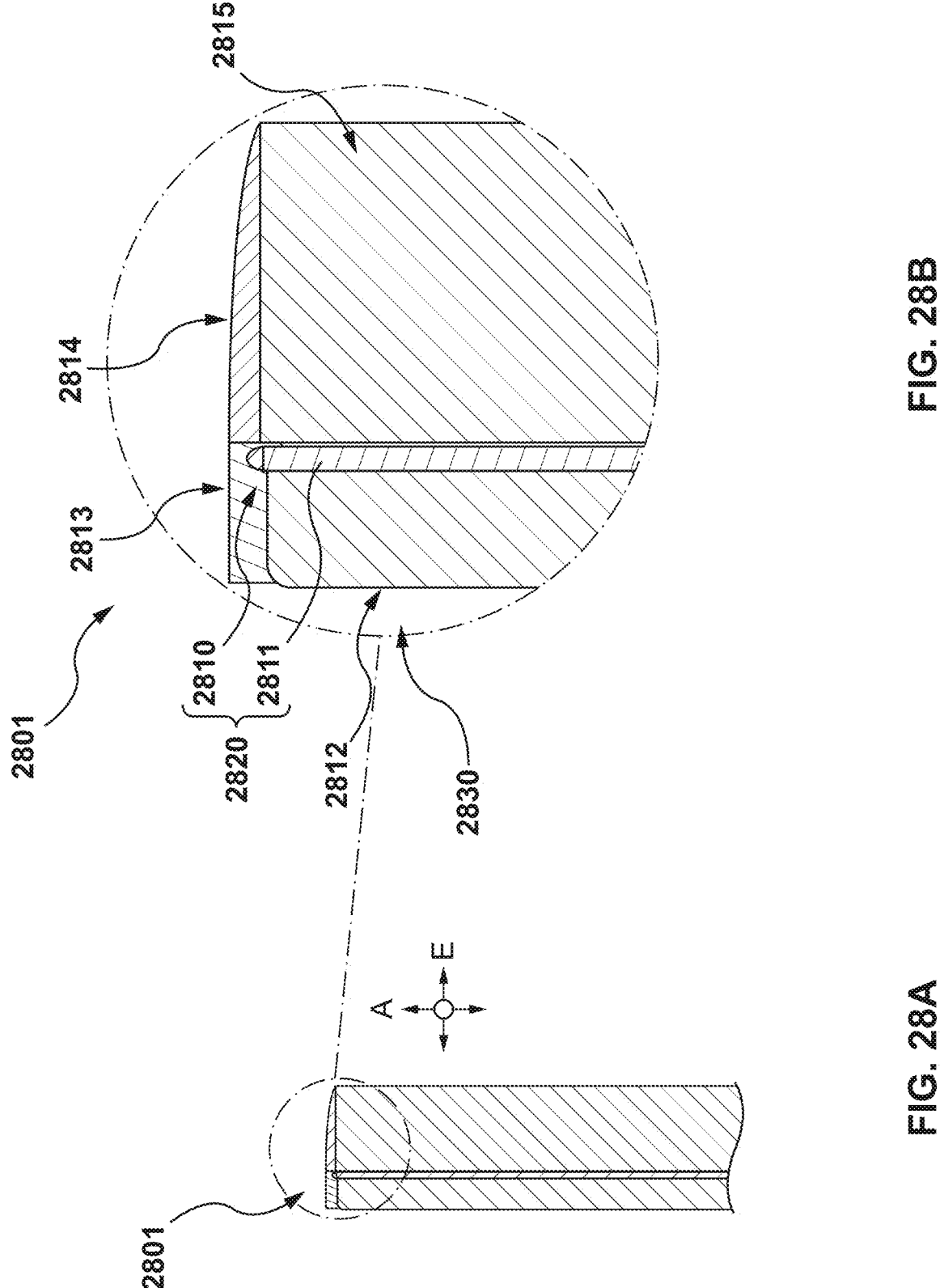
FIGS. 28A and 28B illustrate a structure of a mixed array probe head module according to embodiments herein.

FIGS. 28A and 28B illustrate a structure of a mixed array probe head module according to embodiments herein. FIG. 28A illustrates a cross-sectional view of the probe head module 2801 and FIG. 28B provides an enlarged version. As illustrated, the dimension A represents an axial dimension of the probe head module 2801, the general direction of acoustic energy emission and receipt. The dimension E represents an elevation or height dimension of the probe head module 2801. A dimension L, perpendicular to the page, represents a lateral dimension of the probe head module 2801. Generally, the probe head module 2801 extends further in the lateral dimension L than in the elevation dimension E. The mixed array probe head module 2801 includes a fiber optic sensor array 2830 that includes a plurality of fiber optical sensors 2820 having fiber end sensors 2810 and optical waveguides 2811 mounted to a substrate 2812. The plurality of fiber optical sensors 2820 may be mounted to the substrate in a manner similar to that illustrated in FIG. 25E or FIG. 27A or FIG. 27B or any other suitable manner that secures the fibers to form an array with the desired pitch and geometry. The fiber optical sensor array 2830 may be configured in any suitable way consistent with embodiments hereof and the structure illustrated in these figures may be modified to accommodate the different array shapes disclosed, e.g., in FIGS. 25A-25D. The fiber optical sensors 2820 may be any type of fiber optical sensors 2820 having fiber end sensors discussed herein. The fiber optical sensors 2820 are mounted to a substrate 2812, which may include, for example, the substrate illustrated and described with respect to FIG. 25E or FIG. 27A or FIG. 27B. The fiber optical sensors 2820 are arranged such that the fiber end sensors 2810 are directed in an axial dimension. The fiber optical sensors 2820 may be disposed behind or within interface layer 2813 which may further include an acoustic matching layer and/or an acoustic lens. Interface layer 2813 contacts the surface of the area to be imaged and is made from a biocompatible material with minimal acoustic impedance that also serves as a moisture barrier and electrical insulator. The interface layer 2813 may further include an acoustic matching layer selected for acoustic impedance matching with a target environment, to reduce acoustic reflections at the interface between the interface layer 2813 and the target environment. In embodiments, the interface layer 2813 may further be configured to include an acoustic lens to assist in focusing/steering received acoustic signals to the fiber end sensors 2810. Lastly, interface layer 2813 may include a couplant made of a material with low attenuation and impedance matching such as a flexible or rigid elastomer. The interface layer 2813 may be a single or multiple piece component attached via adhesive and/or may be molded in place to the fiber optical sensor array 2830. The interface layer 2813 may be configured such that there is no air gap between the interface layer 2813 and the portion of the fiber end sensors 2810 that will sense the signals, e.g., such that the interface layer 2813 and the fiber end sensors 2810 are in contact with one another. In embodiments, the interface layer 2813 may be disposed within or as part of a transducer housing as an exterior layer of the transducer device between the fiber optical sensor array 2830 and a surrounding environment. Further, the interface layer 2813 provides protection for the optical sensors 2820.

The mixed array probe head module 2801 may further include an AEG array 2815 mounted to a suitable substrate separate from substrate 2812, consistent with disclosure hereof and an interface layer 2814. In further embodiments, the AEG array 2815 and the fiber optical sensors 2820 may be mounted to a single substrate. The interface layer 2814, like interface layer 2813 may include an acoustic matching layer, an acoustic couplant and/or an acoustic lens depending upon the desired performance of and the materials comprising the AEG array. An acoustic impedance matching layer reduces acoustic reflections at the interface between the array and the imaging target environment. In embodiments, the interface layer 2814 may further include and/or be configured as an acoustic lens to assist in focusing/ steering the acoustic signals emitted and received by the AEG array. The interface layer 2814 may be integrated with or may be separate from the interface layer 2813. In embodiments, the interface layers may be a single integrated component of multiple different materials or may be a single integrated component of a single material. In embodiments, the interface layer 2814 may be disposed within or as part of a transducer housing as an exterior layer of the transducer device between the AEG array 2815 and a surrounding environment.

Figures 29A, 29B:
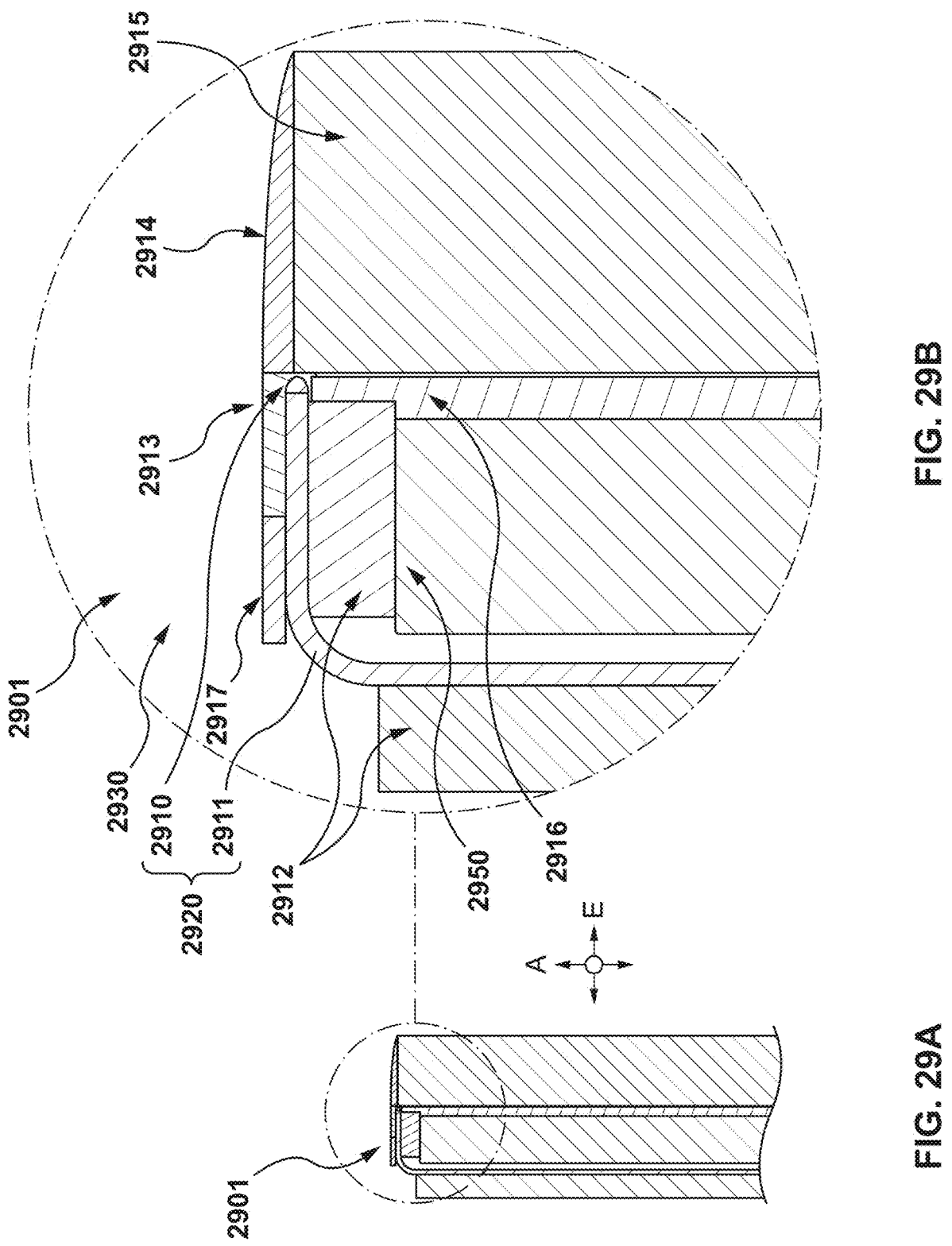
FIGS. 29A and 29B illustrate a structure of a mixed array probe head module according to embodiments herein.

FIGS. 29A and 29B illustrate a structure of a mixed array probe head module according to embodiments herein. FIG. 29A illustrates a cross-sectional view of the probe head module 2901 and FIG. 29B provides an enlarged version. As illustrated, the dimension A represents an axial dimension of the probe head module 2901, the general direction of acoustic energy emission and receipt. The dimension E represents an elevation or height dimension of the probe head module 2901. A dimension L, perpendicular to the page, represents a lateral dimension of the probe head module 2901. Generally, the probe head module 2901 extends further in the lateral dimension L than in the elevation dimension E. The mixed array probe head module 2901 includes a fiber optic sensor array 2930 that includes a plurality of fiber optical sensors 2920 having fiber end sensors 2910 and optical waveguides 2911 mounted to a substrate 2912. The fiber optical sensors 2920 may be any type of fiber optical sensors 2920 having fiber end sensors discussed herein. The fiber optical sensors 2920 are mounted to a substrate 2912, which may include two portions to accommodate the fiber optical sensors 2920. The fiber optical sensors 2920 are arranged such that the fiber end sensors 2910 are oriented in an elevation dimension. Accordingly, the substrate 2912 is configured to maintain a bend of the optical waveguides 2911 to reorient the dimension of distal portions of the fiber optical sensors 2920 from an axial dimension (necessary for extending through the probe head) to the elevation dimension. The fiber end sensors 2910 may include fiber end sensors described herein that are oriented in a side-looking fashion compared to the optical waveguides 2911 or in a forward-looking fashion and taking advantage of the broad field of view afforded by fiber end sensors described herein. The fiber optical sensors 2920 may be disposed behind or within an interface layer 2913 and secured by optical fixture 2917. The optical fixture 2917 is configured to secure the fiber optical sensors 2920 to the substrate 2912 and, in some embodiments, may be integral with the interface layer 2913. Interface layer 2913 contacts the surface of the area to be imaged and is made from a biocompatible material with minimal acoustic impedance that also serves as a moisture barrier and electrical insulator. The interface layer 2913 may further include an acoustic matching layer, and/or an acoustic lens. The interface layer 2913 is comprised of one or more materials selected for acoustic impedance matching with a target environment, to reduce acoustic reflections at the interface between the interface layer 2913 and the target. The fiber optic sensor array 2930 may be mounted to or may include a mechanical sublayer 2950 to facilitate integration within the probe head. The fiber optic sensor array may further include an optical backing block 2916, configured to provide acoustic isolation and damping, e.g., to prevent internal acoustic reflections within the probe from rebounding back to the fiber end sensors 2910. Further, the interface layer 2913 provides protection for the optical sensors 2920. The mixed array probe head module 2901 further includes an AEG array 2915, consistent with disclosure hereof and an interface layer 2914. Interface layer 2914 contacts the surface of the area to be imaged and is made from a biocompatible material with minimal acoustic impedance that also serves as a moisture barrier and electrical insulator. Interface layer 2914 may include an acoustic matching later, and/or an acoustic lens. In embodiments, the interface layer 2913 and the interface layer 2914 may be disposed within or as part of a transducer housing as an exterior layer of the transducer device between the fiber optical sensor array 2930 or the AEG array 2915, respectively, and a surrounding environment The interface layers 2913 and 2914 may each include some or all of the features described with respect to the interface layers 2813 and 2814.

Figures 30A, 30B:
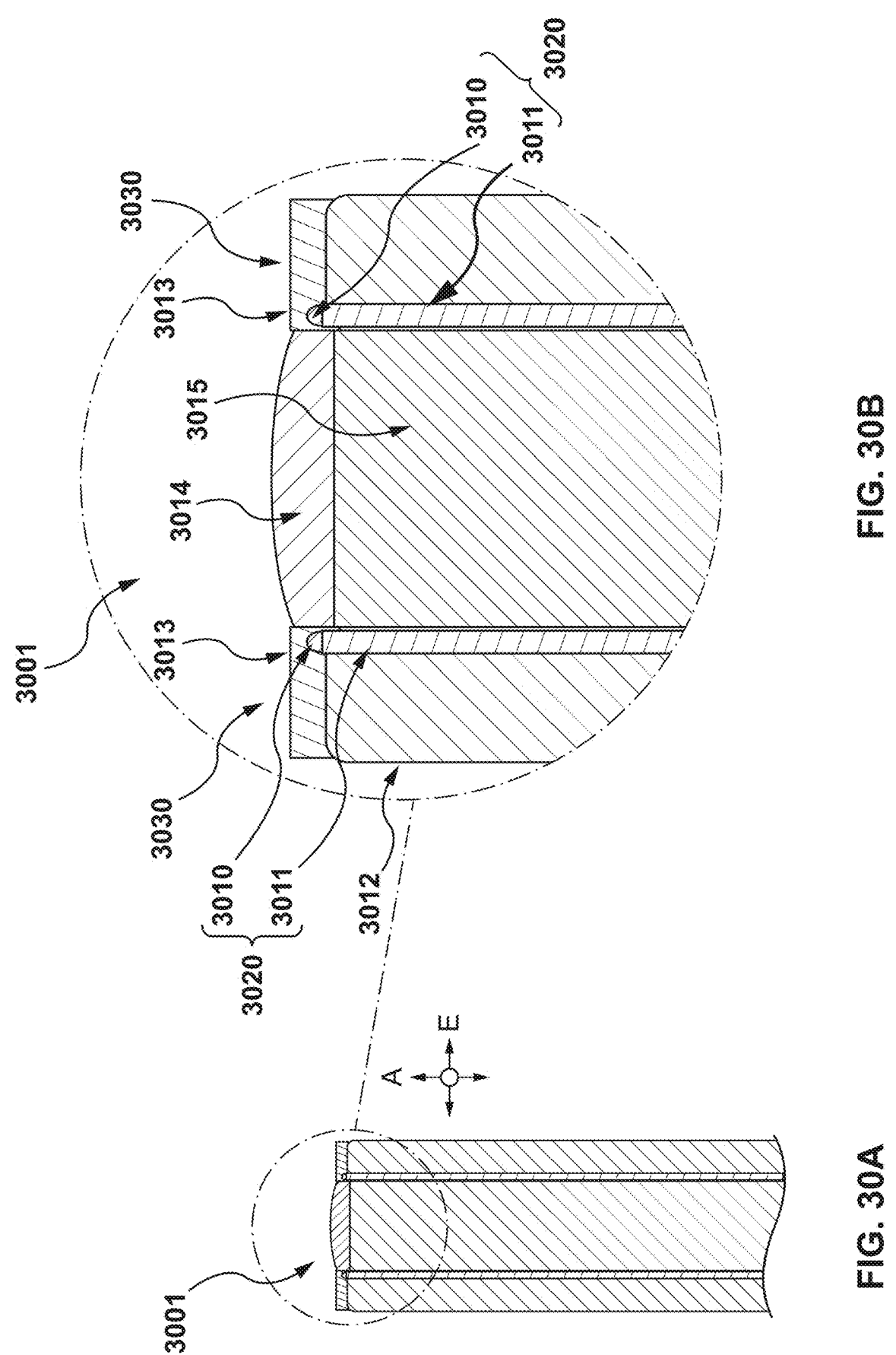
FIGS. 30A and 30B illustrate embodiments of a fiber sensor array transducer according to embodiments herein.

FIGS. 30A and 30B illustrate a structure of a mixed array probe head module according to embodiments herein. FIG. 30A illustrates a cross-sectional view of the probe head module 3001 and FIG. 30B provides an enlarged version. As illustrated, the dimension A represents an axial dimension of the probe head module 3001, the general direction of acoustic energy emission and receipt. The dimension E represents an elevation or height dimension of the probe head module 3001. A dimension L, perpendicular to the page, represents a lateral dimension of the probe head module 3001. Generally, the probe head module 3001 extends further in the lateral dimension L than in the elevation dimension E. The mixed array probe head module 3001 includes a pair of fiber optic sensor arrays 3030 that each include a plurality of fiber optical sensors 3020 having fiber end sensors 3010 and optical waveguides 3011 mounted to a substrate 3012. The fiber optical sensor arrays 3030 are configured e.g., according to the structure shown in FIG. 25C. In embodiments, the same structures may be rearranged to accommodate the structure shown in FIG. 25D. In embodiments, the concepts illustrated in the probe head module 3001 may be applied to any of the probe head modules discussed herein to provide for a probe head module having a pair of fiber optical sensor arrays. The fiber optical sensors 3020 may be any type of fiber optical sensors 3020 having fiber end sensors discussed herein. The fiber optical sensors 3020 are mounted to a substrate 3012, which may include, for example, the substrate illustrated and described with respect to FIG. 25E. The fiber optical sensors 3020 are arranged such that the fiber end sensors 3010 are directed in an axial dimension (although, as noted, elevation dimension orientations may also be accommodated). The fiber optical sensors 3020 may be disposed behind or within interface layers 3013. Interface layers 3013 contact the surface of the area to be imaged and is made from a biocompatible material with minimal acoustic impedance that also serves as a moisture barrier and electrical insulator. The interface layers 3013 may further include an acoustic matching layer, and/or an acoustic lens. The interface layers 3013 may be selected for acoustic impedance matching with a target environment, to reduce acoustic reflections at the interface between the interface layers 3013 and the target. Further, the interface layers 3013 provides protection for the optical sensors 3020. The mixed array probe head module 3001 further includes an AEG array 3015, consistent with disclosure hereof and may include an interface layer 3014. Interface layer 3014 contacts the surface of the area to be imaged and is made from a biocompatible material with minimal acoustic impedance that also serves as a moisture barrier and electrical insulator. The interface layer 3014 may further include an acoustic matching layer, and/or an acoustic lens. In embodiments, the interface layers 3013 and the interface layer 3014 may be disposed within or as part of a transducer housing as an exterior layer of the transducer device between the fiber optical sensor array 3030 or the AEG array 3015, respectively, and a surrounding environment The interface layers 3013 and 3014 may each include some or all of the features described with respect to the interface layers 2813 and 2814. The AEG array 3015 may be arranged between the two optical sensor arrays 3030.

Figure 31:
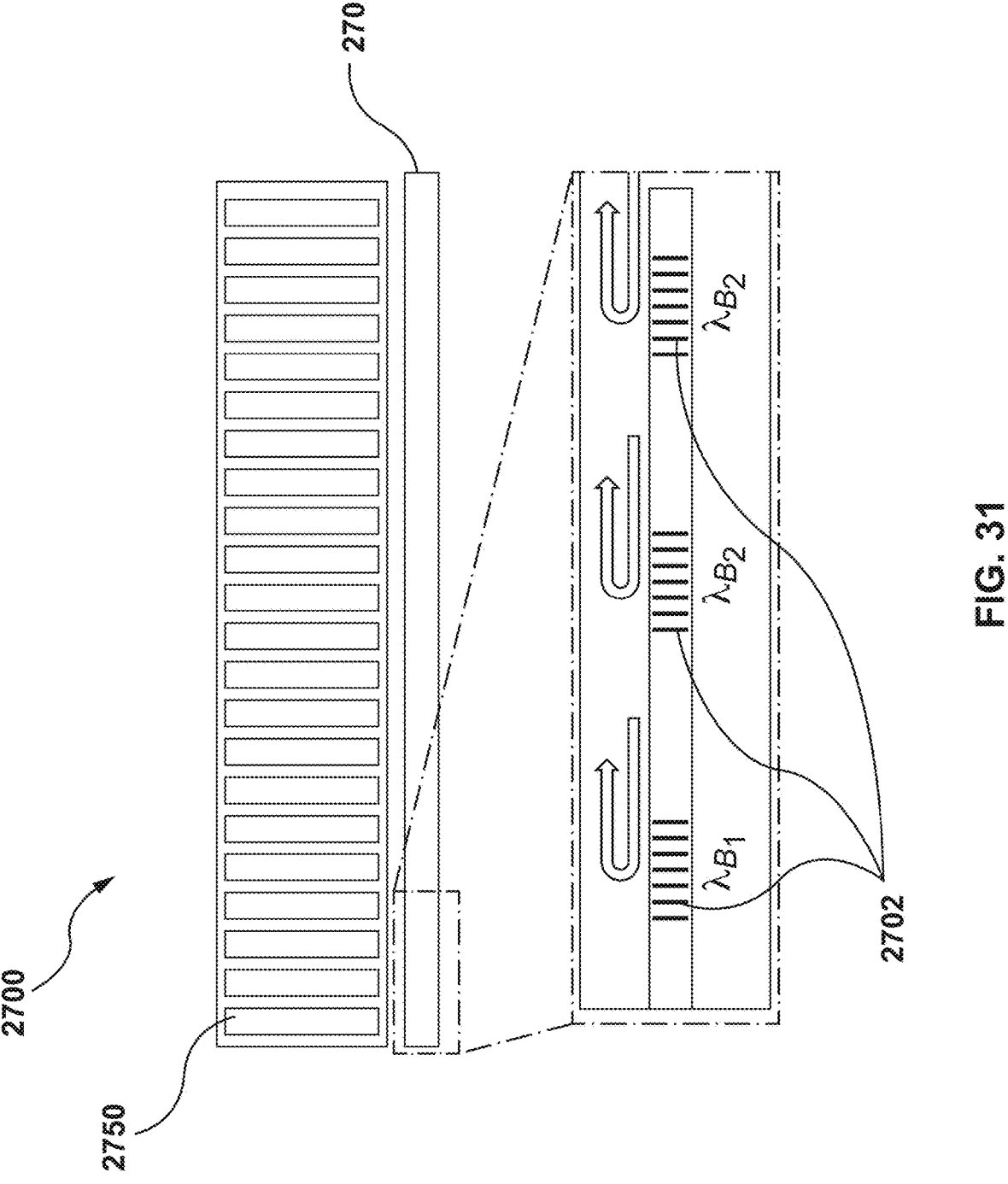
FIG. 31 illustrates a polarization based fiber sensor array transducer according to embodiments herein.
Figure 32:
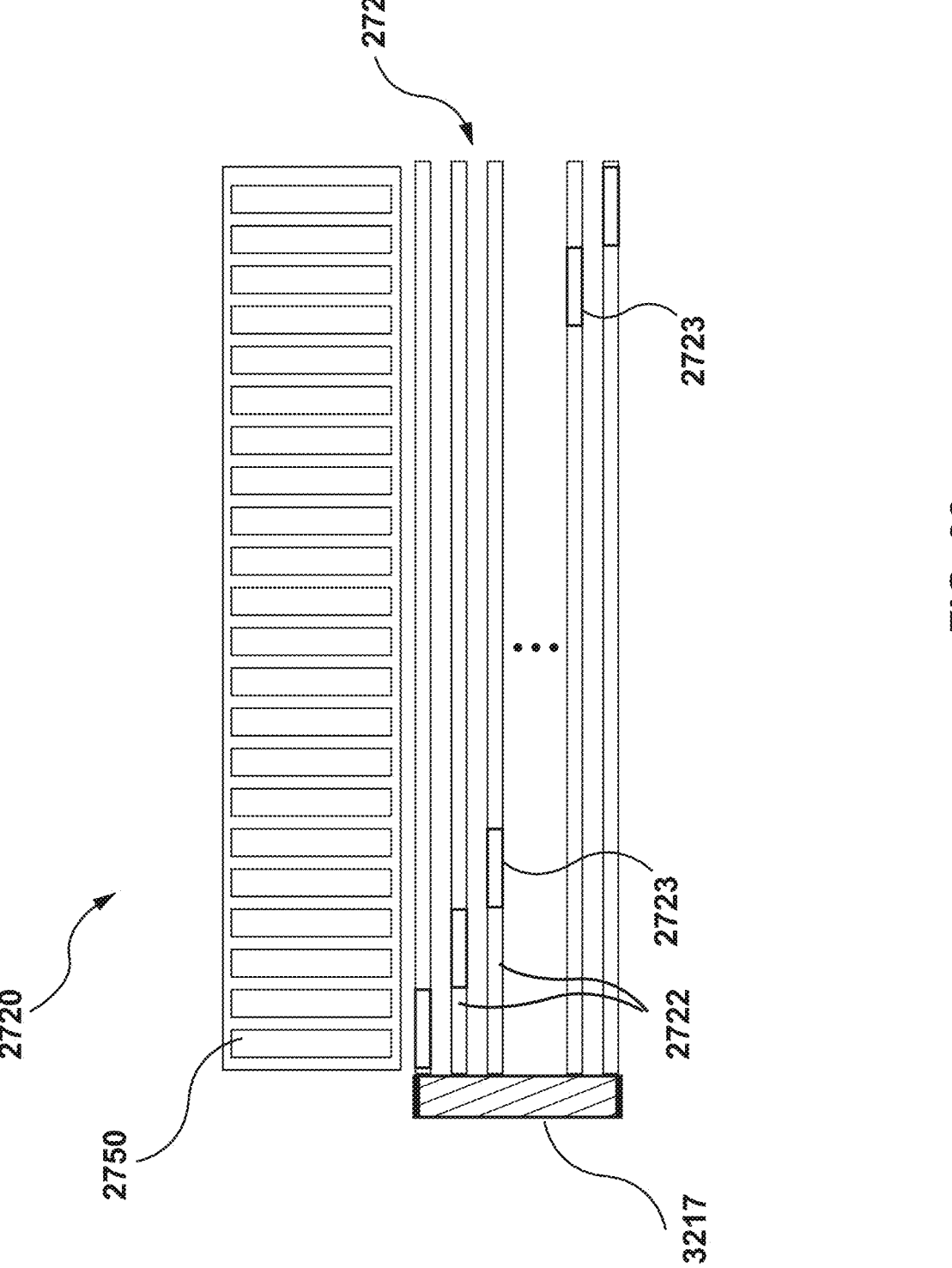
FIG. 32 illustrates a polarization based fiber sensor array transducer according to embodiments herein.

FIGS. 31 and 32 illustrate embodiments of polarization based fiber sensor array transducers consistent with the disclosure. FIG. 31 illustrates a polarization based fiber sensor array transducer 2700. The polarization based fiber sensor array transducer 2700 may include a polarization based fiber sensor array 2701 and a transmission array 2750, for example, an array of AEG elements, for sending and receiving acoustic signals. The polarization based fiber sensor array 2701 may be included within a single optical fiber that is arranged transversely to the transmission array 2750 such that the polarization based fiber sensor array 2701 is substantially perpendicular to the direction that the acoustic signals are transmitted. The polarization based fiber sensor array 2701 may include a plurality of Bragg reflectors 2702, each configured to reflect light of a different wavelength. As discussed above, polarization based sensors may be sensitive to acoustic signals received from a direction substantially perpendicular to the polarization based fiber sensor array transducer 2700. Because each Bragg reflector 2702 reflects a different wavelength of light, when the polarization based fiber sensor array 2701 receives light at multiple wavelengths, there is a different mix of wavelengths present within the polarization based fiber sensor array 2701 in advance of each Bragg reflector 2702. Accordingly, acoustic signals incident upon the polarization based fiber sensor array 2701 at different points along its length may be measured based on changes in the different wavelengths of reflected light. A transmission array 2750 may emit acoustic signals and the polarization based fiber sensor array 2701 may receive reflections from these. The reflected acoustic signals may be incident upon the polarization based fiber sensor array 2701 at different locations along its length, and therefore may be detected according to the principles of the polarization based sensors described herein. In embodiments, the polarization based fiber sensor array 2701, which may include a single fiber, may be arranged directly in line with (in an axial direction) the transmission array 2750. In such embodiments, appropriate acoustic damping and matching materials may be provided between either the transmission array 2750 and the fiber sensor array 2701 or the fiber sensor array 2701 and an acoustic lens to minimize noise and/or acoustic reflections. The design of FIG. 31 provides a reduced footprint, as only a single fiber sensor array 2701 is required (although additional fiber sensor arrays 2701 may also be employed. The design of FIG. 31 may be employed with a dedicated back-end system configured to demultiplex the signals received from the sensor arrays 2701.

FIG. 32 illustrates a polarization based fiber sensor array transducer 2720. The polarization based fiber sensor array transducer 2720 may include a polarization based fiber sensor array 2721 and a transmission array 2750, for example, an array of AEG elements. The polarization based fiber sensor array 2721 includes a plurality of individual fiber sensors 2722 configured for polarization based acoustic signal detection according to methods described herein. The polarization based fiber sensor array 2721 may be arranged transversely to the transmission array 2750 such that the polarization based fiber sensor array 2721 is substantially perpendicular to the direction that the acoustic signals are transmitted. The transverse orientation may be facilitated by an optical fixture 3217 configured to facilitate or provide reorientation of the fiber sensors 2722 from an axial orientation (to extend through the probe) to a lateral orientation. The optical fixture 3217 may be provided on either side of the polarization based fiber sensor array 2721 and, in embodiments, may include two optical fixtures 3217, one on each side of the polarization based fiber sensor array 2721. In embodiments, the individual fiber sensors 2722 may be arranged such that they are in contact with one another with no gaps or another material therebetween. In embodiments, the individual fiber sensors 2722 may be arranged such that they are not in contact with one another and gaps between the individual fiber sensors 2722 may be filled with or by an appropriate material that may have a similar or matching acoustic impedance. In embodiments, the polarization based fiber sensor array 2721 may be encapsulated or covered by an appropriate material having a similar or matching acoustic impedance. Each of the plurality of individual fiber sensors 2722 includes an exposure window 2723. The exposure windows 2723 are arranged such that different portions along the length of the polarization based fiber sensor array 2721 have exposure windows 2723 capable of receiving and detecting acoustic signals. In embodiments, the exposure windows 2723 may be arranged such that all portions along the length of the polarization based fiber sensor array 2721 are associated with at least one exposure window 2723. In embodiments, the exposure windows 2723 may overlap. In other embodiments, the exposure windows 2723 do not overlap but are arranged such that there are no gaps in exposure along the length of the polarization based fiber sensor array 2721. In further embodiments, gaps in exposure along the length of the polarization based fiber sensor array 2721 may exist between exposure windows. Accordingly, acoustic signals incident upon the polarization based fiber sensor array 2721 at different points along its length (e.g., at different exposure windows 2723) may be measured based which of the individual fiber sensors 2722 receives and detects the acoustic signal. A transmission array 2750 may emit acoustic signals and the polarization based fiber sensor array 2721 may receive reflections from these. The reflected acoustic signals may be incident upon the polarization based fiber sensor array 2721 at different locations along its length, and therefore may be detected according to the principles of the polarization based sensors described herein. The fiber sensor array transducer 2720 may be advantageous because, due to the multiple fibers involved in the fiber sensor array 2721, demultiplexing is not required. Because the individual fiber sensors 2722 are significantly smaller (less than $\frac{1}{10}$, less than $\frac{1}{20}$) than AEG elements, footprint reduction via use of fewer fibers may not be necessary.

Figures 33A, 33B, 33C:
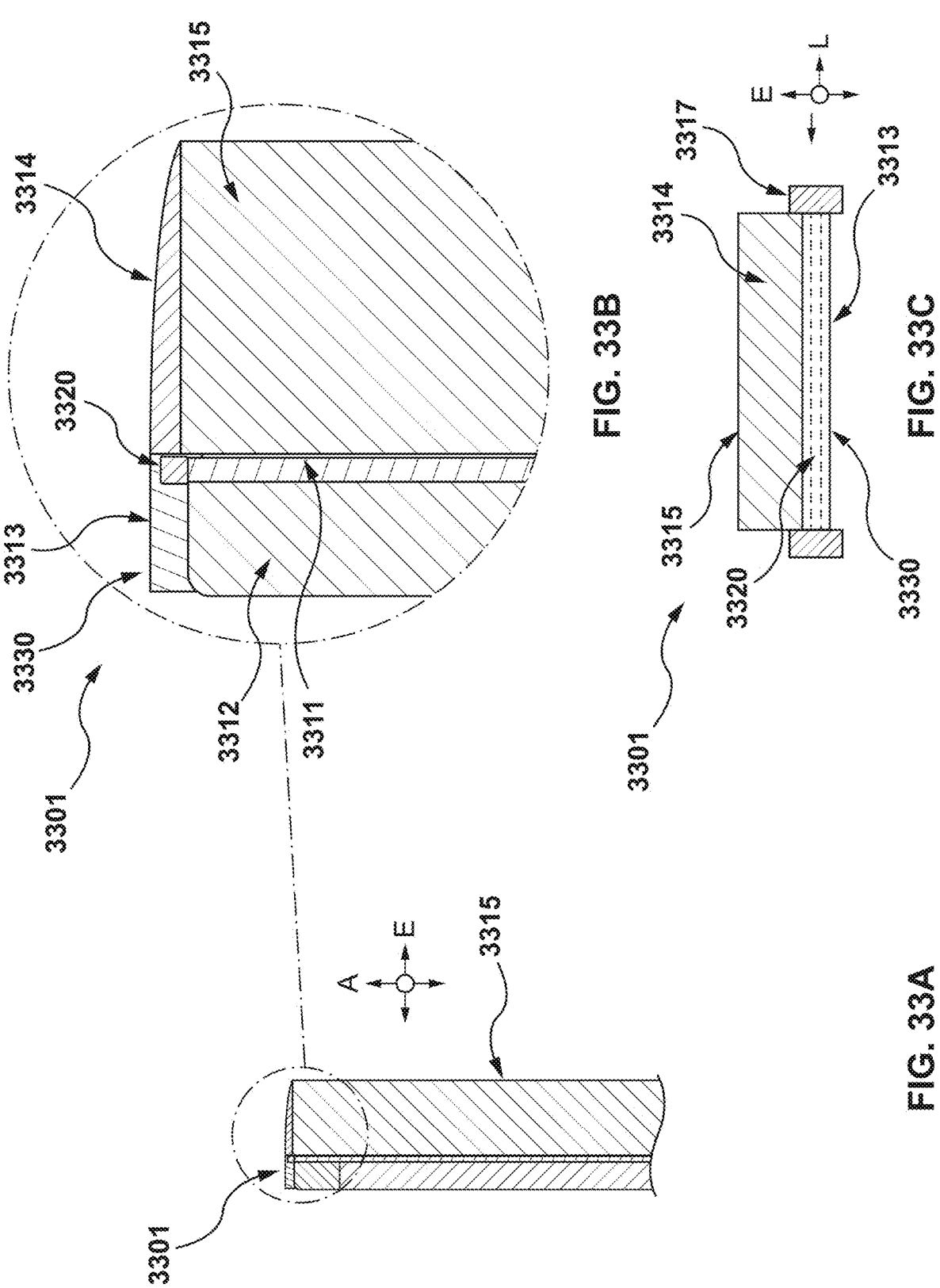
FIGS. 33A, 33B, and 33C illustrate a structure of a mixed array probe head module according to embodiments herein.

FIGS. 33A, 33B, and 33C illustrate a structure of a mixed array probe head module according to embodiments herein. FIGS. 33A, 33B, and 33C illustrate a probe head module accommodating a polarization based fiber sensor array transducer 2700 consistent with that of FIG. 31. FIG. 33A illustrates a cross-sectional view of the probe head module 3301 and FIG. 30B provides an enlarged version. FIG. 33C illustrates the probe head module as viewed in an axial dimension. As illustrated, the dimension A represents an axial dimension of the probe head module 3301, the general direction of acoustic energy emission and receipt. The dimension E represents an elevation or height dimension of the probe head module 3301. A dimension L, perpendicular to the page, represents a lateral dimension of the probe head module 3301. Generally, the probe head module 3301 extends further in the lateral dimension L than in the elevation dimension E. The mixed array probe head module 3301 includes a polarization based fiber optic sensor array 3330 that includes a fiber optical sensor 3320 provided with Bragg gratings along its length in the manner of the polarization based fiber sensor array transducer 2700 at the end of an optical waveguide 3311. The fiber optical sensor 3320 is mounted to a substrate 3312, which may include, for example, a substrate similar to that illustrated and described with respect to FIG. 25E. The fiber optical sensor 3320 is arranged such that it is directed in a lateral dimension. This orientation is facilitated by an optical fixture 3317 configured to facilitate or provide reorientation of the fiber optical sensor 3320 from an axial orientation (to extend through the probe) to a lateral orientation. The optical fixture 3317 may be provided on either side of the mixed array probe head module 3301 and, in embodiments, may include two optical fixtures 3317, one on each side of the mixed array probe head module 3301. In embodiments, the substrate 3312 may include materials that promote acoustic damping and minimize acoustic reflection, to reduce or prevent acoustic echoes from occurring within the probe head itself. The fiber optical sensor 3020 may be disposed behind or within an interface layer 3313. Interface layer 3013 contacts the surface of the area to be imaged and is made from a biocompatible material with minimal acoustic impedance that also serves as a moisture barrier and electrical insulator. The interface layer 3013 may further include an acoustic matching layer and/or an acoustic lens. Further, the interface layer 3313 provides protection for the optical sensors 3320. The mixed array probe head module 3301 further includes an AEG array 3315, consistent with disclosure hereof and an interface layer 3314. The interface layer 3314 may include suitable components and materials. In embodiments, the design of the probe head module 3301 may be modified to accommodate a plurality of polarization based fiber sensors, according to the design of the polarization based fiber sensor array transducer 2700. In embodiments, the interface layer 3313 and the interface layer 3314 may be disposed within or as part of a transducer housing as an exterior layer of the transducer device between the fiber optical sensor array 3330 or the AEG array 3315, respectively, and a surrounding environment The interface layers 3313 and 3314 may each include some or all of the features described with respect to the interface layers 2813 and 2814.

Figure 34:
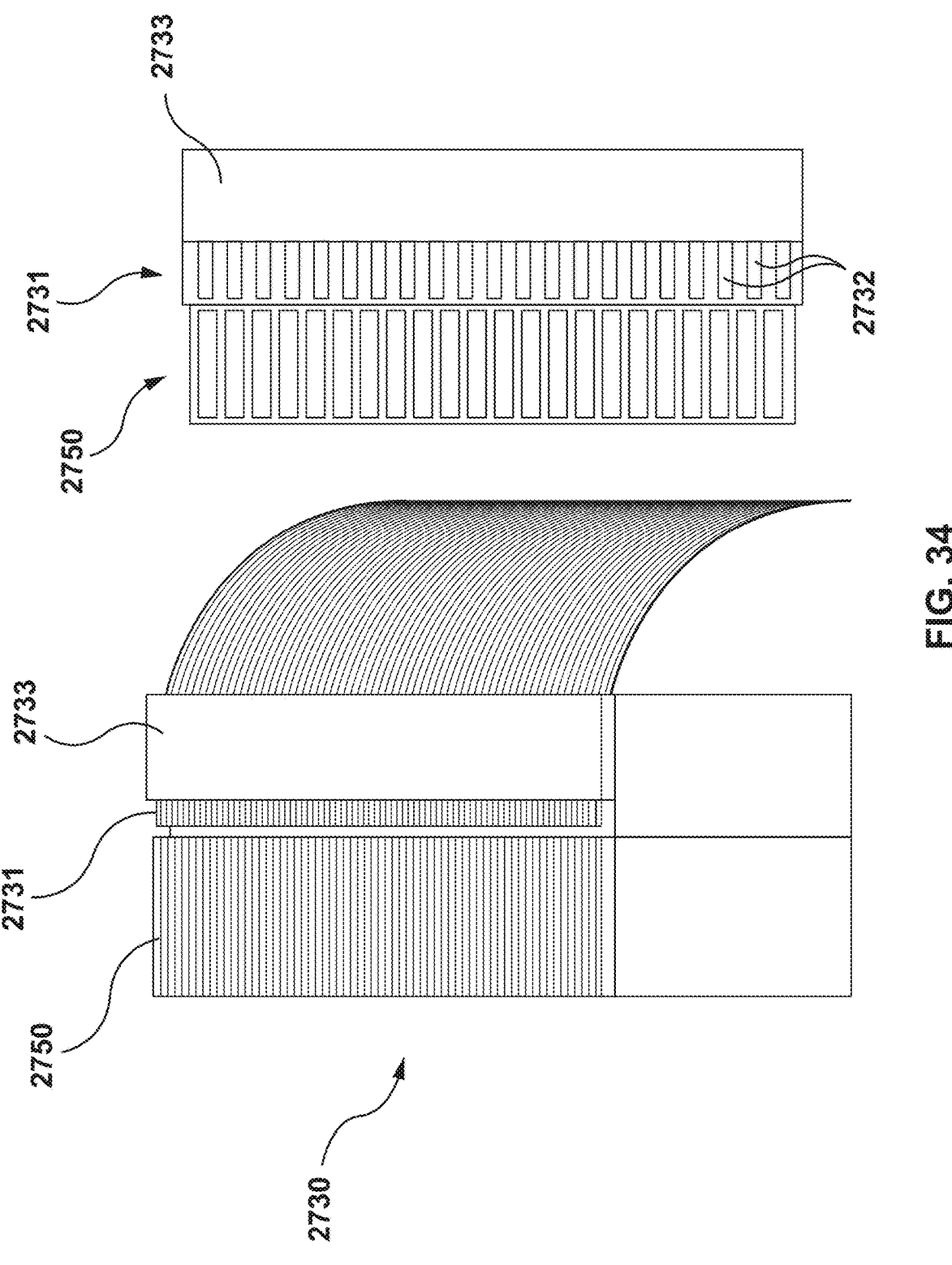
FIG. 34 illustrates a polarization based fiber sensor array transducer according to embodiments herein.

FIG. 34 illustrates a polarization based fiber sensor array transducer 2730. The polarization based fiber sensor array transducer 2730 may include a polarization based fiber sensor array 2731 and a transmission array 2750, for example, an array of AEG elements. The polarization based fiber sensor array 2731 includes a plurality of individual fiber sensors 2732 configured for polarization based acoustic signal detection according to methods described herein. The polarization based fiber sensor array 2731 may be arranged substantially parallel to the transmission (AEG) array 2750 such that the plurality of individual fiber sensors 2732 are substantially parallel (e.g., with 10 degrees of parallel) to the direction that the acoustic signals are transmitted. Each of the plurality of individual fiber sensors 2732 may be exposed to receive acoustic signals at an end thereof. An acoustic shield 2733 may be positioned across the polarization based fiber sensor array 2731 to limit the acoustic signals incident upon the polarization based fiber sensor array 2731 away from the exposed end portions (which may also be referred to as acoustic windows). Accordingly, acoustic signals incident upon the polarization based fiber sensor array 2731 at different points along its length (e.g., on different individual fiber sensors 2732) may be measured based which of the individual fiber sensors 2732 receives and detects the acoustic signal. A transmission array 2750 may emit acoustic signals and the polarization based fiber sensor array 2731 may receive reflections from these. The reflected acoustic signals may be incident upon the polarization based fiber sensor array 2731 at different locations along its length, and therefore may be detected according to the principles of the polarization based sensors described herein.

Figures 35A, 35B, 35C:
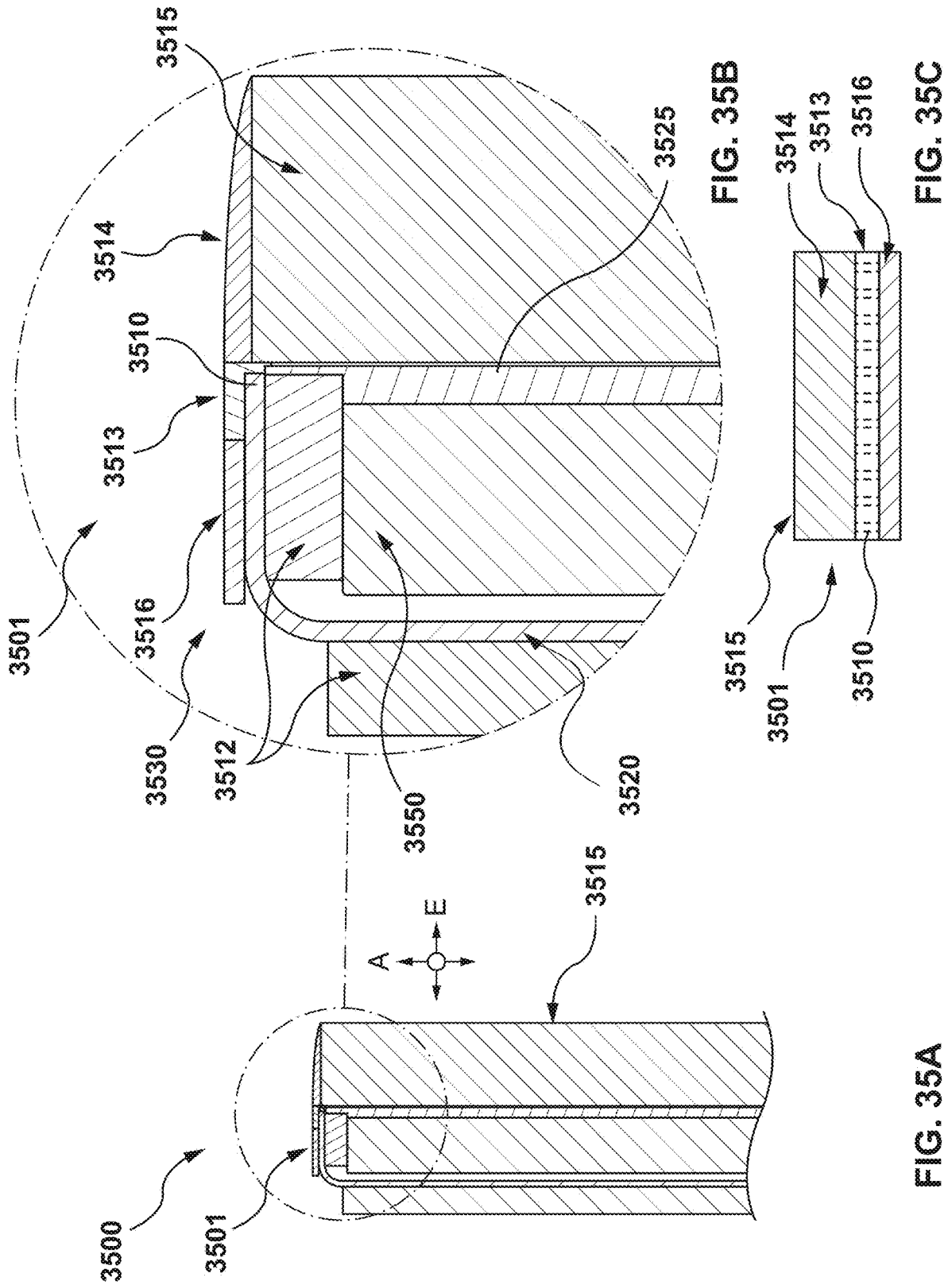
FIGS. 35A, 35B, and 35C illustrate a structure of a mixed array probe head module according to embodiments herein.

FIGS. 35A, 35B, and 35C illustrate a structure of a mixed array probe head module according to embodiments herein. FIGS. 35A, 35B, and 35C illustrate a probe head module accommodating a polarization based fiber sensor array transducer 3500 consistent with that of FIG. 34. FIG. 35A illustrates a cross-sectional view of the probe head module 3501 and FIG. 35B provides an enlarged version. FIG. 35C illustrates the probe head module as viewed in an axial dimension. As illustrated, the dimension A represents an axial dimension of the probe head module 3501, the general direction of acoustic energy emission and receipt. The dimension E represents an elevation or height dimension of the probe head module 3501. A dimension L, perpendicular to the page, represents a lateral dimension of the probe head module 3501. Generally, the probe head module 3501 extends further in the lateral dimension L than in the elevation dimension E. The mixed array probe head module 3501 includes a polarization based fiber optic sensor array 3530 that includes a plurality of fiber optical sensors 3520 in the manner of the polarization based fiber sensor array transducer 2730. The fiber optical sensors 3520 are mounted to a substrate 3512, which may include, for example, a substrate similar to that illustrated and described with respect to FIG. 25E. The fiber optical sensors 3520 are arranged such that the they are directed in an elevation dimension with exposed end portions 3510 configured to receive reflected acoustic signals. The exposed end portions 3510 are portions of the fiber optical sensors 3520 with exposure or acoustic windows (e.g., portions where cladding or encapsulation is removed or reduced, as described with respect to FIGS. 6D and 6DD to permit acoustic signals to pass into the fiber optical sensors 3520). This orientation is facilitated by an optical fixture 3516 configured to facilitate or provide reorientation of the fiber optical sensor 3520 from an axial orientation (to extend through the probe) to an elevation orientation. The optical fixture 3516 may be configured to be acoustically reflective to prevent acoustic signals from reaching the fiber optical sensors 3520 outside of the end portions 3510. In embodiments, the substrate 3512 may include materials that promote acoustic damping and minimize acoustic reflection, to reduce or prevent acoustic echoes from occurring within the probe head itself. The fiber optical sensor 3520 may be disposed behind or within an interface layer 3513. The interface layer 3513 may include all of the features of previously discussed interface layers, e.g., interface layer 2813. Interface layer 3513 contacts the surface of the area to be imaged and is made from a biocompatible material with minimal acoustic impedance that also serves as a moisture barrier and electrical insulator. The interface layer 3513 may further include an acoustic matching layer and/or an acoustic lens. In further embodiments interface layer 3513 with an acoustic lens has different, for example, increased, beam steering properties as compared to other interface layers described herein to address the larger signal reception area of the exposed end portions 3510. The interface layer 3513 may be selected for acoustic impedance matching with a target environment, to reduce acoustic reflections at the interface between the interface layer 3513 and the target. Further, the interface layer 3513 provides protection for the exposed end portions 3510. The fiber optic sensor array 3530 may further include an optical backing block 3525, configured to provide acoustic isolation and damping, e.g., to prevent internal acoustic reflections within the probe from rebounding back to the optical fiber sensor 3520. The fiber optic sensor array 3530 may be mounted to or may include a mechanical sublayer 3550 to facilitate integration within the probe head. In embodiments, the mechanical sublayer 3550 and/or the substrate 3512 may also include acoustic isolation and/or damping characteristics. The mixed array probe head module 3501 further includes an AEG array 3515, consistent with disclosure hereof and interface layer 3514, which may include a matching layer and/or an acoustic lens. In embodiments, the interface layer 3513 and the interface layer 3514 may be disposed within or as part of a transducer housing as an exterior layer of the transducer device between the fiber optical sensor array 3530 or the AEG array 3515, respectively, and a surrounding environment The interface layers 3513 and 3514 may each include some or all of the features described with respect to the interface layers 2813 and 2814.

Figure 36:
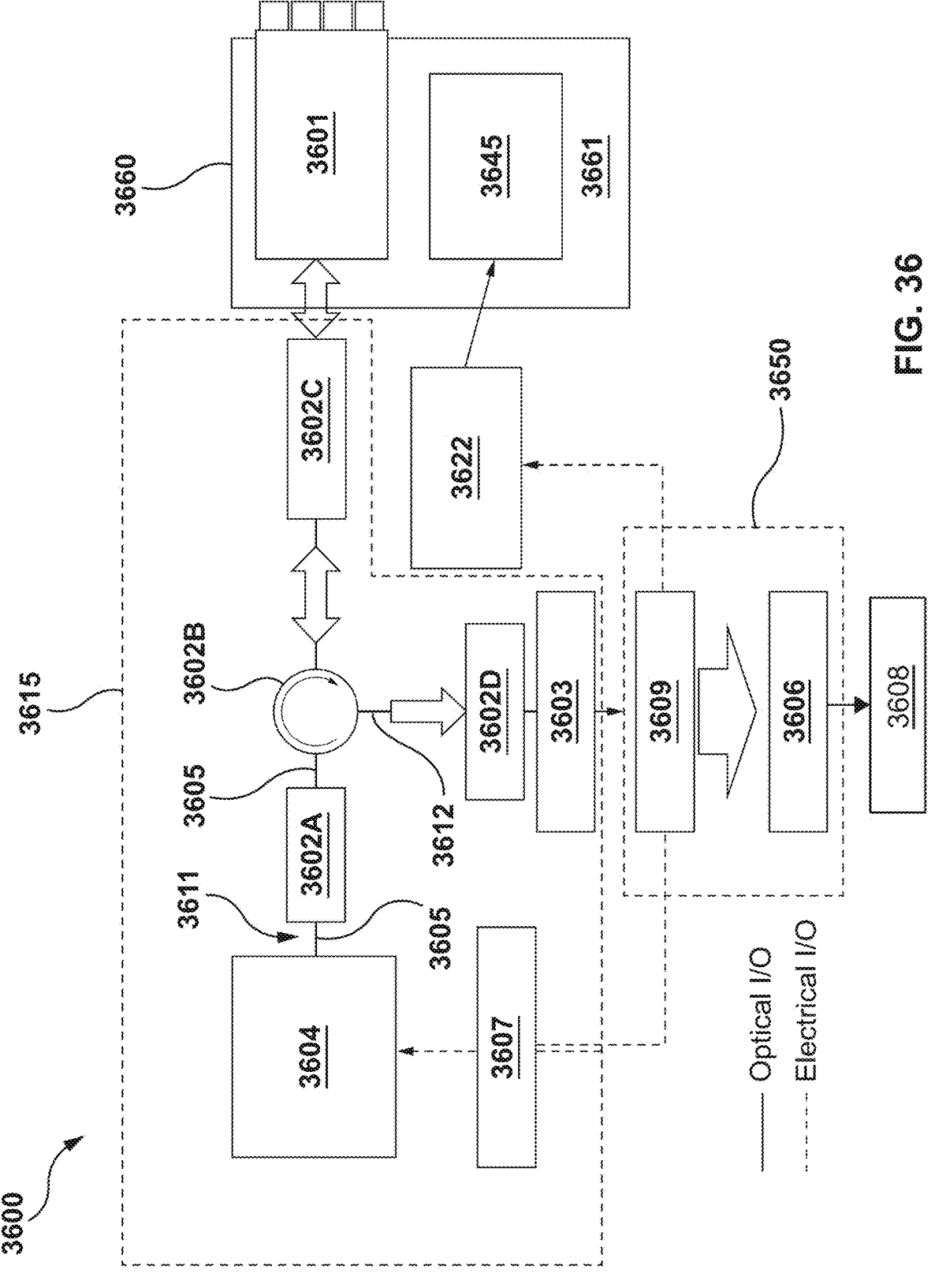
FIG. 36 illustrates an optical acoustic sensor system for use with a fiber optical sensor according to embodiments herein.

FIG. 36 illustrates an optical acoustic sensor system for use with a fiber optical sensor. The optical acoustic sensor system 3600 includes components, devices, hardware, and software to facilitate the use of a mixed sensor array 3661 any of FIGS. 28A-30B. In embodiments, for example as shown in FIG. 36, the optical acoustic sensor system 3600 may include hardware and componentry to facilitate the use of both the acoustic and the optical aspects of a mixed sensor array 3661. The optical acoustic sensor system 3600 may include a processing system 3650, an optical sub-system 3615, and a mixed array transducer probe 3660 that incorporates the mixed sensor array 3661.

The processing system 3650 may include a processing unit 3609 and an image reconstruction unit 3606. Processing unit 3609 may include at least one computer processor, at least one non-transitory computer readable storage medium, and appropriate software instructions. The processing unit 3609 is configured to provide control signals to and receive information signals from the light source control unit 3607, the light receiving device 3603, and the acoustic control unit 3622. The processing unit 3609 may communicate (via control signals and information signals) with the light source control unit 3607, thereby providing control of optical signals provided to the optical acoustic sensor system 3600. The processing unit 3609 may communicate (via control signals and information signals) with the acoustic control unit 3622, thereby providing control and reception of acoustic signals via the AEG array 3645 of the mixed sensor array 3661. The processing unit 3609 is further configured to communicate with the light receiving device 3603 to receive information signals associated with optical signals received by the light receiving device 3603. Thus, processing unit 3609 operates to provide the necessary control signals and receive the acquired information signals in the optical acoustic sensor system 3600.

The processing unit 3609 is further in communication with the image reconstruction unit 3606, which operates to generate images based on the data and/or information acquired by the processing unit 3609. The image reconstruction unit 3606 may generate images based on data related to a medium, such as a human body, captured by the mixed sensor array 3661, which may be incorporated into a mixed sensor array transducer probe 3660. The image reconstruction unit 3606 may be integrated within a system containing the processing unit 3609 and/or may be a separate system including at least one computer processor, at least one non-transitory computer readable storage medium, and appropriate software instructions. The processing unit 3609 may further be configured to receive electrical signals that are representative of and consistent with the sensed or measured physical parameters and to process and interpret the electrical signals to provide data or information related to the physical parameters. The processing system 3650 may provide control signals to an output device 3608 to provide a data output. The output device 3608 may include, for example, a display or a device including a display.

In some embodiments, the output device 3608 may further include additional systems, such as a medical procedure system that is configured to use the data that is output. For example, output device 3608 may include an endoscopy system, a laparoscopic system, a robotic surgical system, neurosurgical system and additionally may include an interoperative ultrasound imaging system.

The optical sub-system 3615 includes a light source control unit 3607, a light source 3604, optical devices 3602A, 3602B, 3602C, and 3602D, and light receiving device 3603. The light source control unit is configured to interface with and control the light source 3604 to control the production of initial optical signals 3611. The light source 3604 may include a plurality or array of operating lasers, each configured to provide an initial optical signal 3611 to an optical fiber sensor of the optical sensor array 3601. The initial optical signals 3611 may be of a selection of frequencies/wavelengths and/or polarizations. Thus, the light source 3604 may include a laser array configured to produce laser light in one or more modes and at one or more frequencies. Additionally, the polarization of the supplied light may be controlled to optimize the detected signal levels according to application requirement. The polarization state of light can be controlled to be linear polarized at certain angles or to be circularly polarized. Linearly polarized light will respond optimally to a certain input ultrasound direction, and circularly polarized light will respond to ultrasound from all directions. The polarization of light can be defined from the laser source output, and the output polarization state can be controlled by an in-line fiber polarizer, a paddle fiber polarization controller, an in-line fiber polarization controller, or other types of polarization controller. The optical devices 3602A, 3602B, and 3602C may be configured to manipulate or influence the initial optical signals 3611 received at the optical sensor array 3601. The optical device 3602A may include, for example, a wavelength division multiplexing (WDM) device configured to multiplex the initial optical signals 3611 provided by the light source 3604 for simultaneous transmission over the optical waveguides 3605 that direct the initial optical signals 3611 to the optical sensor array 3601. The optical device 3602B may be a circulator with first, second and third ports, where the first port is in optical communication with the light source through a wavelength division multiplexing device (WDM) 3602A. While an optical circulator 3602B is discussed, optical components such as optical couplers may be used instead. The initial optical signals 3611 (multiplexed to pass over a single waveguide) may pass through a second optical device 3602B, which may be an optical circulator, for example, and which is configured to direct the initial optical signals 3611 to the optical device 3602C. The optical device 3602C may include a WDM device configured to de-multiplex the initial optical signals 3611 such that each of the multiple fiber optical sensors within the optical sensor array 3601 receives and subsequently outputs its own individual optical signal. Optical device 3602C is in optical communication with the second port of the second optical device 3602B for dividing the initial optical signal 3611 into the multiple optical signals going to the optical sensor array 3601 and combining the returned optical signals from the optical sensor array 3601. These returned optical signals are then directed though a third port of the second optical device 3602B towards optical device 3602D which may include a WDM device configured to again demultiplex the reflected optical signals 3612 for reception at the light receiving device 3603.

The initial optical signal 3611 is received by the fiber optical sensor array 3601 and returned through the one or more optical waveguides 3605 to the optical device 3602C, which may be further configured to multiplex the returned optical signal 3612 (if required) for transmission to the light receiving device 3603. The returned optical signal 3612 may be directed by the optical device 3602C through the optical device 3602B and towards the optical device 3602D, which may be a WDM device configured to de-multiplex the returned optical signal 3612 for reception by the light receiving device 3603.

Optical device 3602D may be in optical communication with the third port of the optical device 3602B for receiving the returned optical signal and dividing it into individual wavelength components. The light receiving device 3603, which may be a photodetector array, for example, may be in optical communication with optical device 3602D for receiving the individual wavelength components of the returned optical signal, such that detected phase shifts or other changes in the individual wavelength components are indicative of sensed acoustic signals.

It will be understood that, in embodiments that do not require frequency multiplexing/demultiplexing of the initial optical signal 3611 and the returned optical signal 3612 the optical devices 3602A and 3602C may not be required. For example, individual transmission pathways may be extended between an operating laser array of the light source 3604 to the optical sensor array 3601. The light receiving device 3603 may include any suitable device configured to detect incident light, including, for example, a photodetector. The light receiving device 3603 may further include, but is not limited to, a photodiode array. The light receiving device 3603 may be in optical communication with the optical device 3602D (e.g., a wavelength division multiplexing splitter) for receiving the individual wavelength components of the returned optical signal 3612, such that detected phase shifts, changes in polarization, or other changes in the individual wavelength components are indicative of sensed acoustic signals. The changes in the returned optical signal 3612 may be converted (e.g., by the processing unit 3609 and/or by additional optical components such as polarization sensitive couplers and/or frequency shifters) into data representative of sensed acoustic signals and may be further used, e.g., to generate data representative of the tissue/anatomical structure and physical parameters for which the mixed sensor array probe 3660 is used. In embodiments, the initial optical signal 3611 and returned optical signal 3612 signals may undergo pre-processing, beamforming and post-processing, as described herein. The image and/or data provided by the optical sensor array 3601 may then be displayed to the user on output device 3608, which may include a computer display or the like.

As discussed above, the light receiving device 3603 is in communication with the processing unit 3609. The processing unit 3609 receives information signals from the light receiving device 3603 that are representative of the returned optical signal 3612 received at the light receiving device 3603. The processing unit 3609 may also receive information signals from the light control unit 3607 that are representative of the initial optical signal 3611 output by the light source 3604. The processing unit 3609 operates to process the information signals associated with the returned optical signal 3612 (optionally in comparison with the information signals associated with the initial optical signal 3611) to make determinations about an acoustic environment. Acoustic environment determinations may include the detection, identification, and interpretation of acoustic signals incident upon the sensors of the fiber optical sensor array 3601, which may include tissue imaging and physical parameters sensing. Processing unit 3609 may determine the presence and nature of acoustic signals incident upon the fiber optical sensors of the fiber optical sensor array.

Accordingly, the fiber optical array 3601 may function to detect and/or receive acoustic (e.g., ultrasound) signals, and provide optical signals that are representative of and consistent with the acoustic signals through an optical receive chain (e.g., optical devices 3602C, 3602B, 3602D) to a light receiving device 3603 configured to detect and/or receive the optical signals and provide electrical signals representative of and consistent with the optical signals to the processing unit 3609 for processing and interpretation. Thus, the processing unit 3609 may be configured to receive electrical signals that are representative of and consistent with the received acoustic signals and to process and interpret the electrical signals to reconstruct an image from the acoustic signals and/or provide sensed physical parameter data.

The processing unit 3609 may further be in communication with an acoustic control unit 3622. The acoustic control unit 3622 may be configured to provide control data to and receive signal data from the AEG array 3645 of the mixed sensor array 3661. The data received by the processing unit 3609 from the AEG array 3645 and the optical sensor array 3601 may be combined to provide an ultrasound image of increased quality as compared to that provided by either the AEG elements alone or optical sensors alone. Example methods of combination may include, for example, a delay and sum method performed by a beamformer, separate beamformer processing of each signal followed by compounding by applying frequency filters and weighed summation. Compounding methods may differ according to imaging depths.

The processing unit 3609 is configured to use the information signals from the mixed sensor array 3661 according to any of the embodiments disclosed herein, including for the purposes of tracking, imaging, detection, physical parameter sensing, measurement etc. Acoustic determination information may be output via the output device 3608, which may be, for example, a display, another medical system, etc.

It will be understood that the configuration of the optical acoustic sensor system 3600 as illustrated in FIG. 36 is provided by way of example. Different configurations may be employed without departing from the scope of this disclosure. For example, different arrangements of optical devices 3602A/B/C/D, different numbers and arrangements of fiber optical sensors 101 and fiber optical sensor arrays 3601 may be employed. In embodiments, the light source control unit 3607 and the acoustic control unit 3622 may be incorporated or integrated within the processing system 3650. Additional combinations of the components of the optical acoustic sensor system 3600 may be selected as appropriate to achieve the functionality as described herein.

Figure 37:
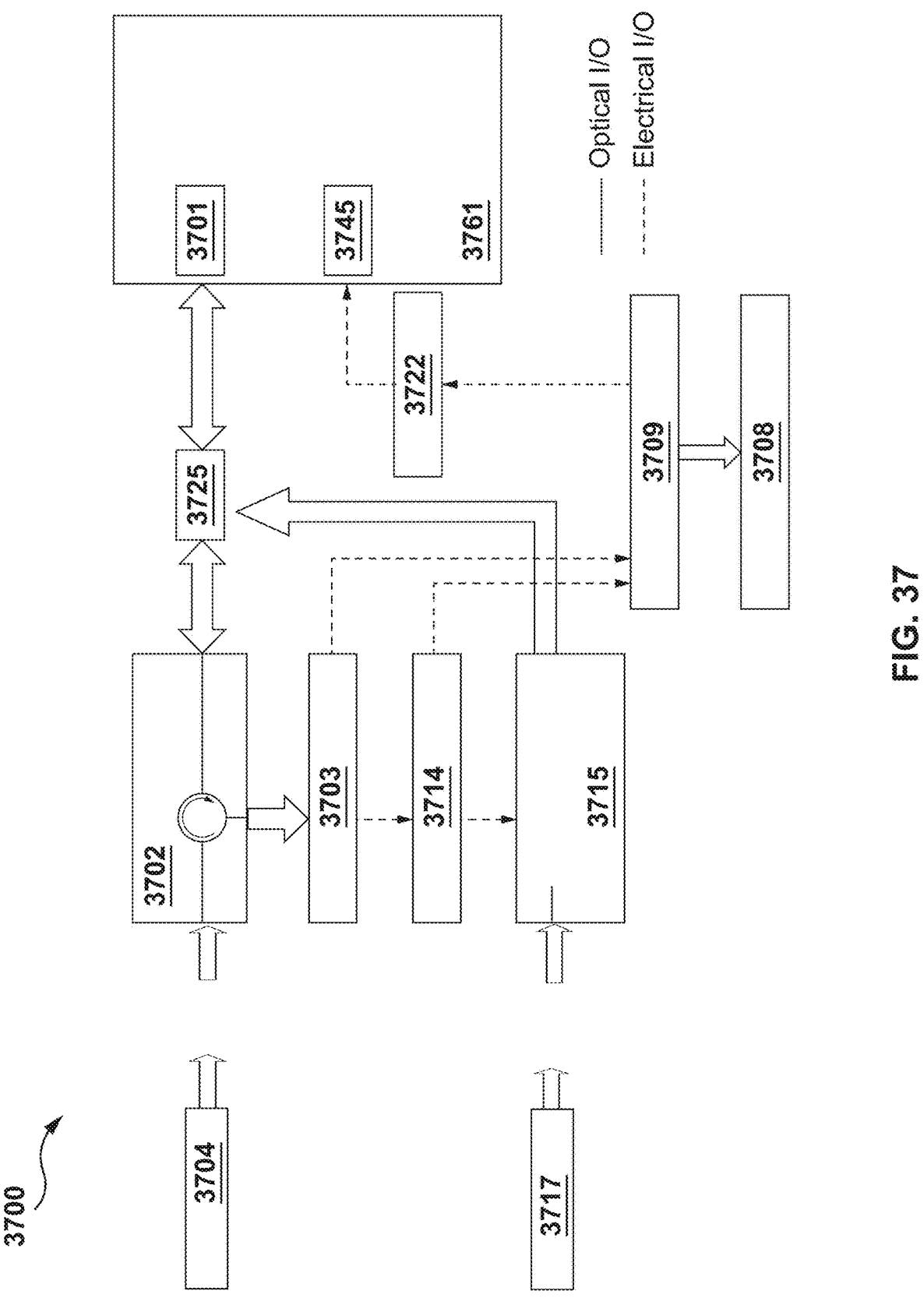
FIG. 37 illustrates an optical acoustic sensor system for use with a mixed sensor array according to embodiments herein.

FIG. 37 illustrates an optical acoustic sensor system for use with a mixed sensor array. The optical acoustic sensor system 3700 includes components, devices, hardware, and software to facilitate the use of a mixed sensor array 3761 consistent with any of FIGS. 28A-30B. Certain aspects of the optical acoustic sensor system 3700 are similar to that of optical acoustic sensor system 3600 and are not repeated. Aspects that differ are described below.

The optical acoustic sensor system includes a light source 3704, including a single laser or several lasers (e.g., to boost power) operating at a same frequency. The initial optical signal from the light source 3704 is separated by an optical splitter 3731 into a number of channels that corresponds to the number of fiber optic sensors in the optical sensor array 3701. The initial optical signal passes through an optical circulator array 3702, including a number of circulators that corresponds to the number of fiber optic sensors, with each signal being directed to a WDM unit from a WDM array 3725. While an optical circulator array 3702 is discussed, optical components such as optical couplers may be used instead. If a plurality of operating lasers is used as the light source 3704, a plurality of optical splitters 3731 may be used.

The optical acoustic sensor system also includes a heating source 3717, including a single laser or several lasers (e.g., to boost power) operating at a same frequency. The heating source 3717 operates at a frequency configured for thermal absorption by the fiber optical sensors of the optical sensor array 3701, as discussed herein. The initial thermo-optical signal from the heating source 3717 is separated by an optical splitter 3732 into a number of channels that corresponds to the number of fiber optic sensors in the optical sensor array 3701. If a plurality of lasers are used as the heating source 3717, a plurality of optical splitters 3732 may be used. The initial thermo-optical signal(s) pass through a thermal tuning unit 3715, that operates to adjust the intensity of each thermos-optical signal to tune the individual optical sensors of the optical sensor array 3701. The thermal tuning unit may operate, for example, by use of an electrical variable optical attenuator (E-VOA), such as MEMS-based VOA, fiber to fiber based VOA, electro-optical based VOA or acoustic-optical based VOA. The resultant tuned thermo-optical signals are provided to the WDM array 3725 to be multiplexed with a corresponding initial optical signal and provided to the appropriate optical sensor of the optical sensor array 3701. The thermal tuning unit 3715 is controlled by the thermal control unit 3714 which receives input from the light receiving device array 3703. Input from the light receiving device array 3703 is used in a feedback loop to control the heating (and thus the thermal tuning properties) of each fiber optic sensor of the optical sensor array 3701 individually. The thermal tuning process is described above and may be used to tune the individual fiber optic sensors of the optical sensor array 3701 to be sensitive to the same operating laser frequency.

Additional features of the optical acoustic sensor system 3700 are similar to those of optical acoustic sensor system 3600. The returned optical signals are filtered from the thermo-optical signals and passed through the circulator array 3702 where they are directed to the light receiving device array 3703. Alternatively, the light receiving device array 3703 may be selected as a device that is relatively insensitive to the wavelength of the thermo-optical signals, allowing receipt of these signals without unduly affecting the temperature of the light receiving device array 3703. The light receiving device array 3703 is configured to receive the multiple returned optical signals (e.g., via individual light receiving devices of the array, wherein each light receiving device corresponds to one of the channels into which the initial optical signal is separated) and provide information and data thereof to the processing unit 3709. The individual light receiving devices may be, for example, individual photodetectors. The processing unit 3709 further communicates with the AEG array 3745 via the acoustic control unit 3722. Information from the AEG array 3745 and the optical sensor array 3701 are used by the processing unit 3709 in acoustic environment determinations, including, e.g., imaging and sensed physical parameters data. In addition, the processing unit 3709 may also receive output from the thermal tuning control unit 3714 for use in interpreting the returned optical signals. Acoustic determination information may be output via the output device 3708, which may be, for example, a display, another medical system, etc.

The optical acoustic sensor system 3700 significantly reduces the required number of lasers for the light source 3704 by splitting the optical signal from a single light source 3704 into multiple channels. This may reduce the cost, size, and power consumption of the system 3700. A reduction in the total number of lasers required for the light source 3704 may represent a significant reduction in cost, size, power consumption, and complexity. In embodiments, a number of lasers less than the total number of fiber optic sensors may be used (e.g., to boost power). Each of the multiple lasers may be tuned to a same wavelength and split.

Figure 38:
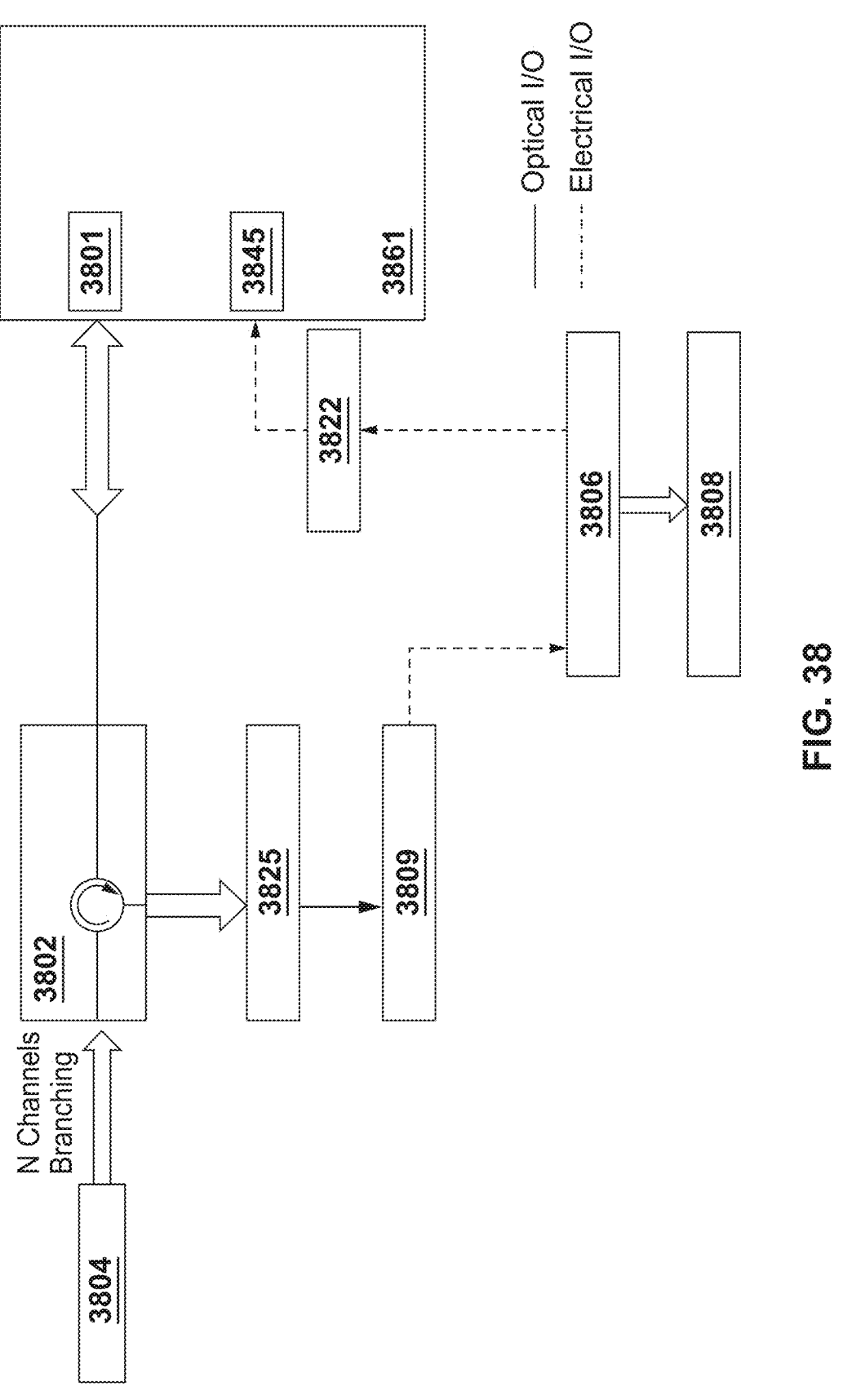
FIG. 38 illustrates an optical acoustic sensor system for use with a mixed sensor array according to embodiments herein.

FIG. 38 illustrates an optical acoustic sensor system for use with a mixed sensor array. The optical acoustic sensor system 3800 includes components, devices, hardware, and software to facilitate the use of a mixed sensor array 3861 employing polarization based fiber sensors and consistent with any of FIGS. 31-35C. Certain aspects the optical acoustic sensor system 3800 are similar to that of optical acoustic sensor systems 3600 and 3700 and are not repeated. Aspects that differ are described below.

The optical acoustic sensor system includes a light source 3804, including a single laser or several lasers operating at a same frequency (e.g., to boost power). The initial optical signal from the light source 3804 is separated into a number of channels that corresponds to the number of fiber optic sensors in the optical sensor array 3801. The initial optical signal passes through an optical circulator array 3802, including a number of circulators that corresponds to the number of fiber optic sensors, with each signal being directed to its corresponding fiber optical sensor of the optical sensor array 3801. While an optical circulator array 3802 is discussed, optical components such as optical couplers may be used instead.

Additional features of the optical acoustic sensor system 3800 are similar to those of optical acoustic sensor systems 3600 and 3700 as well as the system 100B described above with respect to FIG. 6A. The returned optical signals are passed through the circulator array 3802 where they are directed to the polarization filter array 3825. The polarization filter array 3825 is configured to receive the multiple returned optical signals, filter by polarization and pass the signals to the light receiving device array 3809, which may be, for example, a photodetector array. The polarization filter array 3825 may be an array of polarization filters or analyzers that permit light of specific polarizations to pass through to the light receiving device array 3809. When the polarization of the transmitted light is changing, the amplitude of the light passed to the light receiving device array 3809 varies accordingly and can be detected. Information from the light receiving device array 3809 is passed to the processing unit 3806. The processing unit 3806 further communicates with the AEG array 3845 via the acoustic control unit 3822. Information from the AEG array 3845 and the optical sensor array 3801 are used by the processing unit 3806 in acoustic environment determinations, including, e.g., imaging and physical parameters sensing. Acoustic determination information may be output via the output device 3808, which may be, for example, a display, another medical system, etc.

Figures 39A, 39B, 39C:
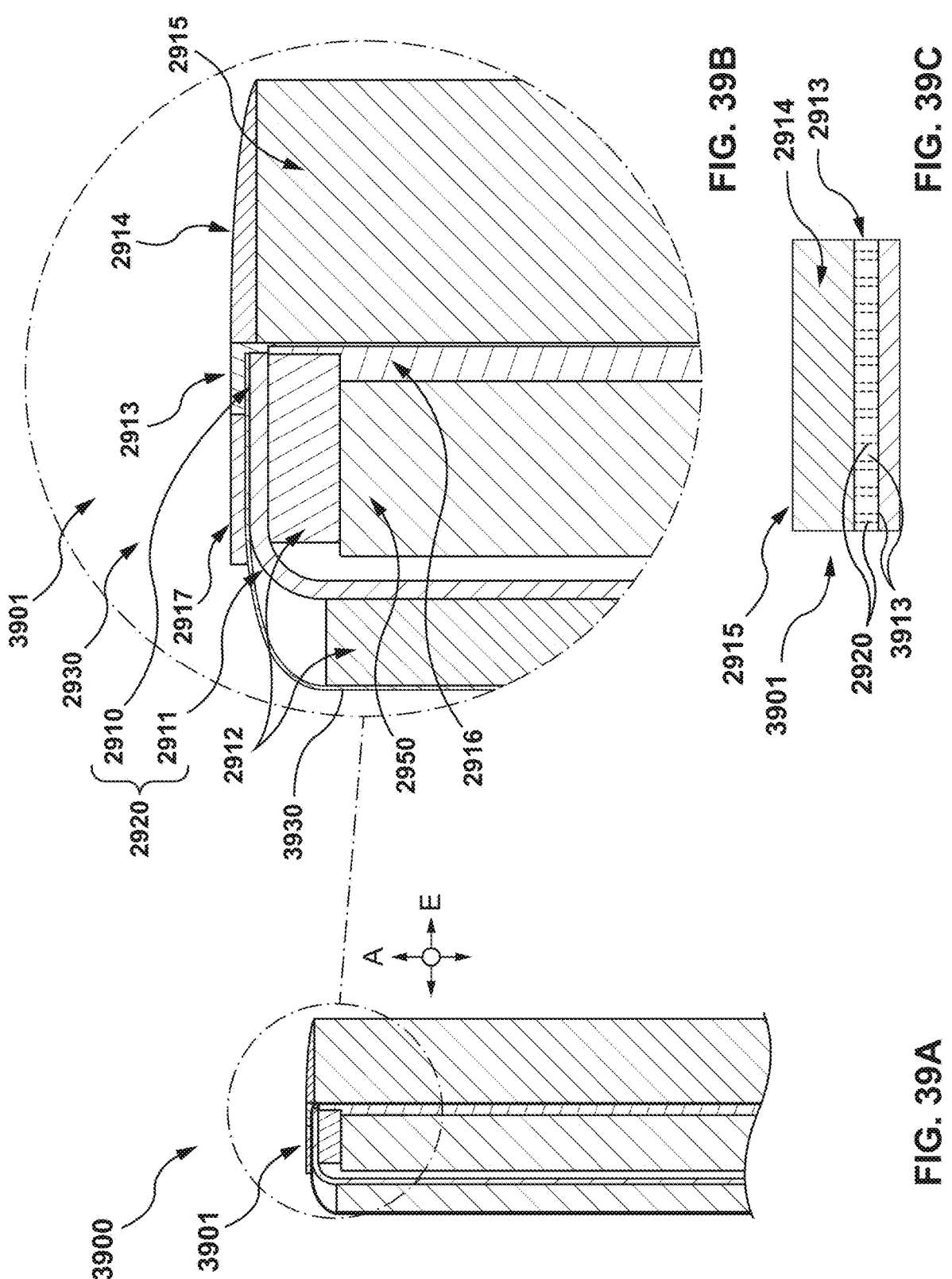
FIGS. 39A and 39B illustrate a structure of a mixed array probe head module according to embodiments herein.
FIG. 39C provides an axial view of a probe head module according to embodiments herein.

FIGS. 39A and 39B illustrate a structure of a mixed array probe head module according to embodiments herein. FIG. 39A illustrates a cross-sectional view of the probe head module 3901 and FIG. 39B provides an enlarged version. FIG. 39C provides an axial view of the probe head module 3901. The probe head module 3901 may be part of a mixed sensor array transducer 3900 and may be similar to the probe head module 2901 and includes many similar features. The probe head module 3901 differs from the probe head module 2901 in that it includes a micro-heating unit or array 3930. The micro-heating unit or array 3930 may incorporate a flex circuit having a plurality of heaters 3913, each corresponding to an individual fiber optic sensor 2920 of the optical sensor array 2930. During operation, the plurality of heaters 3913 of the micro-heating unit 3930 may be individually controlled to provide thermal tuning to the individual fiber optic sensors 2920, according to methods discussed herein. The plurality of heaters 3913 of the micro-heating unit 3930 may be positioned as closely as possible to the corresponding individual fiber optic sensors 2920 (e.g., the heaters 3913 may be in contact with the corresponding sensors) and may be thermally isolated from neighboring heaters 3913 and fiber optic sensor 2920. Thus, thermal cross-talk may be reduced and the individual fiber optic sensors 2920 may be more efficiently thermally tuned. Thus, the probe head module 3901 provides thermal tuning to the optical sensor array 2930. In further embodiments, the plurality of heaters 3913 may be provided as individual heaters not part of a flex circuit.

Figure 40:
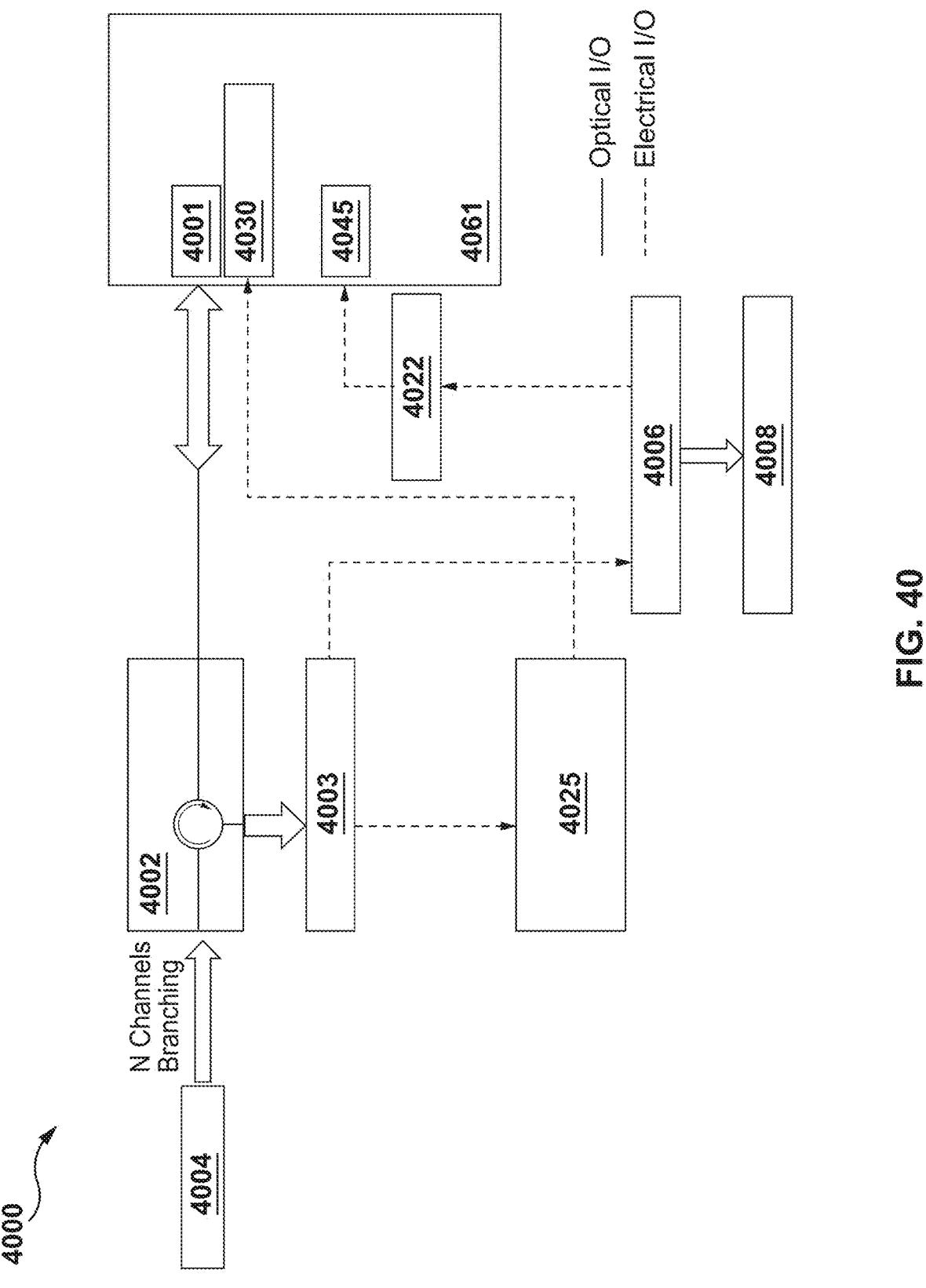
FIG. 40 illustrates an optical acoustic sensor system for use with a mixed sensor array according to embodiments herein.

FIG. 40 illustrates an optical acoustic sensor system for use with a mixed sensor array. The optical acoustic sensor system 4000 includes components, devices, hardware, and software to facilitate the use of a mixed sensor array 4061 employing a thermally tuned optical sensor array 4001. Certain aspects the optical acoustic sensor system 4000 are similar to that of optical acoustic sensor systems 3600, 3700, and 3800 and are not repeated. Aspects that may differ are described below.

The optical acoustic sensor system 4000 includes a light source 4004, including a single laser or several lasers operating at a same frequency (e.g., to boost power). The initial optical signal from the light source 4004 is separated into a number of channels that corresponds to the number of fiber optic sensors in the optical sensor array 4001. The initial optical signal passes through an optical circulator array 4002, including a number of circulators that corresponds to the number of fiber optic sensors, with each signal being directed to its corresponding fiber optical sensor of the optical sensor array 4001. While an optical circulator array 4002 is discussed, optical components such as optical couplers may be used instead.

The optical acoustic sensor system 4000 further includes a thermal tuning unit 4025. The thermal tuning unit 4025 controls individual heaters 3913 of a micro-heating unit 4030 (e.g., similar to the micro-heating unit 3930) to adjust the temperature and therefore thermally tune the individual fiber optic sensors of the optical sensor array 4001. Operation of the thermal tuning unit 4025 is informed by data from the light receiving device 4003 according to thermal tuning methods discussed herein.

Additional features of the optical acoustic sensor system 4000 are similar to those of optical acoustic sensor systems 3600, 3700, and 3800. The returned optical signals are passed through the circulator array 4002 where they are directed to the polarization filter array to the light receiving device 4003, which may be, for example, a photodetector array. Information from the light receiving device 4003 is passed to the processing unit 4006. The processing unit 4006 further communicates with the AEG array 4045 via the acoustic control unit 4022. Information from the AEG array 4045 and the optical sensor array 4001 are used by the processing unit 4006 in acoustic environment determinations, including, e.g., imaging. Acoustic determination information may be output via the output device 4008, which may be, for example, a display, another medical system, etc.

In further embodiments, real-time visualization of a device tip including a fiber optical sensor may be co-registered with a diagnostic ultrasound image, eliminating the need for calibration. This breakthrough allows clinicians to confidently track the device in challenging anatomical regions. Real-time confidence indicators of device tip intersection with an imaging plane may be provided, with special consideration to detect when a device tip leaves the imaging plane, which may ensure accurate device tip tracking even during complex procedures. Real-time prospective visualization of tip trajectory may be provided, providing valuable insights into a predicted path of the device tip and the visualization of a device tip trail, which may be used for enhanced procedural confidence and documentation. Further, devices incorporating fiber optical sensors as described herein may facilitate the display of anatomic and blood flow images from the indwelling sensors co-registered with cross-sectional images, which may enhance diagnostic precision and confidence.

Optical fiber sensor discussed herein may provide ultrasound receivers with high sensitivity, broad bandwidth, and a wide acceptance angle. Further optical fiber sensors do not require the electrical components needed for electro-mechanical transducers. Such features may permit the design and manufacture of transducer arrays with reduced footprints. Further, the technical capabilities of fiber optical sensors described herein may enable transducers to sense or identify harmonic or scattered signals that existing technologies cannot. Because of the high sensitivity and broad bandwidth of optical sensors, the image produced by the fiber optical sensors may also have improved spatial resolution, improved penetration depth, improved signal-to-noise ratio (SNR), improved tissue harmonic imaging, and/or improved Doppler sensitivity.

Embodiment 1 is an apparatus comprising: a housing; a substrate mounted within the housing; a plurality of sensor fibers secured to the substrate, each sensor fiber including: an optical waveguide; an optical sensor structure configured for: detecting an acoustic signal, and providing an optical signal corresponding to the acoustic signal to the optical waveguide, and a plurality of acoustic energy generating transducers configured to generate acoustic energy.

Embodiment 2 is the apparatus of embodiment 1, wherein the optical sensor structure is further configured for: detecting a physical parameter, and providing an optical signal corresponding to the physical parameter to the optical waveguide.

Embodiment 3 is the apparatus of embodiment 1 or 2, wherein the substrate includes: a first portion configured to cover the plurality of sensor fibers; and a second portion attached to the first portion and having a plurality of fiber optic sensor receiving portions corresponding to the plurality of sensor fibers.

Embodiment 4 is the apparatus of any of embodiments 1-3, further comprising at least one backing block configured to provide acoustic damping and located within the housing.

Embodiment 5 is the apparatus of any of embodiments 1-4, further comprising an interface layer disposed within the housing as an exterior layer of the apparatus between the plurality of sensor fibers and a surrounding environment, wherein optionally the interface layer comprises one or more of a moisture barrier, an electrical isolator, a matching layer, a couplant and acoustic lens.

Embodiment 6 is the apparatus of embodiments 1-5, further comprising an interface layer disposed within the housing as an exterior layer of the apparatus between the plurality of acoustic energy generating elements and a surrounding environment, wherein optionally the interface layer comprises one or more of a moisture barrier, an electrical isolator, a matching layer, a couplant and acoustic lens.

Embodiment 7 is the apparatus of any of embodiments 1-6, wherein: each optical sensor structure is provided at an end of a corresponding sensor fiber, and the plurality of sensor fibers are arranged axially within the housing.

Embodiment 8 is the apparatus of any of embodiments 1-7, wherein the plurality of sensor fibers are arranged in a first row and a second row on opposite sides of the plurality of acoustic energy generating transducers.

Embodiment 9 is the apparatus of any of embodiments 1-8, wherein: each optical sensor structure is provided at a distal end of a corresponding sensor fiber, and distal portions of the plurality of sensor fibers are arranged in an elevation dimension within the housing.

Embodiment 10 is the apparatus of any of embodiments 1-9, wherein each optical sensor structure is a polarization based fiber sensor.

Embodiment 11 is the apparatus of any of embodiments 1-10, wherein distal portions of the plurality of sensor fibers are arranged in an elevation dimension within the housing.

Embodiment 12 is the apparatus any of embodiments 1-11, wherein distal portions of the plurality of sensor fibers are arranged in a lateral dimension within the housing.

Embodiment 13 is the apparatus of any of embodiments 1-12, wherein exposed portions of the plurality of sensor fibers are spaced apart in the lateral dimension.

Embodiment 14 is the apparatus of any of embodiments 1-13, further comprising a plurality of heaters, each corresponding to one of the plurality of sensor fibers.

Embodiment 15 is the apparatus of any of embodiments 1-14, wherein the substrate is a chip and the plurality of sensor fibers share a single optical sensor structure.

Embodiment 16 is a system for generating ultrasound images, comprising: a light source configured to generate an initial optical signal; a first optical waveguide configured to direct the initial optical signal from the light source to a fiber optic acoustic sensor array configured to detect acoustic signals; a light receiving device configured to receive a returned optical signal from the fiber optic acoustic sensor array and to generate optical signal data based on the returned optical signal; a second optical waveguide configured to direct the returned optical signal to the light receiving device; an acoustic control unit configured to provide acoustic control data to and receive acoustic signal data from an array of acoustic energy generating transducers; and a processing system configured to receive the optical signal data and the acoustic signal data and to generate a data output.

Embodiment 17 is the system of embodiment 16, wherein the data output is an ultrasound image.

Embodiment 18 is the system of embodiment 16 or 17, wherein the data output includes tracking or location information.

Embodiment 19 is the system of any of embodiments 16-18, wherein the light source is a laser.

Embodiment 20 is the system of embodiment 19, further comprising at least one optical splitter configured to direct the initial optical signal to individual sensors of the fiber optic acoustic sensor array.

Embodiment 21 is the system of any of embodiments 16-20, wherein the light source is a laser array configured to provide the initial optical signal to individual sensors of the fiber optic acoustic sensor array.

Embodiment 22 is the system of any of embodiments 16-21, wherein the light receiving device includes a photodetector array.

Embodiment 23 is the system of any of embodiments 16-22, further comprising at least one tuning laser configured for providing a thermo-optical signal for thermal tuning of the fiber optic acoustic sensor array.

Embodiment 24 is the system of any of embodiments 16-23, further comprising an optical splitter configured to direct the thermo-optical signal to individual sensors of the fiber optic acoustic sensor array.

Embodiment 25 is the system of any of embodiments 16-24, further comprising at least on multiplexer configured to multiplex the thermo-optical signal with the initial optical signal.

Embodiment 26 is the system of any of embodiments 16-25, further comprising a thermal tuning unit configured to adjust a level of thermal tuning provided to the fiber optic acoustic sensor array.

Embodiment 27 is the system of any of embodiments 16-26, further comprising a thermal tuning unit configured to adjust temperatures of heaters associated with the fiber optic sensor array to thermally tune the fiber optic sensor array.

Embodiment 28 is an apparatus comprising: a housing; a substrate mounted within the housing; a plurality of sensor fibers secured to the substrate, each sensor fiber including: an optical waveguide; an optical sensor structure configured for: detecting a physical parameter, and providing an optical signal corresponding to the physical parameter to the optical waveguide, and a plurality of acoustic energy generating transducers configured to generate acoustic energy.

Embodiment 29 is the apparatus of embodiment 28, wherein the physical parameter includes at least one of temperature and pressure.

Embodiment 30 is the apparatus of embodiment 29, wherein the optical signal corresponding to the physical parameter of pressure corresponds to acoustic signals.

Embodiment 31 is the apparatus of any of embodiments 28-30, wherein a first sensor fiber of the plurality of sensor fibers has a first sensitivity to the physical parameter and a second sensor fiber of the plurality of sensor fibers has a second sensitivity to the physical parameter, different than the first sensitivity.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "includes" and/or "including," when used in this specification, specify the presence of stated features, integers, steps, operations, elements, and/or components, but do not preclude the presence or addition of one or more other features, integers, steps, operations, elements, components, and/or groups thereof.

The invention claimed is:

1. An apparatus comprising:
a housing;
a substrate mounted within the housing;
a plurality of sensor fibers secured to the substrate, each sensor fiber including:
an optical waveguide, and
an optical sensor structure configured for
detecting an acoustic signal, and
providing an optical signal corresponding to the acoustic signal to the optical waveguide; and
a plurality of electro-mechanical acoustic energy generating transducers disposed adjacent to the plurality of sensor fibers within the housing and configured to generate acoustic energy,
wherein:
each optical sensor structure is provided at a distal tip of a corresponding sensor fiber,
the plurality of sensor fibers are arranged axially within the housing, and
the plurality of sensor fibers are arranged in a first row to form a first linear fiber optical sensor array and a second row to form a second linear fiber optical sensor array, the first linear optical sensor array and the second linear fiber optical sensor array being displaced from one another in an elevation dimension on opposite sides of the plurality of acoustic energy generating transducers to provide 1.5D imaging.

2. The apparatus of claim 1, wherein each optical sensor structure is further configured for:
detecting a physical parameter, and
providing an optical signal corresponding to the physical parameter to the optical waveguide.

3. The apparatus of claim 1, wherein the substrate includes:
a first portion configured to cover the plurality of sensor fibers; and
a second portion attached to the first portion and having a plurality of fiber optic sensor receiving portions corresponding to the plurality of sensor fibers.

4. The apparatus of claim 1, further comprising an interface layer disposed within the housing as an exterior layer of the apparatus between the plurality of sensor fibers and a surrounding environment.

5. The apparatus of claim 4, wherein the interface layer comprises one or more of a moisture barrier, an electrical isolator, a matching layer, a couplant and an acoustic lens.

6. The apparatus of claim 1, further comprising an interface layer disposed within the housing as an exterior layer of the apparatus between the plurality of acoustic energy generating transducers and a surrounding environment.

7. The apparatus of claim 6, wherein the interface layer comprises one or more of a moisture barrier, an electrical isolator, a matching layer, a couplant and an acoustic lens.

8. The apparatus of claim 1, wherein:
each optical sensor structure is provided at a distal tip of a corresponding sensor fiber, and
distal portions of the plurality of sensor fibers are arranged in an elevation dimension within the housing.

9. An apparatus comprising:
a housing;

a substrate mounted within the housing;
a plurality of sensor fibers secured to the substrate, each sensor fiber including:
an optical waveguide, and
an optical sensor structure configured for:
detecting an acoustic signal, and
providing an optical signal corresponding to the acoustic signal to the optical waveguide, and
a plurality of electro-mechanical acoustic energy generating transducers disposed adjacent to the plurality of sensor fibers within the housing and configured to generate acoustic energy, wherein:
each sensor fiber of the plurality of sensor fibers further includes an encapsulating structure surrounding the optical waveguide,
each optical sensor structure includes an exposed portion defined by a lack of the encapsulating structure, and
each optical sensor structure is a polarization based fiber sensor configured to receive the acoustic signal at the exposed portion and to cause an alteration in polarization of the optical signal traveling through the optical waveguide in response to the acoustic signal.

10. The apparatus of claim 9, wherein each sensor fiber includes a plurality of exposed portions spaced apart in the lateral dimension.

11. An apparatus comprising:
a housing;
a substrate mounted within the housing;
a plurality of sensor fibers secured to the substrate, each sensor fiber including:
an optical waveguide, and
an optical sensor structure configured for:
detecting an acoustic signal, and
providing an optical signal corresponding to the acoustic signal to the optical waveguide, and
a plurality of electro-mechanical acoustic energy generating transducers disposed adjacent to the plurality of sensor fibers within the housing and configured to generate acoustic energy, wherein:
proximal portions of the plurality of sensor fibers extend through the housing in an axial dimension,
the substrate is configured to maintain a bend in each of the plurality of sensor fibers such that distal portions of the plurality of sensor fibers are disposed along an elevation dimension of the housing, and
the plurality of sensor fibers are configured to receive the acoustic signal from directions lateral to the axes of the plurality of sensor fibers.

12. An apparatus comprising:
a housing;
a substrate mounted within the housing;
a plurality of sensor fibers secured to the substrate, each sensor fiber including:
an optical waveguide, and
an optical sensor structure configured for:
detecting an acoustic signal, and
providing an optical signal corresponding to the acoustic signal to the optical waveguide, and
a plurality of electro-mechanical acoustic energy generating transducers disposed adjacent to the plurality of sensor fibers within the housing and configured to generate acoustic energy, wherein:
proximal portions of the plurality of sensor fibers extend through the housing in an axial dimension,
the substrate is configured to maintain a bend in each of the plurality of sensor fibers such that distal portions of the plurality of sensor fibers are disposed along a lateral dimension of the housing, and the plurality of sensor fibers are configured to receive the acoustic signal from directions lateral to the axes of the plurality of sensor fibers.

13. An apparatus comprising:

a housing;

a substrate mounted within the housing;

a plurality of sensor fibers secured to the substrate, each sensor fiber including:

an optical waveguide, and an optical sensor structure configured for:

detecting an acoustic signal, and providing an optical signal corresponding to the acoustic signal to the optical waveguide, and a plurality of electro-mechanical acoustic energy generating transducers disposed adjacent to the plurality of sensor fibers within the housing and configured to generate acoustic energy further comprising at least one heater disposed adjacent to the plurality of sensor fibers and configured to be controlled to provide thermal tuning to at least one of the plurality of sensor fibers.

14. The apparatus of claim 13, wherein the at least one heater includes a plurality of heaters, each disposed adjacent to a corresponding one of the plurality of sensor fibers and configured to be individually controlled to provide thermal tuning to the corresponding one of the plurality of sensor fibers.

15. An apparatus comprising:

a housing;

a substrate mounted within the housing, wherein the substrate is a chip;

a plurality of sensor fibers secured to the substrate, each sensor fiber including:

an optical waveguide;

an optical sensor structure comprising a single shared optical sensor structure for the plurality of sensor fibers, wherein the plurality of sensor fibers is configured for detecting an acoustic signal, and providing an optical signal corresponding to the acoustic signal to the optical waveguide; and a plurality of electro-mechanical acoustic energy generating transducers configured to generate acoustic energy.

16. The apparatus of claim 15, wherein each optical sensor structure is further configured for:

detecting a physical parameter, and providing an optical signal corresponding to the physical parameter to the optical waveguide.

17. The apparatus of claim 15, further comprising an interface layer disposed within the housing as an exterior layer of the apparatus between the plurality of sensor fibers and a surrounding environment, the interface layer including one or more of a moisture barrier, an electrical isolator, a matching layer, a couplant and an acoustic lens.

18. The apparatus of claim 15, further comprising an interface layer disposed within the housing as an exterior layer of the apparatus between the plurality of acoustic energy generating transducers and a surrounding environment.

19. The apparatus of claim 18, wherein the interface layer comprises one or more of a moisture barrier, an electrical isolator, a matching layer, a couplant and an acoustic lens.

20. The apparatus of claim 15, wherein:

the optical sensor structure is provided at a distal tip of a corresponding sensor fiber, and the plurality of sensor fibers are arranged along an axial direction within the housing.

21. The apparatus of claim 15, wherein distal portions of the plurality of sensor fibers are disposed along an elevation dimension within the housing.

22. The apparatus of claim 15, wherein distal portions of the plurality of sensor fibers are disposed along a lateral dimension within the housing.

23. The apparatus of claim 15, further comprising at least one heater disposed adjacent to the plurality of sensor fibers and configured to be controlled to provide thermal tuning to at least one of the plurality of sensor fibers.

24. The apparatus of claim 23, wherein the at least one heater includes a plurality of heaters, each disposed adjacent to a corresponding one of the plurality of sensor fibers and configured to be individually controlled to provide thermal tuning to the corresponding one of the plurality of sensor fibers.

* * * * *